United States Patent
Endou et al.

(10) Patent No.: US 7,553,642 B2
(45) Date of Patent: Jun. 30, 2009

(54) BRANCHED NEUTRAL AMINO ACID TRANSPORTERS ACTING AS SINGLE MOLECULE

(75) Inventors: Hitoshi Endou, Kanagawa (JP); Yoshikatsu Kanai, Tokyo (JP)

(73) Assignee: Human Cell Systems, Inc., Tokyo (JP)

( * ) Notice: Subject to any disclaimer, the term of this patent is extended or adjusted under 35 U.S.C. 154(b) by 238 days.

(21) Appl. No.: 10/547,975

(22) PCT Filed: Mar. 5, 2004

(86) PCT No.: PCT/JP2004/002905

§ 371 (c)(1),
(2), (4) Date: Sep. 6, 2005

(87) PCT Pub. No.: WO2004/078970

PCT Pub. Date: Sep. 16, 2004

(65) Prior Publication Data

US 2006/0246538 A1    Nov. 2, 2006

(30) Foreign Application Priority Data

Mar. 7, 2003    (JP) ............................. 2003-062379

(51) Int. Cl.
*G01N 33/00*    (2006.01)
*C12P 21/06*    (2006.01)
*C07K 14/00*    (2006.01)

(52) U.S. Cl. .......................... 435/86; 435/69.1; 530/350

(58) Field of Classification Search .................. None
See application file for complete search history.

(56) References Cited

U.S. PATENT DOCUMENTS 7,226,731 B1 *  6/2007  Chuaqui et al. ................ 435/6

FOREIGN PATENT DOCUMENTS

WO        WO-98/21328          5/1998

(Continued)

OTHER PUBLICATIONS

Cole et al. "cDNA sequencing and analysis of POV1 (PB39): A novel gene up-regulated in prostate cancer," Genomics, vol. 51, pp. 282-287, 1998.*

(Continued)

*Primary Examiner*—Rebecca E Prouty
*Assistant Examiner*—Alexander D Kim
(74) *Attorney, Agent, or Firm*—Peter F. Corless; Christine C. O'Day; Edwards Angell Palmer & Dodge LLP

(57) ABSTRACT

It is intended to provide amino acid transporters which act as a single molecule and transport neutral amino acids typified by branched amino acids, and genes thereof. A protein consisting of an amino acid sequence represented by SEQ ID NO:2, 4, 6 or 8 or an amino acid sequence derived from an amino acid sequence represented by SEQ ID NO:2, 4, 6 or 8 by deletion, substitution or addition of one to several amino acids, and being capable of sodium-independently transporting neutral amino acids typified by branched amino acids and analogs thereof as a single molecule. A gene which is a DNA consisting of a base sequence represented by SEQ ID NO:1, 3, 5 or 7 or a DNA hybridizable with it and encodes a protein capable of sodium-independently transporting branched amino acids as a single molecule.

2 Claims, 25 Drawing Sheets

FOREIGN PATENT DOCUMENTS

| WO | WO-00/05376 | 2/2000 |
| WO | WO-01/55435 A2 | 8/2001 |
| WO | WO-02/098917 A | 12/2002 |
| WO | WO-03/009814 A2 | 2/2003 |

OTHER PUBLICATIONS

Kanai et al. "Expression cloning and charactterization of a transporter for large neutral amino acids activated by the heavy chain of 4F2 antigen (CD98)," The Journal of Biological Chemistry, vol. 273, No. 37, pp. 23629-23632, Sep. 11, 1998.*

Chuaqui et al., US 7226731, SEQ ID No. 2 sequence alignment, result 2, database: Issued_Patents_AA.*

Cole et al. SEQ ID No. 2 sequence alignment, result 1, database: UniProt_8.4.*

Chuaqui et al., US 7226731, SEQ ID No. 6, sequence alignment result 2, database: Issued_Patents_AA.*

Bode et al., Glutamine transport in isolated human hepatocytes and transformed liver cells, Hepatology, 1995, vol. 21, pp. 511-520.*

Babu et al., Identification of a Novel System L Amino Acid Transporter Structurally Distinct from Heterodimeric Amino Acid Transporters, The Journal of Biological Chemistry, E publication date of Aug. 20, 2003, vol. 278, pp. 43838-43845.*

McGivan, Rat heptoma cells express novel transport systems for glutamine and glutamate in addition to those present in normal rat hepatocytes, Biochem. J., 1998, vol. 330, pp. 255-260.*

XP002451629, Database UniProt (Online) "Solute Carrier Family, 43, Member 2 (LAT4)", Retrieved from EBI accession No. Uniprot: Q8N370 (Oct. 1, 2002).

Babu et al., "Identification of a Novel System L Amino Acid Transporter Structurally Distinct from Heterodimeric Amino Acid Transporters", *Journal of Biological Chemistry*, vol. 278, No. 44, pp. 43838-43845 (Oct. 31, 2003).

Chuaqui et al., "Identification of a Novel Transcript Up-Regulated in a Clinically Aggressive Prostate Carcinoma", XP002120986, Urology, vol. 50, No. 2, pp. 302-307, Aug. 1997.

XP002451630, Database UniProt (Online) "Solute Carrier Family 43, Member 2 (Osteoclast-like Cell cDNA, Riken Full-length Enriched Library, Clone:I420004L03 Product: Hypothetical Protein, Full Insert Sequence) (6 Days Neonate Spleen cDNA, Riken Full-Length Enriched Library, Clone:F430106G01 Product:Weakly Similar to Prostate Cancer Overexpr", Retrieved from EBI accession No. UniProt: Q8CGA3 (Mar. 1, 2003).

* cited by examiner

Fig. 2

```
                                                      1
human LAT3  MAPTLQQAYRRRWWMACTAVLENLFFSAVLLGWGSLLIILKNEGFYSSTC
            ||||| |||||||||||||||| |||||||||||| |||| || ||||||| |
mouse LAT3  MAPTLKQAYRRRWWMACTAVVENLFFSAVLLGWASLLIMLKKEGFYSSLC
                 #                              2
            PAESSTNTTQDEQRRWPGCDQQDE-MLNLGFTIGSFVLSATTLPLGILMD
            |||   |||||||  |   |||| ||||||||||| |||||||||||||
            PAENRTNTTQDEQHQWTSCDQQ-EKMLNLGFTIGSFLLSATTLPLGILMD
                             3                             4
            RFGPRPVRLVGSACFTASCTLMALASRDVEALSPLIFLALSLNGFGGICL
            |||||| ||||||||| ||||||||||||| ||||||||||||||| ||||
            RFGPRPLRLVGSACFAASCTLMALASRDTEVLSPLIFLALSLNGFAGICL
                                         5                       6
            TFTSLTLPNMFGNLRSTLMALMIGSYASSAITFPGIKLIYDAGVAFVVIM
            ||||||||||||||||||| |||||||||||||||||||||||| | |||
            TFTSLTLPNMFGNLRSTFMALMIGSYASSAITFPGIKLIYDAGVPFTVIM
                                     *
            FTWSGLACLIFLNCTLNWPIEAFPAPEEVNYTKKIKLSGLALDHKVTGDL
            ||||||||||||||| ||||  |||||||| |||||||| ||||||||||
            FTWSGLACLIFLNCALNWPAEAFPAPEEVDYTKKIKLIGLALDHKVTGDR
            &             *
            FYTHVTTMGQRLSQKAPSLEDGSDAFMS-PQDVRGTSENLPERSVPLRKS
            |||||| ||||||| |  ||| |  ||  |  ||| ||  ||||| |||
            FYTHVTIVGQRLSQKSPSLEEGADAFISSP-DIPGTSEETPEKSVPFRKS
                                                  7
            LCSPTFLWSLLTMGMTQLRIIFYMAAVNKMLEYLVTGGQEHETNEQQQKV
            |||| | |||| ||||||| ||||| ||| || ||| |||| ||||| ||
            LCSPIFLWSLVTMGMTQLRVIFYMGAMNKILEFIVTGGKERETNEQRQKV
                                        8
            AETVGFYSSVFGAMQLLCLLTCPLIGYIMDWRIKDCVDAPTQGTVL----
            |||  |||| || ||||||||||||||||||||||||||||| || |
            EETVEFYSSIFGVMQLLCLLTCPLIGYIMDWRIKDCVDAPTEGT-LNENA
                                                          9
            --GDARDGVA-TKSIRPRYCKIQKLTNAISAFTLTNLLLVGFGITCLINN
               ||||||||  || || ||| ||||||| | ||||||||||| | |||
            SFGDARDG-ASTKFTRPRYRKVQKLTNAINAFTLTNILLVGFGIACLIKN
                                     10
            LBLQFVTFVLHTIVRGFFHSACGSLYAAVFPSNHFGTLTGLQSLISAVFA
            ||||    |||||||||||||| ||||||||||||||||||||||||||
            LBLQLLAFVLHTIVRGFFHSACGGLYAAVFPSNHFGTLTGLQSLISAVFA
              11                  12
            LLQQPLFMAMVGPLKGEPFWVNLGLLLFSLLGFLLPSYLFYYRARLQQEY
            ||||  ||||||||  | ||||||||| || ||||||||| ||| ||| ||
            LLQQLLFMAMVGPLHGDPFWVNLGLLLLSFLGFLLPSYLYYYRSRLQREY AANGMGPLKVLSGSEVTA-*.................
            ||  |||  |  ||
            ATNLVDPQKVLNTSKV-AT*.................
```

Fig. 3
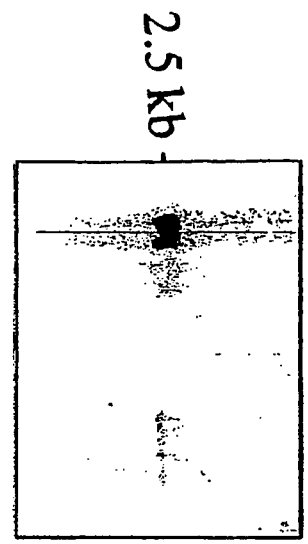
Fetal liver
Bone marrow
Peripheral leucocyte
Thymus
Lymph node
Spleen
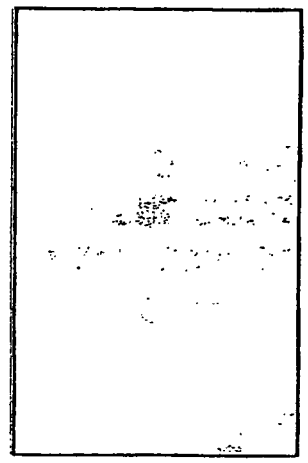
Peripheral leucocyte
Colon
Small intestine
Ovary
Testis
Prostate
Thymus
Spleen
Pancreas
Kidney
Skeletal muscle
Liver
Lung
Placenta
Brain
Heart

Fig. 14

```
human LAT3    MAPTLQQAYRRRWWMACTAVLENLFFSAVLLGWGSLLIILKNEGFYSSTC
              |||||  | |||||||||||||| |||||||||||||| ||  |||||  |
human LAT4    MAPTLATAHRRRWWMACTAVLENLLFSAVLLGWGSLLIMLKSEGFYSYLC --PAESSTN-T---TQD---EQRRWP-G---CDQ-QDEMLNLGFTIGSFV
                |  |  || |    | |    | |    |   |  |||||||| || |||
              TEP-ENVTNGTVGGTAEPGHEEVSWMNGWLSC-QAQDEMLNLAFTVGSFL LSATTLPLGILMDRFGPRPVRLVGSACFTA-SCTLMAL-ASRDVEALSPL
              |||  ||||||  ||  |||  ||||||| |  ||||| ||      ||| |
              LSAITLPLGIVMDKYGPRKLRLLGSACF--AVSCLLIAYGASKPN-ALSVL IFLALSLNGFGGICLTFTSLTLPNMFGNLRSTLMALMIGSYASSAITFPG
              || || ||||||| | ||||||||||||| |||| ||||||||||||||| ||||
              IFIALALNGFGGMCMTFTSLTLPNMFGDLRSTFIALMIGSYASSAVTFPG IKLIYDAGVAF-VVIMFTWSGLAC--LIFLNCTLNWPIEAFPAPEEVNYT
              |||||||||  | ||  |  ||   |  |   ||||  ||| | ||| ||  |
              IKLIYDAGVSFIVVLVV-WAG--CSGLVFLNCFFNWPLEPFPGPEDMDYS KKIKLSGLALDHKVTGDLFYTHVTTMGQRLSQ-------K---APSL-ED
              || |  |  ||| ||  || |||  ||| |||                |    | ||
              VKIKFSWLGFDHKITGKQFYKQVTTVGRRLSVGSSMRSAKEQVA--LQE- G-----S--DAFMSPQ-D--VRGTSENLPERSV--P-LRKSLCSPTFLWS
              |       |      |   | |   |     _||_ | |       |    | |
              GHKLCLSTVDLEVKCQPDAAVAP-SFMH---SVFSPIL---L------L-S LLTMGMTQLRIIFYMAAVNKMLEYLVTGGQEHETNEQQQKV--AETVGFYS
              .|  ||  ||||  |||| |  |  |  ||    |     ||||  |
              LVTMCVTQLRLIFYMGAMNNILKFLVSGDQK---T------VMA-TVGLYT SVFGAMQLLCLLTCPLIGYIMDWRIKDCVDA---PTQGTVLGDARDGVAT
              |  || |||||||| | |||||||||  | | ||   |       || |
              SIFGVLQLLCLLTAPVIGYIMDWRLKECEDASEEPEEK----DANQGEKK KSIRPRYCKIQKLTNAISAFTLTNLLLVGFGITCLINNLHLQFVTFVLHT
              |  | |    |||  ||| |||  || ||||||||||| |||| || ||    | |||
              KKKRDRQ--IQKITNAMRAFAFTNLLLVGFGVTCLIPNLPLQILSFILHT IVRGFFHSACGSLYAAVFPSNHFGTLTGLQSLISAVFALLQQPLFMAMVG
              ||||·| ||| | |||||| ||  || |||||||||||| ||||||||| ||  |
              IVRGFIHSAVGGLYAAVYPSTQFGSLTGLQSLISALFALLQQPLFLAMMG PLKGEPFWVNLGLLLFSLLGFLLPSYLFYYRA---R-LQQ--EYAANGMG
              || | ||| ||||  ||||| || ||  ||     |||   |
              PLQGDPLWVNVGLLLLSLLGFCLPLYLICYRRQLERQLQQRQEDDKLF--

PLKVLSGS---EVTA--*............................
              || ||    |   |
              -LKIN-GSSNQE--AFV*............................
```

Fig. 15

```
                                          1
human LAT4   MAPTLATAHRRRWWMACTAVLENLLFSAVLLGWGSLLIMLKSEGFYSYLC
             ||||||||||||||||||||||||||||||||||||||||||||||||||
mouse LAT4   MAPTLATAHRRRWWMACTAVLENLLFSAVLLGWGSLLIMLKSEGFYSYLC
                  # #                                       2
             TEPENVTNGTVGGTAEPGHEEVSWMNGWLSCQAQDEMLNLAFTVGSFLLS
             | |||||| |||| ||| || |  ||||| ||||| |||||||||||||
             TKPENVTNSTVGGSAEPEPEELSLVNGWLSCKAQDEILNLAFTVGSFLLS
                                  3
             AITLPLGIVMDKYGPRKLRLLGSACFAVSCLLIAYGASKPNALSVLIFIA
             ||||||| ||||||||||||||||||||||||||||||| |  |||||||
             AITLPLGIIMDKYGPRKLRLLGSACFAVSCLLIAYGASNPDSLSVLIFIA
                 4                                   5
             LALNGFGGMCMTFTSLTLPNMFGDLRSTFIALMIGSYASSAVTFPGIKLI
             ||||||||||||||||||||||||||||||||||||||||||||||||||
             LALNGFGGMCMTFTSLTLPNMFGDLRSTFIALMIGSYASSAVTFPGIKLI
                         6                              *
             YDAGVSFIVVLVVWAGCSGLVFLNCFFNWPLEPFPGPEDMDYSVKIKFSW
             |||| |||  |||||||||||| |||||||||||||| |||||||||||
             YDAGASFIGILVVWAGCSGLVFFNCFFNWPLEPFPGSEDMDYSVKIKFSW
                      *                 +   * *
             LGFDHKITGKQFYKQVTTVGRRLSVGSSMRSAKEQVALQEGHKLCLSTVD
             |||||||||||||||||||||||||||| |||| || ||||||||||||
             LGFDHKITGKQFYKQVTTVGRRLSVGSSMRTAKEQAALQEGHKLCLSTVD
                                   7
             LEVKCQPDAAVAPSFMBSVFSPILL-LSLVTMCVTQLRLIFYMGAMNNIL
             |||||||||||  ||||||| ||  ||| |||||||||||||||||| ||
             LEVKCQPDAAAAPSFMBSVPSP-LLVLSLVTMCVTQLRLIFYMGAMNSIL
                                              8
             KFLVSGDQKTVMATVGLYTSIFGVLQLLCLLTAPVIGYIMDWRLKECEDA
             ||| ||||||| |   ||||||| ||||||||||||||||| |||||| |
             EFLVRGDQKTV-A---LYTSIFGALQLLCLLTAPVIGYIMDWKLKECEDT
                                                             9
             SEEPEEKDANQGEKKKKKRDRQIQKITNAMRAFAFTNLLLVGFGVTCLIP
             ||||||   ||||| || ||||||| |||||||||||| |||||||||
             SEEPEEEGTQGEKKQK-RDRQIQKVTNAMRAFAFTNVLLVGFGVTCLIP
                                                10
             NLPLQILSFILHTIVRGFIHSAVGGLYAAVYPSTQFGSLTGLQSLISALF
             ||||||  |  ||||||||||||||||||||||||||||||||| ||||
             NLPLQIFSFVLHTIVRGFIHSAVGGLYAAVYPSTQFGSLTGLQSLVSALF
                 11                                12
             ALLQQPLFLAMMGPLQGDPLWVNVGLLLLSLLGFCLPLYLICYRRQLERQ
             ||||||  | ||||| ||||||||||  | ||||||||||||||||||
             ALLQQPLYLAMMGPLGGDPLWVNVGLLAMSMLGFCLPLYLICYRRQLERQ LQQ-RQEDBKLFLKINGSSNQEAFV*..................
             ||| | || |||||||||||| ||||
             LQQKR-EDSKLFLKINGSSNREAFV*..................
```

Fig. 17

```
human LAT3    MAPTLQQAYRRRWWMACTAVLENLFFSAVLLGWGSLLIILKNEGFYSSTC
              |||||  | |||||||||||||||| |||||||||||||| || |||||  |
human LAT4    MAPTLATAHRRRWWMACTAVLENLLFSAVLLGWGSLLIMLKSEGFYSYLC --PAESSTN-T---TQD---EQRRWP-G---CDQ-QDEMLNLGFTIGSFV
                | | || |   |     |       |   |  | |||||||| || |||
              TEP-ENVTNGTVGGTAEPGHEEVSWMNGWLSC-QAQDEMLNLAFTVGSFL LSATTLPLGILMDRFGPRPVRLVGSACFTA-SCTLMAL-ASRDVEALSPL
              ||| ||||||  ||  ||| || ||||||  | |||| ||  ||   |||  |
              LSAITLPLGIVMDKYGPRKLRLLGSACF-AVSCLLIAYGASKPN-ALSVL IFLALSLNGFGGICLTFTSLTPNMFGNLRSTLMALMIGSYASSAITFPG
              || || ||||||  | |||||||||||||| |||| ||||||||||||||  ||||
              IFIALALNGFGGMCMTFTSLTPNMFGDLRSTFIALMIGSYASSAVTFPG IKLIYDAGVAF-VVIMFTWSGLAC--LIFLNCTLNWPIEAFPAPEEVNYT
              |||||||||  | ||     |  |    |   |  ||||  ||| | || ||   |
              IKLIYDAGVSFIVVLVV-WAG--CSGLVFLNCFFNWPLEPFPGPEDMDYS KKIKLSGLALDHKVTGDLFYTHVTTMGQRLSQ--------K---APSL-ED
              ||| | |  ||| ||  || ||| ||| |||          |   | ||
              VKIKFSWLGFDHKITGKQFYKQVTTVGRRLSVGSSMRSAKEQVA--LQE- G------S--DAFMSPQ-D--VRGTSENLPERSV--P-LRKSLCSPTFLWS
              |        |    || |  |       |   ||   | |     | ||
              GHKLCLSTVDLEVKCQPDAAVAP-SFMH---SVFSPIL---L-----L-S LLTMGMTQLRIIFYMAAVNKMLEYLVTGGQEHETNEQQQKV-AETVGFYS
              | ||  |||| |||||||| | |   | ||  ||  |    | | | ||||  |
              LVTMCVTQLRLIFYMGAMNNILKFLVSGDQK--T------VMA-TVGLTT SVFGAMQLLCLLTCPLIGYIMDWRIKDCVDA---PTQGTVLGDARDGVAT
              | ||  |||||||| | |||||||||||| | ||   |        || |
              SIFGVLQLLCLLTAPVIGYIMDWRLKECEDASEEPEEK----DANQGEKK KSIRPRYCKIQKLTNAISAFTLTNLLLVGFGITCLINNLHLQFVTFVLHT
              | | |   ||| |||  || ||||||||||| |||| || ||  | |||
              KKKRDRQ--IQKITNAMRAFAFTNLLLVGFGVTCLIPNLPLQILSFILHT IVRGFFHSACGSLYAAVFPSNHFGTLTGLQSLISAVFALLQQPLFMAMVG
              ||||| || |  | ||||| ||  || |||||||||| ||| |||||||||| || |
              IVRGFIHSAVGGLYAAVYPSTQFGSLTGLQSLISALFALLQQPLFLAMMG PLKGEPFWVNLGLLLFSLLGFLLPSYLFYYRA---R-LQQ--EYAANGMG
              || | ||| ||| |||| || || || || ||      | |||   |
              PLQGDPLWVNVGLLLLSLLGFCLPLYLICYRRQLERQLQQRQEDDKLF--

PLKVLSGS---EVTA--*..............................
              || || ||     |
              -LKIN-GSSNQE--AFV*..............................
```

Fig. 18

```
                                            1
human LAT4  MAPTLATAHRRRWWMACTAVLENLLFSAVLLGWGSLLIMLKSEGFYSYLC
            ||||||||||||||||||||||||||||||||||||||||||||||||||
mouse LAT4  MAPTLATAHRRRWWMACTAVLENLLFSAVLLGWGSLLIMLKSEGFYSYLC
                # #                               2
            TEPENVTNGTVGGTAEPGHEEVSWMNGWLSCQAQDEMLNLAFTVGSFLLS
            | ||||||  ||||  |||  || |  ||||||  ||| |||||||||||||
            TKPENVTNSTVGGSAEPEPEELSLVNGWLSCKAQDEILNLAFTVGSFLLS
                                    3
            AITLPLGIVMDKYGPRKLRLLGSACFAVSCLLIAYGASKPNALSVLIFIA
            |||||||| ||||||||||||||||||||||||||||| |  ||||||||
            AITLPLGIIMDKYGPRKLRLLGSACFAVSCLLIAYGASNPDSLSVLIFIA
            4                          5
            LALNGFGGMCMTFTSLTLPNMFGDLRSTFIALMIGSYASSAVTFPGIKLI
            ||||||||||||||||||||||||||||||||||||||||||||||||||
            LALNGFGGMCMTFTSLTLPNMFGDLRSTFIALMIGSYASSAVTFPGIKLI
                      6                              *
            YDAGVSFIVVLVVWAGCSGLVFLNCFFNWPLEPFPGPEDMDYSVKIKFSW
            |||| ||| |||||||||||| ||||||||||||||||| ||||||||||
            YDAGASFIGILVVWAGCSGLVFFNCFFNWPLEPFPGSEDMDYSVKIKFSW
                  *                   +    * *
            LGFDHKITGKQFYKQVTTVGRRLSVGSSMRSAKEQVALQEGHKLCLSTVD
            ||||||||||||||||||||||||||||||||| ||| |||||||||||
            LGFDHKITGKQFYKQVTTVGRRLSVGSSMRTAKEQAALQEGHKLCLSTVD
                                        7
            LEVKCQPDAAVAPSFMHSVFSPILL-LSLVTMCVTQLRLIFYMGAMNNIL
            |||||||||| |||||||||||| | |||||||||||||||||||||  ||
            LEVKCQPDAAAAPSFMHSVFSP-LLVLSLVTMCVTQLRLIFYMGAMNSIL
                                   8
            KFLVSGDQKTVMATVGLYTSIFGVLQLLCLLTAPVIGYIMDWRLKECEDA
            |||         |  ||||||||||||||||||||||||||||||  ||||||
            EFLVRGDQKTV-A---LYTSIFGALQLLCLLTAPVIGYIMDWKLKECEDT
                                             9
            SEEPEEKDANQGEKKKKKRDRQIQKITNAMRAFAFTNLLLVGFGVTCLIP
            ||||||   |||||  | ||||||| ||||||||||| ||||||||||||
            SEEPEEEEGTQGEKKQK-RDRQIQKVTNAMRAFAFTNVLLVGFGVTCLIP
                                  10
            NLPLQILSFILHTIVRGFIHSAVGGLYAAVYPSTQFGSLTGLQSLISALF
            ||||||  || |||||||||||||||||||||||||||||||||||  ||||
            NLPLQIFSFVLHTIVRGFIHSAVGGLYAAVYPSTQFGSLTGLQSLVSALF
                 11                    12
            ALLQQPLFLAMMGPLQGDPLWVNVGLLLLSLLGFCLPLYLICYRRQLERQ
            ||||||| |||||||| |||||||||||   | |||||||||||||||||
            ALLQQPLYLAMMGPLGGDPLWVNVGLLAMSMLGFCLPLYLICYRRQLERQ LQQ-RQEDDKLFLKINGSSNQEAFV*..................
            ||| | ||  ||||||||||||| |||||
            LQQKR-EDSKLFLKINGSSNREAFV*..................
```

Northern blot analysis of mouse LAT4

Northern blot analysis of human LAT4

Northern blot analysis of mouse LAT4

BRANCHED NEUTRAL AMINO ACID TRANSPORTERS ACTING AS SINGLE MOLECULE

The present application is a 371 national stage application of PCT/JP2004/002905, filed Mar. 5, 2004.

TECHNICAL FIELD

The present invention relates to a protein that participates in sodium-independently transporting branched neutral amino acids and analogs thereof, and a gene encoding the same.

BACKGROUND ART

Cells need to uptake amino acids regularly for nutrition, and this function is played by amino acid transporters, which are membrane proteins locating on the cell membrane. In particular, a neutral amino acid transport system L, which takes a part in supplying various essential amino acids to cells, is one of the most important transport mechanisms for cellular nutrition, and this system plays important roles in absorption from the intestine, resorption from the renal tubular, and passing through the blood tissue barrier as well. Further, the neutral aminoacid transport system L has been known to transport analogs of the neutral amino acids or drugs and toxic substances having similar structure to the neutral amino acid as well, due to wide selectivity for substrate.

The neutral amino acid transport system L has been originally first reported as an amino acid transport system in a cancer cell line being inhibited specifically by 2-aminobicyclo-(2,2,1)-heptane-2-carboxylic acid (BCH) as an analogous compound to amino acid. Since then, the system L has been studied using cultured cells, specimens of membrane vesicles, specimens of removed organs, or in vivo specimens (Christensen, Physiological Reviews, Vol. 70, No. 1, 43-77 (1990)). The neutral amino acid transport system L is sodium-independent transporter, in other words, the transport system L does not require sodium ion for its function. It has been known that there are differences in selectivity for a substrate to be transported and transport characteristics depending on each cell and tissue.

However, by means of the conventional methods, it is difficult to analyze details of the transportation of the neutral amino acids and their analogs and the role of the neutral amino acid transport system L for viability or growth of cells. Enabling precise analysis of the function has been desired by isolating genes of the neutral amino acid transporter, which takes on the function of the neutral amino acid transport system L.

With regard to the neutral amino acid transporter, sodium-dependent transporters, ASCT 1 and ASCT 2, have been cloned (Kanai, Current Opinion in Cell Biology, Vol. 9, No. 4, 565-572 (1997)). However, these transporters, which work principally with alanine, serine, cysteine, threonine and glutamine as main substrates, are different from the neutral amino acid transport system L in substrate selectivity. Further, a glycine transporter and a proline transporter have been cloned, but these are also different from the neutral amino acid transport system L (Amara and Kuhar, Annual Review of Neuroscience, Vol. 16, 73-93 (1993)).

cDNAs of rBAT and 4F2hc have been cloned, which are not the transporters themselves, but considered to be activators of the amino acid transporters and are type-2 membrane glycoproteins having only a single transmembrane structure, and it is known that when these cDNAs are expressed in Xenopus oocyt uptake of basic amino acids as well as neutral amino acids have been activated (Palacin, The Journal of Experimental Biology, Vol. 196, 123-137 (1994)).

As a transporter corresponding to the transport system L, a neutral amino acid transporter LAT1 (Kanai et al., The Journal of Biological Chemistry, Vol. 273, No. 37, 23629-23632 (1999)) and LAT2 (Segawa et al., The Journal of Biological Chemistry, Vol. 274, No. 28, 19745-19751 (1999)) have been cloned. Both of them are transporters functioning by forming heterodimers with 4F2hc and exhibiting sodium-ion ($Na^+$) independent transport. LAT1 shows an exchange transport activity for large neutral amino acids such as leucine, isoleucine, valine, phenylalanine, tyrosine, tryptophan, methionine and histidine, and LAT2 has wide substrate selectivity of transport not only for large neutral amino acids but for small neutral amino acids such as glycine, alanine, serine, cysteine, and threonine. However, the systemic transport system L cannot be explained only by these two types transporters of the transport system L, and therefore, existence of an unidentified isoform of transport system L has been expected.

The known transport system L transporters of LAT1 and LAT2 are heterodimeric proteins belonging to SLC7 family, and form functional transporters by coupling with 4F2hc which is a protein having single transmembrane structure. In the already disclosed mouse and human genomic database, a functionally unidentified member of SLC7 family was searched, but any additional transporter corresponding to the transport system L was not found. Therefore, unidentified new transport system L transporter has been supposed to be a protein other than the SLC7 family.

Further, as analogous proteins to the neutral amino acid transporter LAT1, $y^+LAT1$ and $y^+LAT2$, which have a function of transport system $y^+L$ to transport neutral and basic amino acids, have been cloned (Torrents et al., The Journal of Biological Chemistry, Vol. 273, No. 49, 32437-32445 (1998)). In addition, it was demonstrated that both of $y^+LAT1$ and $y^+LAT2$ functioned only in the coexistence with a complementary factor 4F2hc. Both of $y^+LAT1$ and $y^+LAT2$ principally transport glutamine, leucine and isoleucine as neutral amino acids, and have narrow substrate selectivity for the neutral amino acid.

In addition, as an aromatic amino acid transporter, TAT1, which corresponds to transport system T, has been cloned (Kim et al., The Journal of Biological Chemistry, Vol. 276, No. 20, 17221-17228 (2001)). The TAT1 transports aromatic amino acids such as tryptophan, tyrosine and phenylalanine $Na^+$-independently, but does not transport blanched amino acids such as leucine, isoleucine and valine. TAT1 is not inhibited by BCH, which is a specific inhibitor of the transport system L, and thus, the TAT1 is distinct from the amino acid transport system L.

The references of the prior art with respect to the present application of the invention are as follows;

1. Christensen, Physiological Reviews, Vol. 70, No. 1, 43-77 (1990)
2. Kanai, Current Opinion in Cell Biology, Vol. 9, No. 4, 565-572 (1997)
3. Amara and Kuhar, Annual Review of Neuroscience, Vol. 16, 73-93 (1993)
4. Palacin, The Journal of Experimental Biology, Vol. 196, 123-137 (1994)
5. Kanai et al., The Journal of Biological Chemistry, Vol. 273, No. 37, 23629-23632 (1999)
6. Segawa et al., The Journal of Biological Chemistry, Vol. 274, No. 28, 19745-19751 (1999)

7. Torrents et al., The Journal of Biological Chemistry, Vol. 273, No. 49, 32437-32445 (1998)
8. Kim et al., The Journal of Biological Chemistry, Vol. 276, No. 20, 17221-17228 (2001)
9. Cole et al., Genomics, Vol. 51, No. 2, 282-287 (1998)

DISCLOSURE OF INVENTION

It is an object of the present invention to provide an amino acid transporter capable of sodium-independently transporting branched amino acids as a single molecule and exhibiting a function of transport system L, and a gene encoding the transporter. Further objects of the present invention will be obvious from the description below.

BRIEF DESCRIPTION OF THE DRAWINGS

FIG. 2 shows a comparison of amino acid sequences between human LAT3 (SEQ ID NO: 2) and mouse LAT3 (SEQ ID NO: 3). Expected transmembrane domains are indicated with a line. Also, expected glycosylation sites are indicated by #, expected protein kinase C depending phosphorylation sites are indicated by *, and expected tyrosine phosphorylation site is indicated by &.

FIG. 3 is a photograph instead of a drawing, showing the expression levels of mRNA of LAT3 gene in various human organ tissues analyzed by Northern blotting.

$R^1$—$CH(NH_2)COOH$, L-leucine; $R^1$—$CH(NH_2)CH_2OH$, L-leucinol; $R^1$—$CH_2NH_2$, isopentylamine; $R^1$—$CH_2COOH$, 4-methylvaleric acid; $R^1$—$CH(NH_2)CH_3$, 1,3-dimethyl-n-butylamine; $R^1$—$CH(NH_2)CONH_2$, L-leucinamide; $R^1$—$CH(NH_2)COOCH_3$, L-leucine-methylester; $R^1$—$CH(NHCOCH_3)COOH$, N-acetyl-L-leucine; $R^1$—$CH(NHCH_3)COOH$, N-methyl-L-leucine; $R^2$—$CH(NH_2)COOH$, L-valine; $R^2$—$CH(NH_2)CH_2OH$, L-valinol; $R^2$—$CH_2NH_2$, isobutylamine; $R^2$—$CH_2COOH$, isovaleric acid; $R^3$—$CH(NH_2)COOH$, L-phenylalanine; $R^3$—$CH(NH_2)CH_2OH$, L-phenylalaninol; $R^3$—$CH_2NH_2$, 2-phenylethylamine; $R^3$—$CH_2COOH$, 3-phenylpropionic acid; $R^4$—$CH(NH_2)$ COOH, L-tyrosine; $R^4$—$CH(NH_2)CH_2OH$, L-tyrosinol; $R^4$—$CH_2NH_2$, tyramine; $R^4$—$CH_2COOH$, 3-(p-hydroxyphenyl)propionic acid.

Figure 11:
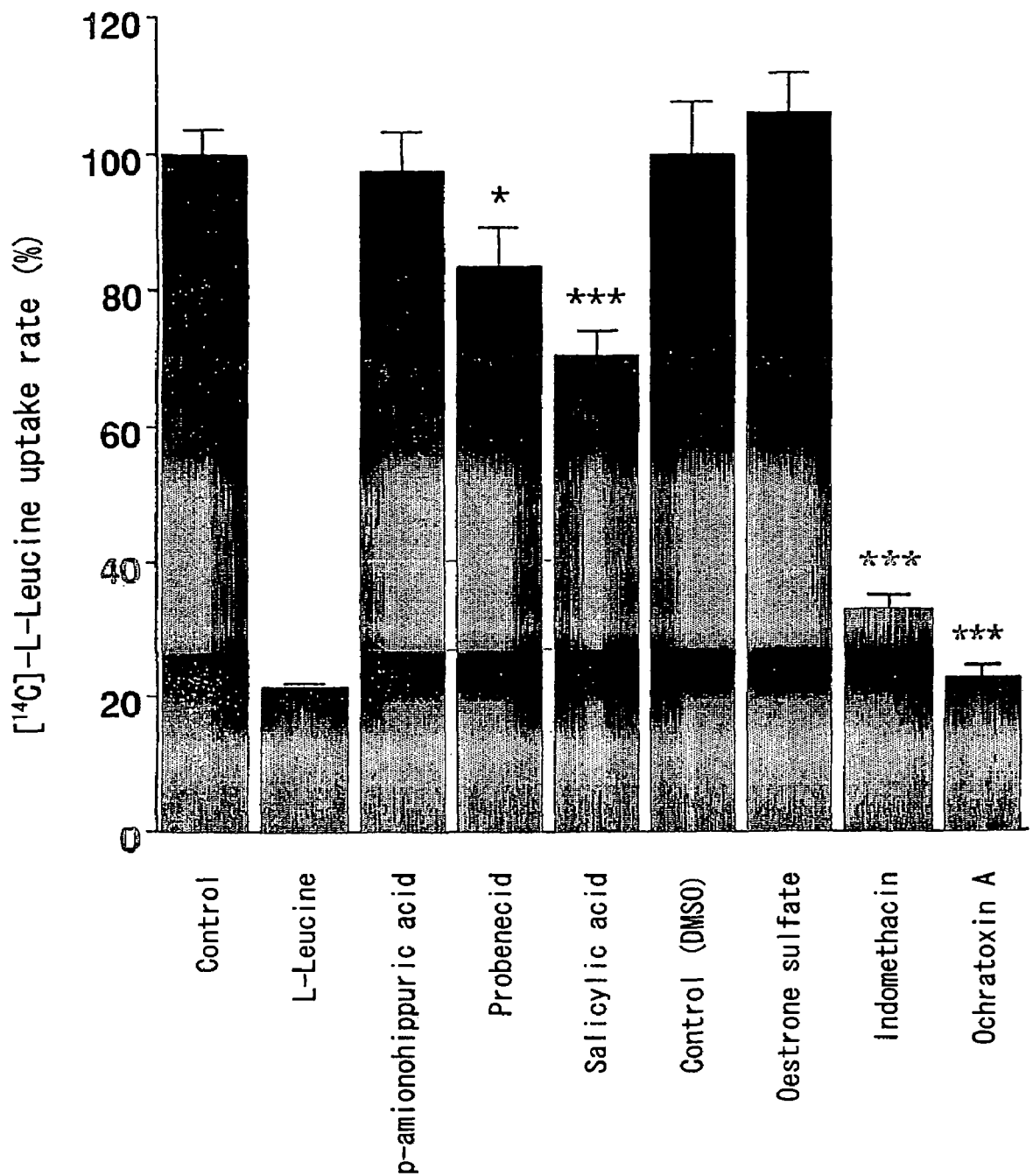

FIG. 11 shows influences of various anionic compounds added in the system on the leucine uptake by the oocytes injected with cRNA of human LAT3 gene.

Figure 12:
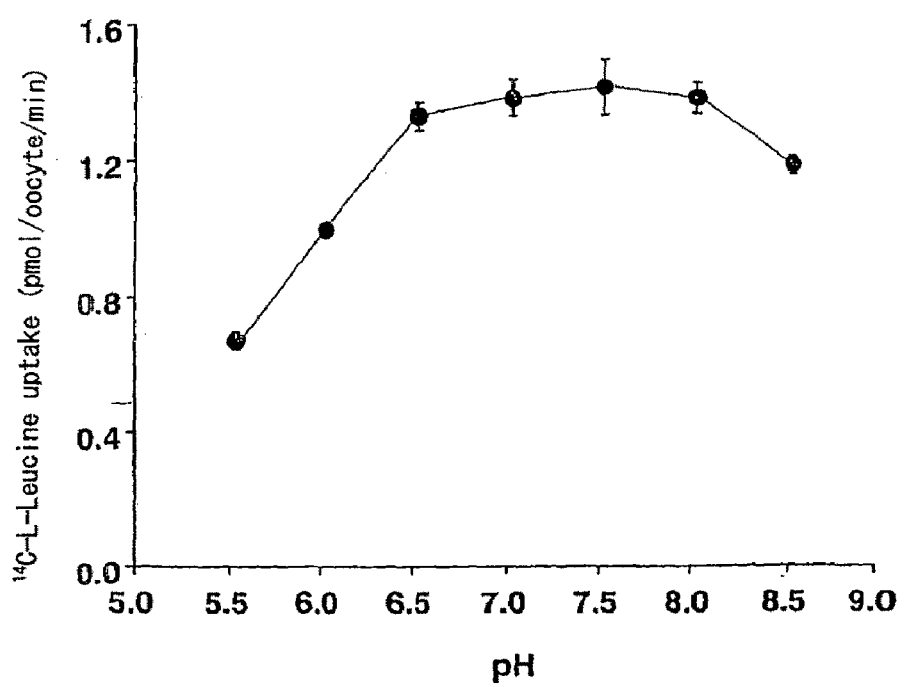

FIG. 12 shows uptakes of radio-labeled L-amino acids and L-amino acids by the oocytes injected with cRNA of human LAT3 gene.

Figure 13:
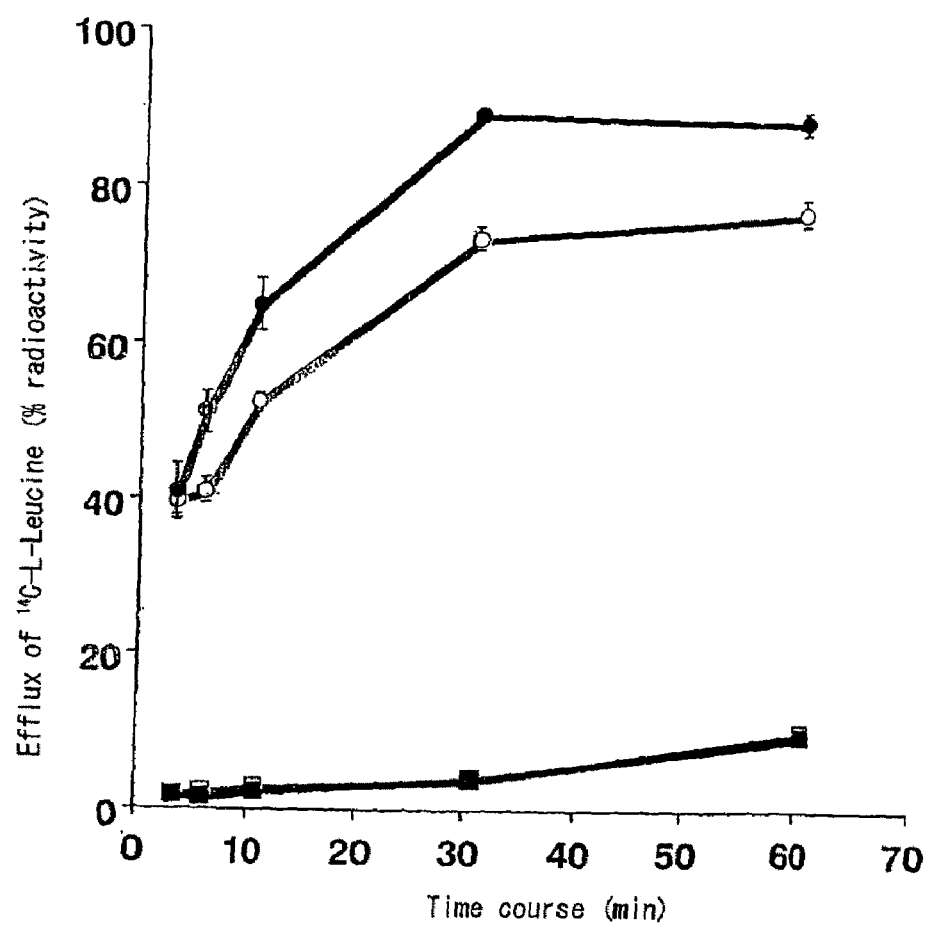

FIG. 13 shows infouences of pH on the leucine uptake by the oocytes injected with cRNA of human LAT3 gene.

FIG. 14 shows time course of the $^{14}C$-leucine efflux by the oocytes injected with cRNA of human LAT3 gene. □: $^{14}C$-leucine efflux by the oocytes injected with water instead of cRNA of human LAT3 gene as a control, in the case of a leucin-absent and Na$^+$-free uptake solution. ■: $^4C$-leucine efflux by the oocytes injected with water instead of cRNA of human LAT3 gene as a control, in the case of a leucin-present and Na$^+$-free uptake solution. ○: $^{14}C$-leucine efflux by the oocytes injected with cRNA of human LAT3 gene, in the case of a leucin-absent and Na$^+$-free uptake solution. ●: $^{14}C$-leucine efflux by the oocytes injected with the cRNA of the human LAT3 gene, in the case of a leucin-present and Na$^+$-free uptake solution. The vertical axe indicates percentage (%) of the radioactivity of efflux to the radioactivity injected into $^{14}C$-leucine.

FIG. 15 shows influences of N-ethylmaleimide (NEM) treatment on the leucine uptake by the oocytes injected with the cRNA of the human LAT3 gene.

Figure 16:
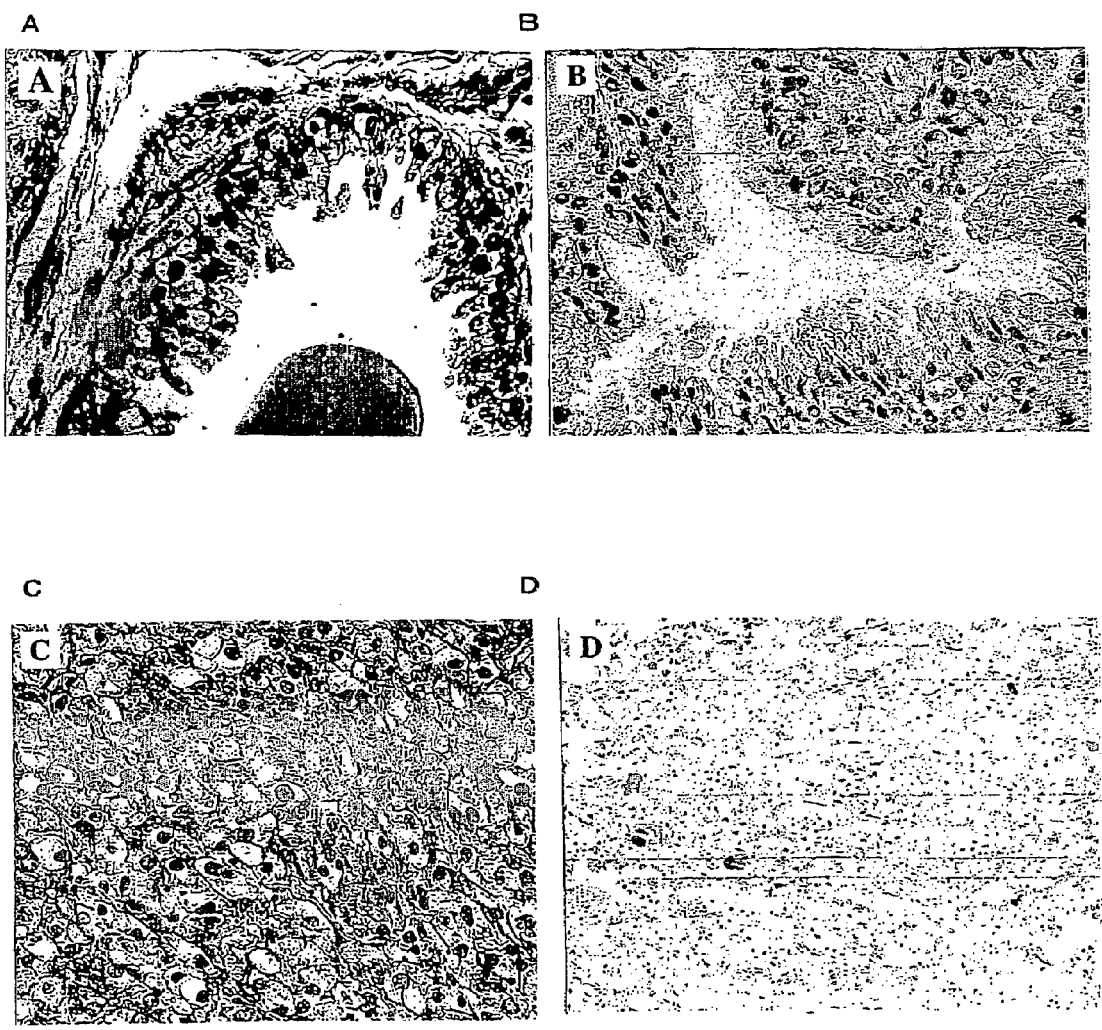

FIG. 16 is a photograph showing results of immunohistochemical analyses of the LAT3 in human prostate carcinoma (A and B) and human renal carcinoma (C and D) using anti-LAT3 antibody. A and C: staining by the anti-LAT3 antibody. B and D: absorption tests using an antigen peptide.

FIG. 17 shows a comparison of amino acid sequences between human LAT3 (SEQ ID NO: 2) and human LAT4 (SEQ ID NO: 6).

FIG. 18 shows a comparison of amino acid sequence between human LAT4 (SEQ ID NO: 6) and mouse LAT4 (SEQ ID NO: 8). Expected transmembrane sites are indicated with a line. Also, expected glycosylation sites are indicated by #; cAMP depending phosphorylation site is by +; and protein kinase C depending phosphorylation sites are by *.

Figure 19:
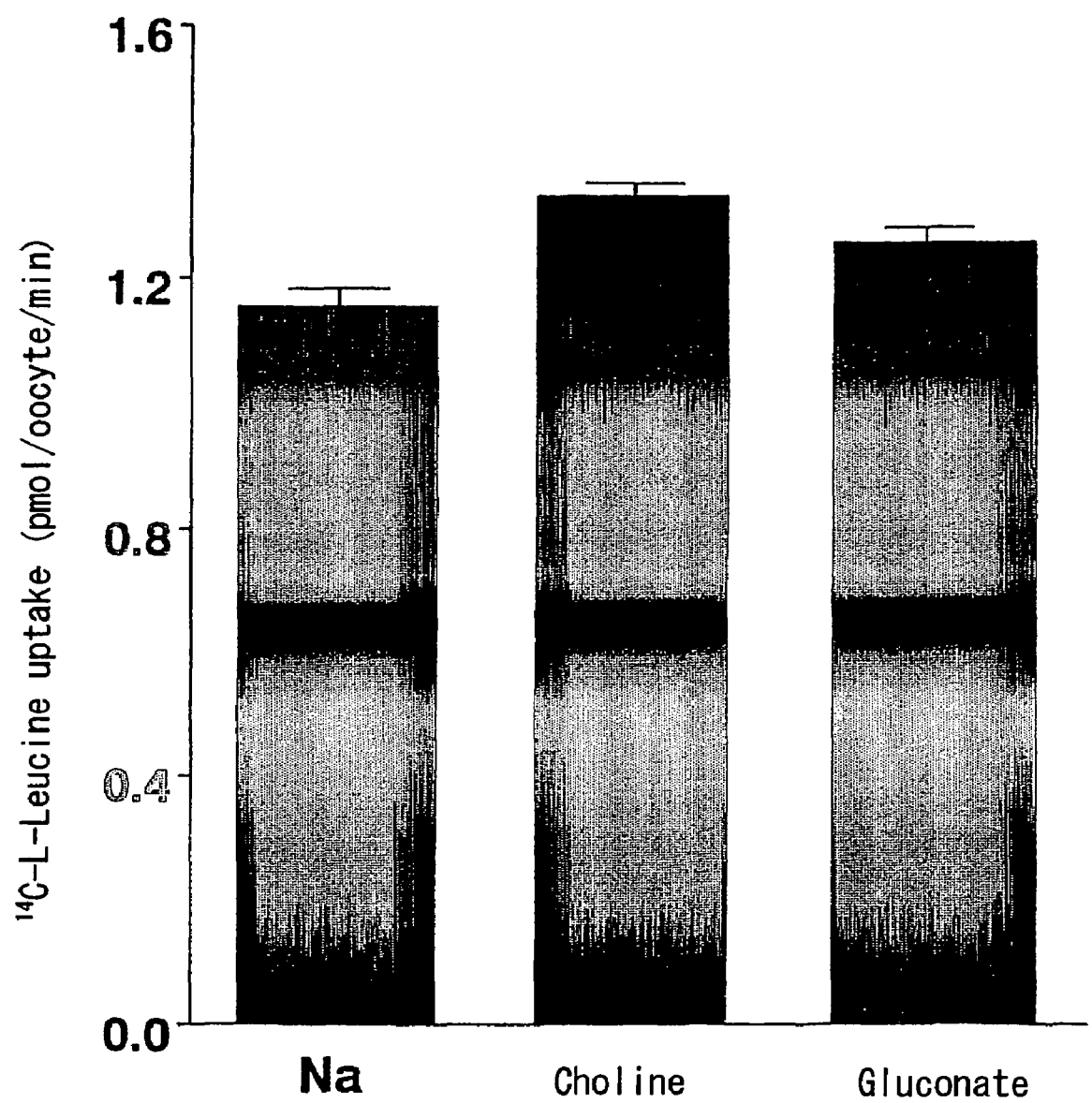

FIG. 19 shows influences of salts to be added on the leucine uptake by the oocytes injected with cRNA of mouse LAT4 gene.

Figure 20:
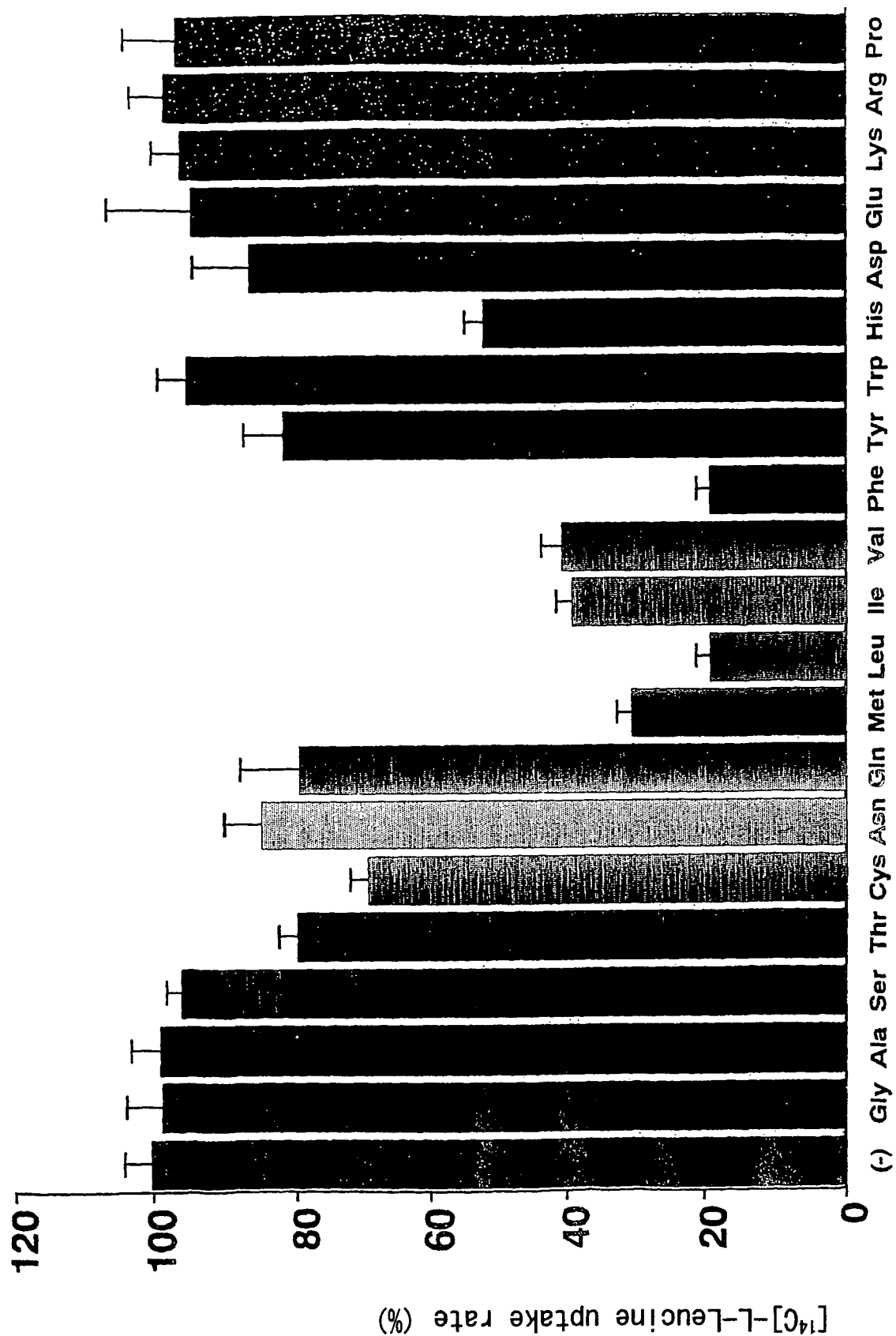

FIG. 20 shows influences of glycine and various L-amino acids on the leucine uptake by the oocytes injected with the cRNA of mouse LAT4 gene.

Figure 21:
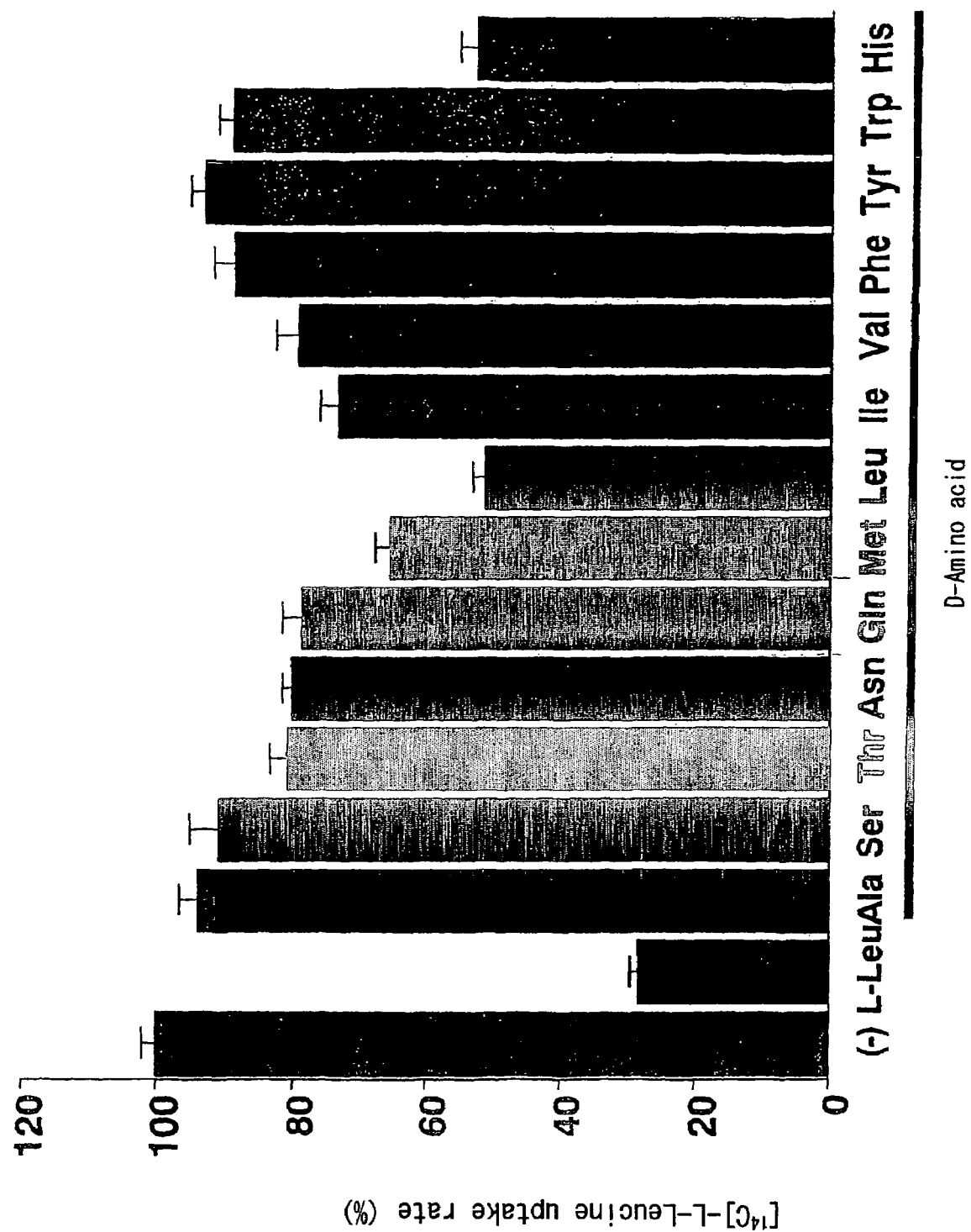

FIG. 21 shows influences of various D-amino acids on the leucine uptake by the oocytes injected with the cRNA of mouse LAT4 gene.

Figure 22:
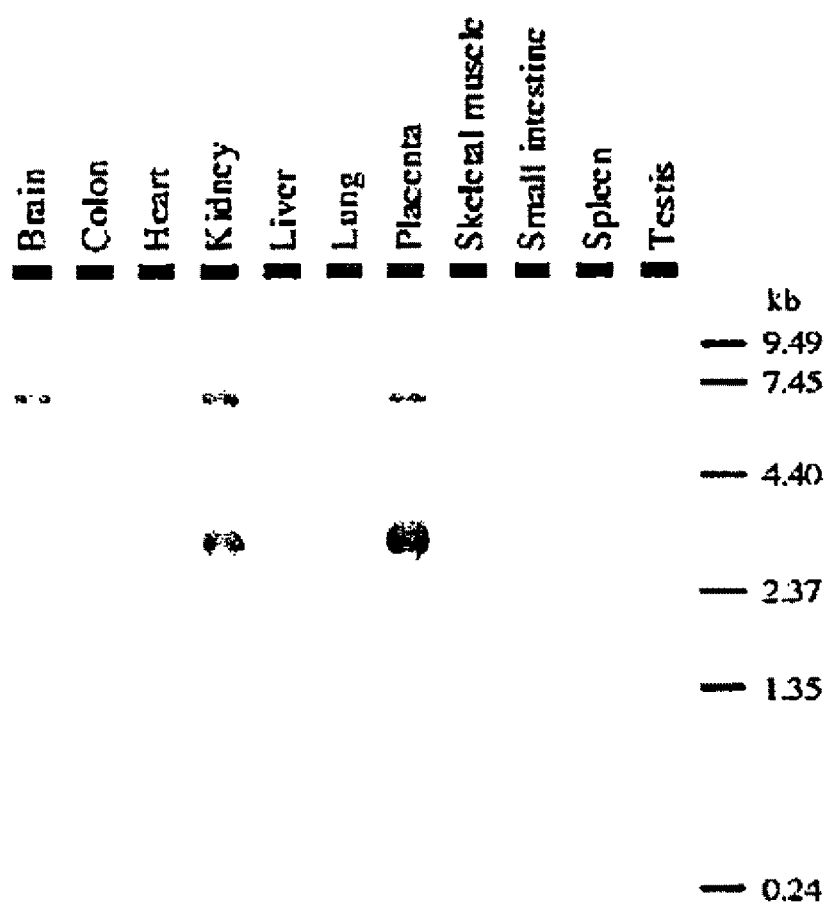

FIG. 22 shows influences of various selective inhibitors against the amino acid transport system on the leucine uptake by the oocytes injected with the cRNA of mouse LAT4 gene.

Figure 23:
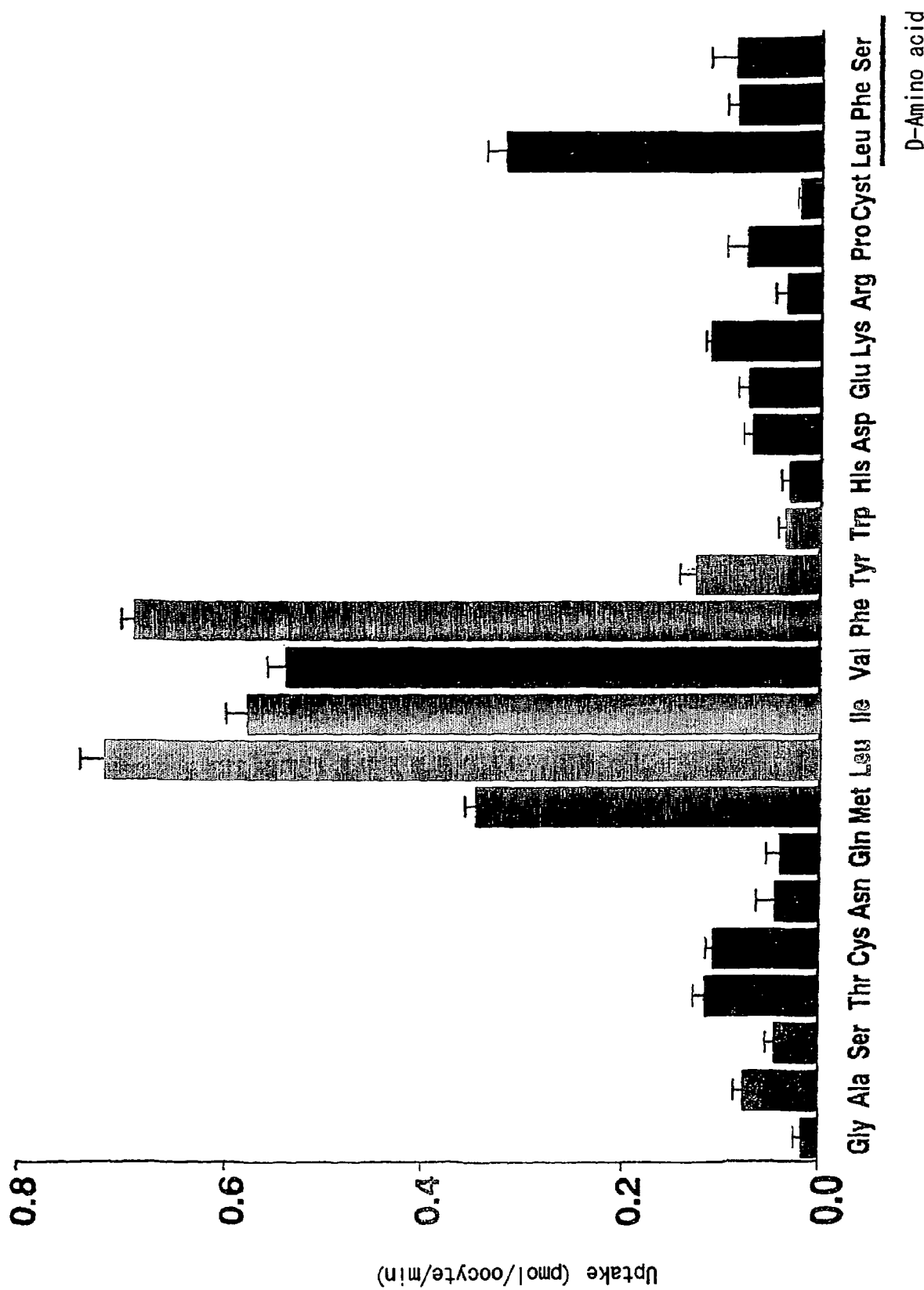

FIG. 23 shows uptake of radio-labeled L-amino acids and L-amino acids by the oocytes injected with the cRNA of mouse LAT4 gene.

Figure 24:
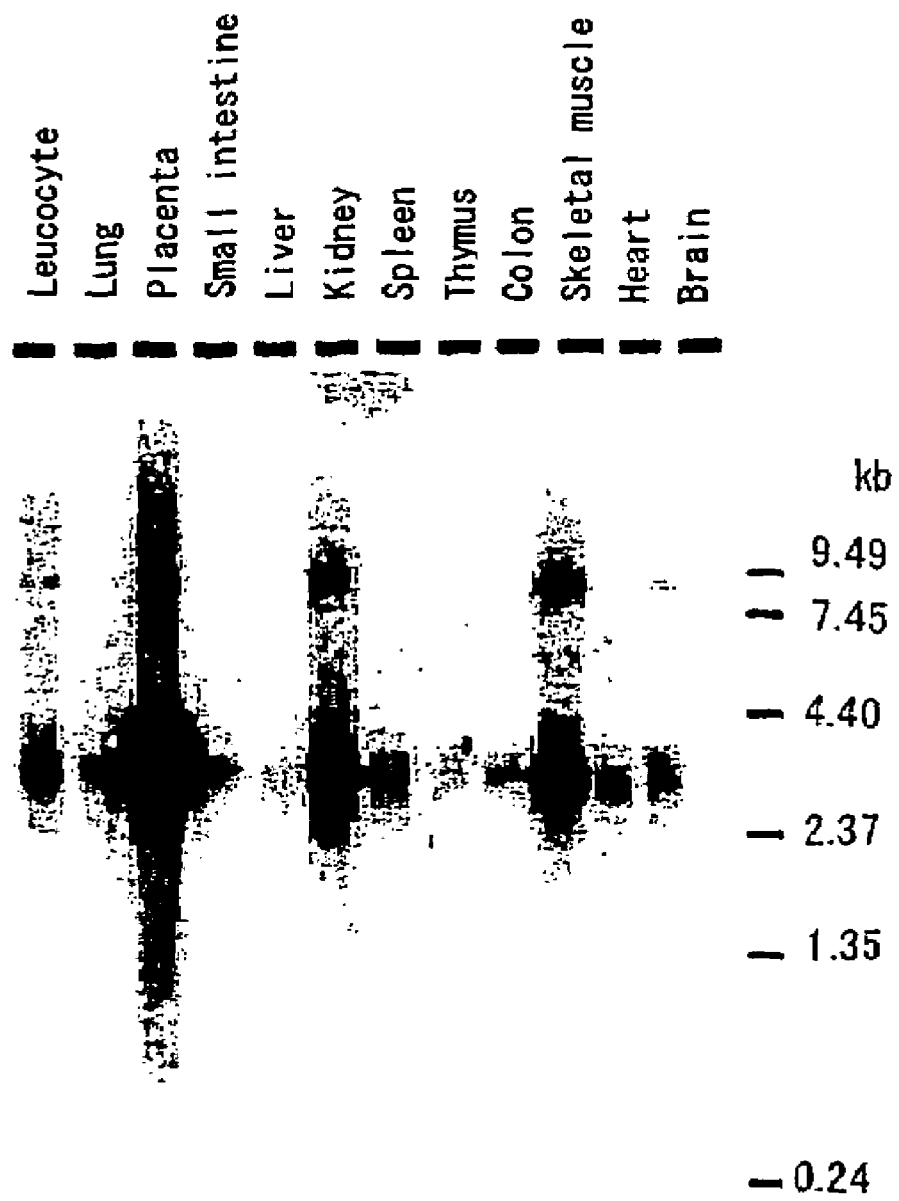

FIG. 24 is a photograph instead of a drawing, showing the expression levels of LAT4 gene mRNA in the various human organ tissues as a result of Northern blotting analysis.

Figure 25:
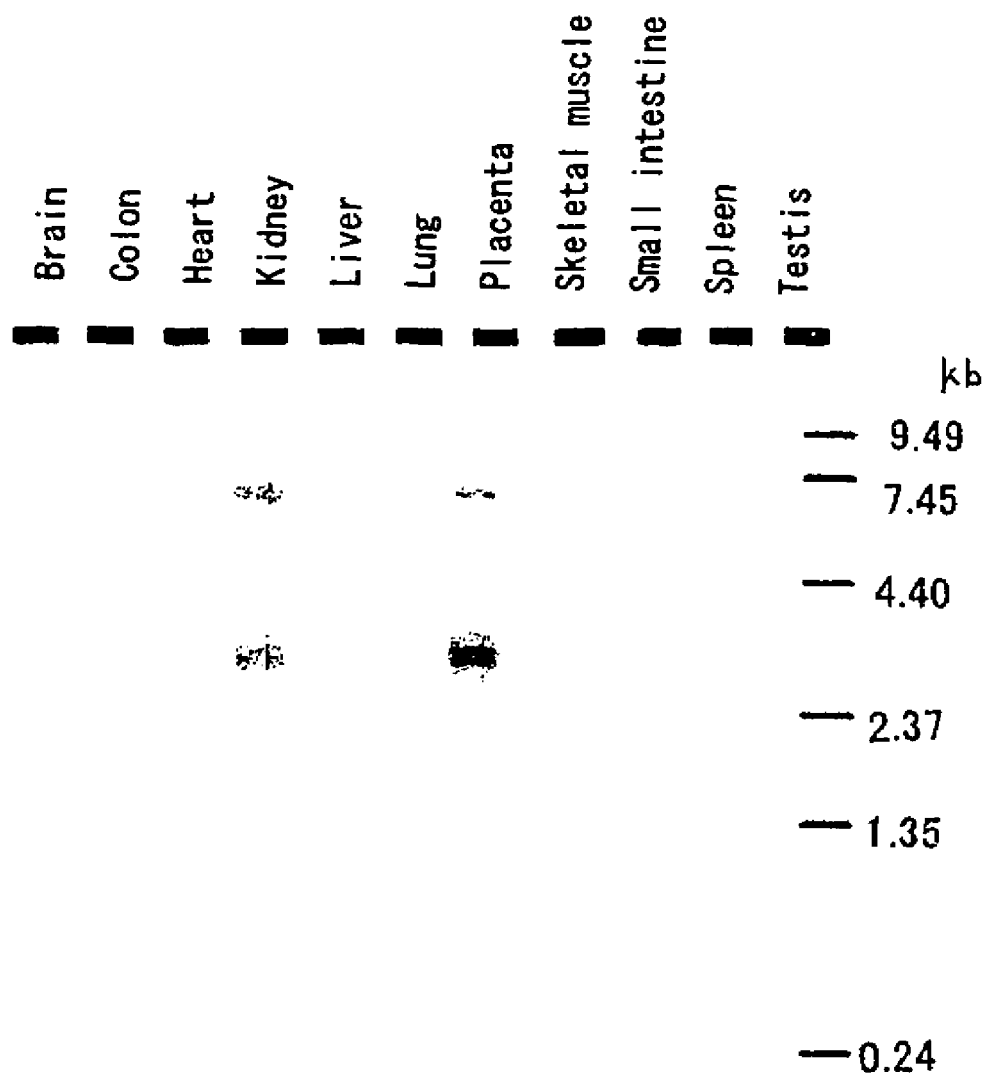

FIG. 25 is a photograph instead of a drawing, showing the expression levels of LAT4 gene mRNA in the various mouse organ tissues as a result of Northern blotting analysis.

BEST MODE FOR CARRYING OUT THE INVENTION

The present inventors have performed expression cloning using expression system of *Xenopus laevis* oocytes and poly (A)⁺RNA extracted from a human hepatoma cell line FCL4 as a starting material, and cloned a gene for a novel transporter having properties of the transporter system L and exhibiting a capability of transporting branched neutral amino acids as a single molecule. Further, the other genes having similar sequences were identified using EST (expressed sequence tag) database. These genes were expressed using *Xenopus* oocytes and the functional properties of the gene products were clarified, and thus the present invention was completed.

Namely, the present invention provides a protein capable of sodium-independently transporting branched neutral amino acids and analogs thereof as a single molecule, wherein said protein is selected from the following (A) to (H):
(A) a protein consisting of an amino acid sequence represented by SEQ ID NO: 2;
(B) a protein consisting of an amino acid sequence represented by SEQ ID NO: 4;
(C) a protein consisting of an amino acid sequence represented by SEQ ID NO: 6;
(D) a protein consisting of an amino acid sequence represented by SEQ ID NO: 8;
(E) a protein consisting of an amino acid sequence derived from an amino acid sequence represented by SEQ ID NO: 2 by deletion, substitution or addition of one to several amino acids;
(F) a protein consisting of an amino acid sequence derived from an amino acid sequence represented by SEQ ID NO: 4 by deletion, substitution or addition of one to several amino acids;
(G) a protein consisting of an amino acid sequence derived from an amino acid sequence represented by SEQ ID NO: 6 by deletion, substitution or addition of one to several amino acids; and
(H) a protein consisting of an amino acid sequence derived from an amino acid sequence represented by SEQ ID NO: 8 by deletion, substitution or addition of one to several amino acids.

In addition, the present invention provides a gene consisting of a DNA encoding a protein capable of sodium-independently transporting branched neutral amino acids and analogs thereof as a single molecule, wherein said gene is selected from the following (a) to (h):
(a) a DNA consisting of a base sequence represented by SEQ ID NO: 1;
(b) a DNA consisting of a base sequence represented by SEQ ID NO: 3;
(c) a DNA consisting of a base sequence represented by SEQ ID NO: 5;
(d) a DNA consisting of a base sequence represented by SEQ ID NO: 7;
(e) a DNA hybridizable under stringent condition with a DNA consisting of a base sequence represented by SEQ ID NO: 1;
(f) a DNA hybridizable under stringent condition with a DNA consisting of a base sequence represented by SEQ ID NO: 3;
(g) a DNA hybridizable under stringent condition with a DNA consisting of a base sequence represented by SEQ ID NO: 5; and
(h) a DNA hybridizable under stringent condition with a DNA consisting of a base sequence represented by SEQ ID NO: 7.

The amino acid sequence represented by SEQ ID NO: 2 denotes an amino acid sequence (559 amino acids) of an amino acid transporter (human LAT3), which is derived from a human hepatoma cell line FLC4 and capable of sodium-independently transporting branched neutral amino acids and analogs thereof as a single molecule. The base sequence of cDNA encoding the relevant transporter is represented by SEQ ID NO: 1.

The amino acid sequence represented by SEQ ID NO: 4 denotes an amino acid sequence (564 amino acids) of an amino acid transporter (mouse LAT3), which is derived from the mouse salivary gland and capable of sodium-independently transporting branched neutral amino acids and analogs thereof as a single molecule. The base sequence of cDNA encoding the relevant transporter is represented by SEQ ID NO: 3.

The amino acid sequence represented by SEQ ID NO: 6 denotes an amino acid sequence (573 amino acids) of an amino acid transporter (human LAT4), which is derived from a human fetal brain and capable of sodium-independently transporting branched neutral amino acids and analogs thereof as a single molecule. The base sequence of cDNA encoding the relevant transporter is represented by SEQ ID NO: 5.

The amino acid sequence represented by SEQ ID NO: 8 denotes an amino acid sequence (568 amino acids) of an amino acid transporter (mouse LAT4), which is derived from a mouse kidney and capable of sodium-independently transporting branched neutral amino acids and analogs thereof as a single molecule. The base sequence of cDNA encoding the relevant transporter is represented by SEQ ID NO: 7.

The proteins of the present invention capable of sodium-independently transporting branched neutral amino acids and analogs thereof as a single molecule, namely, an amino acid transporter LAT3 (L-type amino acid transporter 3) and LAT4 (L-type amino acid transporter 4), have an ability to transport (uptake) selectively branched amino acids such as leucine, isoleucine and valine, and neutral amino acids typified by phenylalanine.

The transport of neutral amino acid mediated by the amino acid transporter LAT3 of the present invention, capable of sodium-independently transporting branched neutral amino acids and analogs thereof as a single molecule, is strongly inhibited by a branched amino acid alcohol and phenylalaninol. Also, the transport of a neutral amino acid mediated by the LAT3 is inhibited by N-ethylmaleimide.

The amino acid transporter LAT3 of the present invention capable of sodium-independently transporting branched neutral amino acids and analogs thereof as a single molecule, is expressed strongly in a pancreas, a liver, a skeletal muscle, a heart, a bone marrow and fetal liver, and weakly in a kidney, a placenta, a lung, a small intestine, an ovary, a testis, a prostate and a spleen, in the human body.

Also, the amino acid transporter LAT4 of the present invention capable of sodium-independently transporting branched neutral amino acids and analogs thereof as a single molecule is expressed strongly in a placenta, a kidney, a skeletal muscle, a brain, a heart, a spleen, a lung, a leucocyte and a small intestine, and weakly in a liver and a thymus, in the human body.

The present invention relates to use of the amino acid transporter capable of sodium-independently transporting branched neutral amino acids and analogs thereof as a single molecule, and the gene encoding the relevant amino acid transporter.

Namely, the present invention provides a plasmid which comprises a gene encoding the amino acid transporter capable of sodium-independently transporting branched neutral amino acids and analogs thereof as a single molecule or a gene encoding a protein contained in the aforementioned gene, a nucleotide which comprises a partial sequence of not less than 14 consecutive bases of a gene encoding the amino acid transporter capable of sodium-independently transporting branched neutral amino acids and analogs thereof as a single molecule or the complementary base sequence to the aforementioned partial base sequence, and an antibody specific for the amino acid transporter capable of sodium-independently transporting branched neutral amino acids and analogs thereof as a single molecule.

The present invention provides a method for detecting an activity of a specimen as a substrate or an inhibitor for a capability of sodium-independently transporting branched neutral amino acids and analogs thereof possessed by an amino acid transporter capable of sodium-independently transporting branched neutral amino acids and analogs thereof as a single molecule, using said protein.

The present invention further provides a method for modifying in vivo kinetics of drugs, toxic substances or extraneous substances being transported by the amino acid transporter capable of sodium-independently transporting branched neutral amino acids and analogs thereof as a single molecule, or a method for modifying the in vivo kinetics or metabolism of the branched neutral amino acids being transported by the aforementioned amino acid transporter, by modulating capability of the aforementioned amino acid transporter to transport the branched neutral amino acids or analogs thereof and controlling growth of normal or tumor cells, using the aforementioned amino acid transporter, specific antibody for the aforementioned amino acid transporter, enhancer or suppressor of the function of the aforementioned amino acid transporter, or antisense nucleotide of the gene encoding the aforementioned amino acid transporter.

The protein of the present invention capable of sodium-independently transporting branched neutral amino acids and analogs thereof as a single molecule includes proteins having amino acid sequence represented by SEQ ID NO: 2, 4, 6 or 8 in the sequence listing described later.

A protein with an amino acid sequence represented by SEQ ID NO: 2 is an amino acid transporter (human LAT3) derived from a human hepatoma cell line FLC4 capable of sodium-independently transporting branched neutral amino acids and analogs thereof as a single molecule.

A protein with an amino acid sequence represented by SEQ ID NO: 4 is an amino acid transporter (mouse LAT3) derived from a mouse salivary gland capable of sodium-independently transporting branched neutral amino acids and analogs thereof as a single molecule.

A protein with an amino acid sequence represented by SEQ ID NO: 6 is an amino acid transporter (human LAT4) derived from a human fetal brain capable of sodium-independently transporting branched neutral amino acids and analogs thereof as a single molecule.

A protein with an amino acid sequence represented by SEQ ID NO: 8 is an amino acid transporter (mouse LAT4) derived from a mouse kidney capable of sodium-independently transporting branched neutral amino acids and analogs thereof as a single molecule.

In the proteins of the present invention, in addition to the above mentioned proteins, for example, a protein consisting of an amino acid sequence derived from an amino acid sequence represented by SEQ ID NO: 2, 4, 6 or 8 by deletion, substitution or addition of one to several amino acids are included. The extent of deletion, substitution or addition of amino acid in the amino acid sequence may be within a range in which the activity of amino acid transport is not deteriorated.

As for SEQ ID NO: 2, the modification of amino acid is generally 1 to about 111, preferably 1 to about 56; as for SEQ ID NO: 4, generally 1 to about 113, preferably 1 to about 57; as for SEQ ID NO: 6, generally 1 to about 115, preferably 1 to about 57; and as for SEQ ID NO: 8, generally 1 to about 114, preferably 1 to about 57. Such proteins may have 1 to 80%, preferably 1 to 90% of amino acid sequence homology with the amino acid sequences represented by SEQ ID NO: 1 and SEQ ID NO: 2.

The amino acid sequence represented by SEQ ID NO: 2 was identical with POV1, which has been expressed in high level in human prostate carcinoma and reported as a functionally unidentified sequence (Cole et al., Genomics, Vol. 51, No. 2, 282-287 (1998)). The amino acid sequences represented by SEQ ID NO: 4, 6 and 8 have not been reported, and supposed to be new ones.

A gene encoding the protein capable of sodium-independently transporting branched neutral amino acids and analogs thereof as a single molecule includes genes having base sequences represented by SEQ ID NO: 1, 3, 5 and 7 in the sequence listing described later.

The base sequence represented by SEQ ID NO: 1 shows a base sequence (about 2.5 kbp) of a whole-length cDNA of a gene encoding an amino acid transporter (human LAT3) derived from a human hepatoma cell line FLC4 capable of sodium-independently transporting branched neutral amino acids and analogs thereof as a single molecule.

The base sequence represented by SEQ ID NO: 3 shows a base sequence (about 2.5 kbp) of a whole-length cDNA of a gene encoding an amino acid transporter (mouse LAT3) derived from a mouse salivary gland capable of sodium-independently transporting branched neutral amino acids and analogs thereof as a single molecule.

The base sequence represented by SEQ ID NO: 5 shows a base sequence (about 3.3 kbp) of a whole-length cDNA of a gene encoding an amino acid transporter (human LAT4) derived from a human fetal brain capable of sodium-independently transporting branched neutral amino acids and analogs thereof as a single molecule.

The base sequence represented by SEQ ID NO: 7 shows a base sequence (about 3.2 kbp) of a whole-length cDNA of a gene encoding an amino acid transporter (mouse LAT4) derived from a mouse kidney capable of sodium-independently transporting branched neutral amino acids and analogs thereof as a single molecule.

The gene of the present invention includes, other than the above mentioned genes, a gene containing a DNA hybridizable under stringent condition with a DNA consisting of a base sequence represented by SEQ ID NO: 1, 3, 5 or 7. The DNA hybridizable in this way may be a DNA, which codes a protein capable of transporting neutral amino acids. Such DNA may have generally 70% or higher, preferably 80% or higher of sequence homology with the base sequence represented by SEQ ID NO: 1, 3, 5 or 7. Such DNA includes, for example, naturally transformed variant genes, artificially transformed variant genes, and homologous genes derived from heterologous organisms.

In the present invention, the hybridization under the stringent condition may be carried out in 5×SSC or in the solution for hybridization with the same salt concentration at 37 to 42° C. for about 12 hours, then preliminary washing with 5×SSC or a solution with the same salt concentration is carried out if needed, and followed by washing in a 1×SSC or a solution with the same salt concentration.

A gene encoding amino acid transporter of the present invention capable of sodium-independently and selectively transporting branched neutral amino acids and analogs thereof as a single molecule may be obtained by screening of appropriate mammalian tissues or cells as the source of gene. Mammal includes non human animals such as a dog, a caw, a horse, a goat, a sheep, a monkey, a pig, a rabbit, a rat and a mouse, and a human as well.

Screening and isolation of a gene may be carried out preferably by the expression cloning method or the like.

For example, a mRNA (poly(A)$^+$RNA) is prepared using human hepatoma cell line FLC4 as a source of gene. The mRNA prepared is size fractionated, and each fraction is injected into *Xenopus* oocytes. As to the oocytes injected with mRNA, for example, leucine is applied as a substrate, and the transport (uptake) of substrate into the cells is measured. The mRNA of LAT3 may be concentrated by selecting mRNA fractions showing high uptake activity. The cDNA library is prepared using the concentrated mRNA. About 500 clones of cDNA in the library are pooled as one group, and cRNA (capped) for each group are prepared, and the cRNA of each group is injected into the oocytes, and the positive group of substrate-uptake activity is selected. The positive group is further divided into subgroups and the same procedures as above are repeated, and thus a clone containing cDNA of the LAT3 gene may be obtained.

Also, isolation of cDNA of the LAT4 gene may be performed preferably by the homology cloning method, or the like.

For example, using a human fetal brain or a mouse kidney as a source of gene, mRNA (poly(A)$^+$RNA) is prepared, and then cDNA library is prepared using the mRNA. A clone containing cDNA of the LAT4 gene may be obtained by screening of the cDNA library using a probe corresponding to the homologous sequence of LAT3 (for example, Gen-Bank™/EBI/DDBJ accession No. AW162917) obtained by searching EST (expressed sequence tag) database.

As to the cDNA obtained, base sequence is determined by the conventional method, and the open reading frame is analyzed, so that the amino acid sequence of the protein encoded thereby, namely LAT3 or LAT4, is determined.

The fact that the cDNA obtained is a cDNA of the gene encoding amino acid transporter capable of sodium-independently and selectively transporting branched neutral amino acids as a single molecule, namely the gene product encoded by the cDNA obtained is the amino acid transporter capable of sodium-independently and selectively transporting branched neutral amino acids as a single molecule may be verified, for example, by the following procedure. That is, the complementary RNA (cRNA, capped) prepared based on the cDNA of LAT3 gene or LAT4 gene is injected and expressed in the oocytes, after that the capability of transporting (uptake) branched neutral amino acids into the cell is measured according to the generally used uptake test (Kanai and Hediger, Nature, Vol. 360, 467-471 (1992)) using appropriate branched neutral amino acid as the substrate, and thus the cDNA obtained may be verified.

Using the complementary RNA (cRNA) prepared based on the cDNA of LAT3 gene or LAT4 gene, LAT3 protein or LAT4 protein is synthesized by in vitro translation method (Hediger et al., Biochim. Biophys. Acta, Vol. 1064, Sec. 360 (1991)), and the synthesized protein may be subjected to the studies on the molecular size by electrophoresis, on the glycosylation whether existence or not, and so on.

The characteristics of LAT3 or LAT4, for example, the characteristics that the mode of amino acid transport by LAT3 is facilitatory diffusion type, and substrate selectivity and pH dependency of LAT3 or LAR 4, may be investigated by applying the similar uptake study using the expression cell.

A homologous gene derived from a different tissue or a different organism or a chromosomal gene or the like may be isolated by screening an appropriate cDNA library or a genomic DNA library prepared by a different source of gene using cDNA of LAT3 gene or LAT4 gene.

Also, a gene may be isolated from cDNA library or genomic library according to the conventional PCR (polymerase chain reaction) method using a synthetic primer designed based on the disclosed information of the base sequence of the gene (base sequence represented by SEQ ID NO: 1, 3, 5 or 7, or a part thereof) of the present invention.

DNA library such as cDNA library or genomic DNA library may be prepared, for example by the method described in the "Molecular cloning" (Sambrook, J., Fritsh, E. F. and Manitis, T., Cold Spring Harbor Press, 1989). Commercial DNA library may be used if it is available.

The amino acid transporter (LAT3 or LAT4) of the present invention capable of sodium-independently and selectively transporting branched neutral amino acids as a single molecule may be produced, for example, by recombinant DNA technology using a cDNA encoding thereof. For example, a DNA (cDNA or the like) encoding LAT3 or LAT4 is inserted into an appropriate expression vector, and the recombinant DNA obtained may be introduced into an appropriate host cell. The expression system (host-vector system) for polypeptide production includes, for example, the expression system of bacteria, yeast, insect cell and mammalian cell. Among them, insect cell and mammalian cell are preferable to use for the production of functional proteins.

For example, when a polypeptide is expressed in the mammalian cells, a DNA encoding the amino acid transporter LAT3 or LAT4 capable of sodium-independently and selectively transporting branched neutral amino acids as a single molecule is inserted into the down stream of an appropriate promoter (for example, cytomegalovirus promoter, SV40 promoter, LTR promoter, or elongation 1a promoter) in an appropriate expression vector (for example, adenovirus vector, retrovirus vector, papillomavirus vector, vaccinia virus vector, or SV40 vector), and thus an expression vector is constructed. In the next place, appropriate animal cells are transformed by the expression vector, and the transformant is cultured in an appropriate culture medium, and thus the objective polypeptide may be produced. A mammalian cell as the host cell includes a cell line such as monkey COS-7 cell, Chinese hamster CHO cell, human HeLa cell, or mouse S2 cell.

As a DNA encoding the amino acid transporter LAT3 or LAT4 capable of sodium-independently and selectively transporting branched neutral amino acids as a single molecule, a cDNA having the base sequence represented by SEQ ID NO: 1, 3, 5 or 7 may be used. Further, a DNA corresponding to the amino acid sequence may be designed without limitation to the above-described cDNA sequence, and used as a DNA encoding the polypeptide. In this case, each amino acid is known to have 1 to 6 coding codon and selection of codon to be used is optional. However, to achieve high expression efficiency the sequence may be designed by taking the frequency of codon usage of the host cell into account. A DNA having the designed base sequence may be obtained by chemical synthesis of DNA, by fragmentation or connection of the above mentioned cDNA, by partial modification of base sequence, or the like. Artificial partial modification or introduction of mutation may be achieved by the site-specific mutagenesis (Mark, D. F. et al., Proceedings of National Academy of Science, Vol. 81, Sec. 5662 (1984)) using a primer composed of a synthetic oligonucleotide encoding the desired modification.

Using the amino acid transporter of the present invention capable of sodium-independently and selectively transporting branched neutral amino acids as a single molecule or an immunologically homologous polypeptide thereto, an antibody against the aforementioned amino acid transporter may be obtained. The antibody may be used for detection or purification of the amino acid transporter capable of sodium-independently and selectively transporting branched neutral amino acids as a single molecule. The antibody may be produced using the amino acid transporter of the present invention capable of sodium-independently and selectively transporting branched neutral amino acids as a single molecule, fragments thereof, or synthetic peptides containing partial sequence thereof, or the like as the antigen. Polyclonal antibody may be produced by the conventional method of inoculation of the antigen into a host animal (for example, a rat or a rabbit) and recovery of immune serum, and monoclonal antibody may be produced by the conventional procedure such as hybridoma technique.

The amino acid transporter LAT3 or LAT4 of the present invention capable of sodium-independently and selectively transporting branched neutral amino acids as a single molecule, a gene thereof and the expression cell thereof may be used for in vitro experiment with regard to permeation efficiency of the membrane where the LAT3 or LAT4 exists, or at the site where the LAT3 or LAT4 is expected to exist. Also, the amino acid transporter LAT3 or LAT4 capable of sodium-independently and selectively transporting branched neutral amino acids as a single molecule, a gene thereof and the expression cells thereof may be used for developing compounds which pass through efficiently a membrane where the LAT3 or LAT4 exists, or at the site where the LAT3 or LAT4 is expected to exist. Further, the amino acid transporter LAT3 or LAT4 capable of sodium-independently and selectively transporting branched neutral amino acids as a single molecule, a gene thereof and the expression cells thereof may be used for in vitro experiment of drug interaction on a membrane where the LAT3 or LAT4 exists, or at the site where the LAT3 or LAT4 is expected to exist.

Repression of the amino acid transporter LAT3 or LAT4 of the present invention capable of sodium-independently and selectively transporting branched neutral amino acids as a single molecule may limit passing of specific compounds through the membrane where the LAT3 or LAT4 is expressed, or the site where the LAT3 or LAT4 is expected to exist.

The amino acid transporter LAT3 or LAT4 of the present invention capable of sodium-independently and selectively transporting branched neutral amino acids as a single molecule, a gene thereof and the expression cells thereof may be used for developing medical drugs (for example, a specific inhibitor against LAT3 or LAT4) which limit the membrane permeability of compounds transportable via the LAT3 or LAT4, or the permeability through the site where the LAT3 or LAT4 is expected to exist.

The amino acid transporter LAT3 or LAT4 of the present invention capable of sodium-independently and selectively transporting branched neutral amino acids as a single molecule, a gene thereof and the expression cells thereof may be used for the in vitro testing of the inhibitory effect by repression of the LAT3 or LAT4 on the cells which express LAT3 or LAT4 in high level. To repress LAT3 or LAT4, inhibitors, antisense oligo-DNA or a specific antibody may be used.

Also, using the amino acid transporter LAT3 or LAT4 of the present invention capable of sodium-independently and selectively transporting branched neutral amino acids as a single molecule, a gene thereof and the expression cell thereof, a functionary inhibiting agent or a monoclonal antibody having functionary inhibiting activity against LAT3 or LAT4, which can be used for inhibiting the growth of cells expressing LAT3 or LAT4 in high level such as tumor cells, may be developed.

In addition, the disclosure of JP-C-2003-062379 is incorporated herein in its entirety.

EXAMPLES

The present invention will be described in more detail using Examples, but the scope of the present invention should not be limited thereto.

Further, in the Examples described below, unless otherwise noted, all of the procedures were carried out in accordance with the methods described in the "Molecular cloning" (Sambrook, J., Fritsh, E. F. and Manitis, T., Cold Spring Harbor Press, 1989). When commercially available reagents or kits were used, they were used in accordance with the manufacturer's instructions.

Example 1

Cloning of Human cDNA of the Amino Acid Transporter LAT3 Capable of Sodium-Independently and Selectively Transporting Branched Neutral Amino Acids as a Single Molecule (1) Expression Cloning from a Human Hepatoma-Derived Cell Line FLC4

According to the method described by Kanai et al. (Kanai and Hediger, Nature, Vol. 360, 467-471 (1992)), the expression cloning was carried out as follows.

Four hundred (400) μg of poly(A)$^+$RNA derived from human hepatoma cell line FLC4 was size-fractionated by preparative gel electrophoresis.

Each fraction obtained by the above size fractionation was injected into *Xenopus laevis* oocytes, and cultured for 3 days.

The substrate uptake by the injected oocytes using leucine as a substrate was carried out according to the method described by Kanai et al. (Kanai and Hediger, Nature, Vol. 360, 467-471 (1992)), as follows. The oocytes was cultured for 30 minutes in the Na$^+$-free uptake solution (100 mM of choline chloride, 2 mM of potassium chloride, 1.8 mM of calcium chloride, 1 mM of magnesium chloride, 5 mM of HEPES, pH 7.4) using $^{14}$C-leucine (100 μM) as a substrate, and uptake rate of the substrate was measured by counting radioactivity in the cell. In this system, increased leucine uptake was observed in the oocytes injected with the poly(A)$^+$RNA derived from human hepatoma cell line FLC 4 compared with the oocytes injected with water as a control (FIG. 1).

Figure 1:
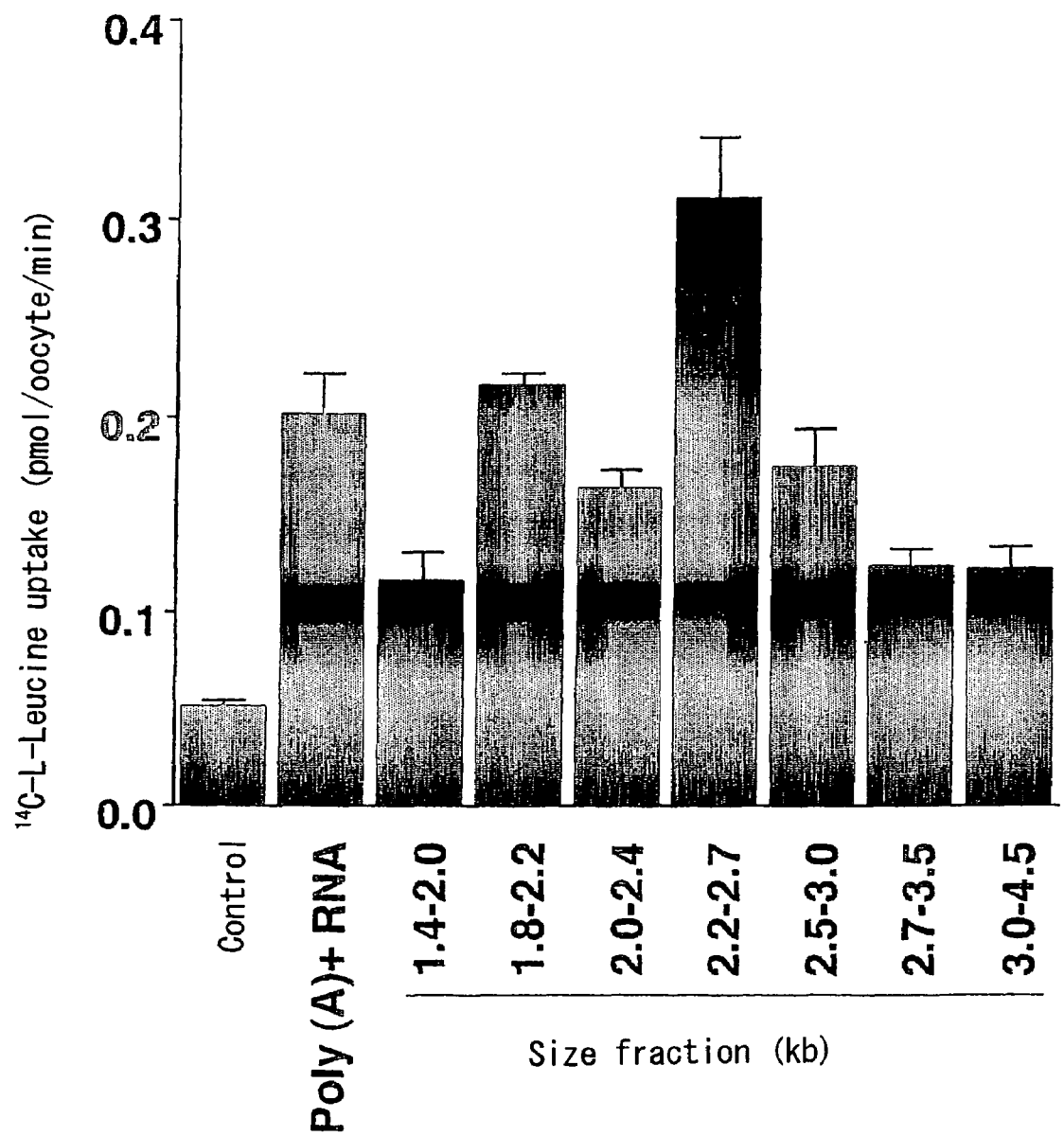
FIG. 1 shows experimental results of the leucine uptake by Xenopus oocytes injected with mRNA derived from human FLC4 cells and size fractions of the mRNA.

Among RNA fractions obtained by size fractionation, a fraction, which showed the highest uptake rate by the oocytes injected with RNA, was selected (FIG. 1). A cDNA library of the poly(A)$^+$RNA (2.2 to 2.7 kb) of the fraction was prepared using a kit for cDNA synthesis and cloning of plasmid (trade name: Superscript Plasmid System, GIBCO). The DNA was integrated into the restriction sites of SalI and NotI in the plasmid pSPORT 1 (GIBCO), and the recombinant plasmid prepared was introduced to a competent cell of *E. coli* DH10B strain (trade name: Electro Max DH10B Competent Cell, BIBCO). The transformant was cultured on a nitrocellulose membrane; about 500 colonies per one plate were obtained. From these colonies, plasmid DNA was prepared and cleaved by Not1 restriction enzyme. A capped cRNA was synthesized by in vitro transcription using the DNA prepared.

The cRNA obtained (about 50 ng) was injected into the oocytes. For the screening of positive clone, the experiment of leucine uptake by the oocytes was carried out by the same procedure described above. For the screening, groups of pooled DNA extracted from a plurality of clones were examined. When positive substrate-uptake was observed in one group, the group was further divided into a plurality of subgroups and further screening was carried out.

As to the clone obtained, that is, the clone containing a cDNA of human branched neutral amino acid transporter LAT3, base sequence of the cDNA was determined by the dye terminator cycle sequencing method (Applied Biosystems) using a synthetic primer for base sequence determination. Thus, the base sequence of human LAT3 gene was obtained. Also, by analyzing the base sequence of cDNA according to the general method, an open reading frame and an amino acid sequence of LAT3 encoded thereby were determined.

This sequence is shown as SEQ ID NO: 2 in the sequence listing described later.

Human LAT3 had an identical amino acid sequence with POV1, which has been expressed in high level in human prostate carcinoma and reported as a functionally unidentified sequence (Cole et al., Genomics, Vol. 51, No. 2, 282-287 (1998)).

From the result of analysis of amino acid sequence of LAT3 by means of the TopPred2 algorithm (Gunnar von Heijne, J. Mol. Biol., Vol. 225, 487-494 (1992)), 12 transmembrane domains (membrane-spanning domain) were expected as shown in FIG. 2. Moreover, a glycosylation site in the extracellular loop between transmembrane domains 1 and 2, two protein kinase C-dependent phosphorylation sites and a tyrosine phosphorylation site in the long intracellular loop between transmembrane domains 6 and 7, and a protein kinase-C dependent phosphorylation sites in the intracellular loop between transmembran domains 8 and 9 were predicted (FIG. 2).

(2) Expression of LAT3 Gene in Various Human Tissues (Analyzed by Northern Blotting)

A cDNA fragment corresponding to a base sequence of the 1790th to the 1936th in the human LAT3 gene was labeled with $^{32}$P-dCTP and used as a probe. Using the labeled cDNA fragment as a probe, the Northern hybridization with the Multiple Tissue Northern Blots (Human MTN Blot, Clontech) containing poly(A)$^+$RNA extracted from various human tissues was carried out as described below. The filter membrane was soaked in the hybridization solution containing $^{32}$P-dCTP labeled cDNA fragment of LAT3 gene at 42° C. for overnight. Then the filter was washed with 0.1×SSC containing 0.1% SDS at 65° C.

From the results of Northern blotting (FIG. 3), it was demonstrated that the LAT3 was expressed strongly in a pancreas, a liver, a skeletal muscle, a heart, a bone marrow and a fetal liver, and weakly in a kidney, a placenta, a lung, a small intestine, an ovary, a testis, a prostate and a spleen.

Example 2

Identification of Mouse cDNA of the Amino Acid Transporter LAT3 Capable of Sodium-Independently and Selectively Transporting Branched Neutral Amino Acids and Analogs Thereof as a Single Molecule A cDNA clone (IMAGE clone I.D.: 4910149) corresponding to the base sequence derived from the mouse salivary gland (GenBank™/EBI/DDBJ accession No.BG865268) which is homologous with human LAT3, and obtained by searching EST (expressed sequence tag) database using a base sequence of the open reading frame of the human LAT3, was purchased from IMAGE (Integrated and Molecular Analysis of Genomes and their Expression), and the whole base sequence of the cDNA was determined by the dye terminator cycle sequencing method (Applied Biosystems) using a synthetic primer. Base sequence of cDNA was analyzed, and the open reading frame and amino acid sequence of the protein encoded thereby were determined.

This sequence is shown as SEQ ID NO: 4 in the sequence listing described later.

The comparison of amino acid sequences between the human LAT3 and the mouse LAT3 was shown in FIG. 2. Homology of amino acid sequence between the mouse LAT3 and the human LAT3 was 82%.

Example 3

Characterization of the Amino Acid Transporter LAT3 Capable of Sodium-Independently and Selectively Transporting Branched Neutral Amino Acids as a Single Molecule (1) Functional Expression of the Human LAT3 in *Xenopus laevis* oocytes An expression plasmid vector pSPORT1 containing cDNA of human LAT3 was cleaved by a restriction enzyme NotI, and cRNA (RNA complementary to cDNA) was prepared using T7 RNA polymerase.

The oocytes was injected with 25 ng of human LAT3 gene cRNA to be expressed thereby, and cultured for 3 days.

The experiment of the leucine uptake was carried out as follows according to the above described method in Example 1 (1). That is, the oocytes injected with the cRNA of the human LAT3 gene or water as a control were cultured for 10 minutes in Na$^+$-free uptake solution containing $^{14}$C-leucine (100 μM) (refer to Example 1 (1)), and measured uptake of radioactivity into the cells.

Figure 4:
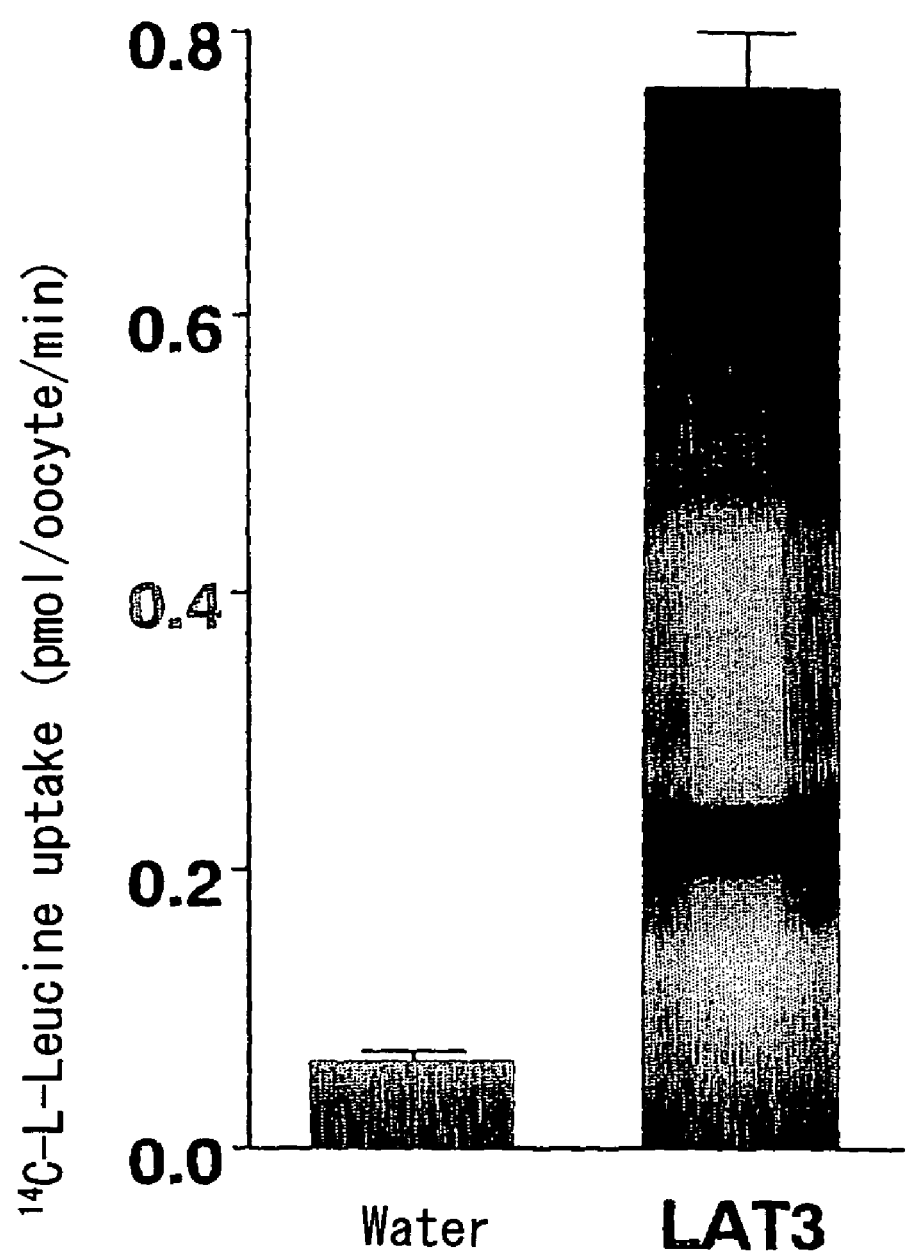
FIG. 4 shows experimental results of the leucine uptake by the oocytes injected with cRNA of human LAT3 gene.

As a result (FIG. 4), significant augmentation of the leucin uptake was detected in the oocytes expressing LAT3 compared with that injected with water. The already known system L transporters LAT1 and LAT2 require coexistence of a single transmembrane-type complementary factor 4F2hc for the expression of their function, whereas LAT3 was functional by itself without need for 4F2hc.

(2) Salt Dependency of the Human LAT3 for its Transporting Activity

Influence of salts to be added to the culture medium on the leucine uptake into the oocytes injected with the cRNA of the human LAT3 gene was investigated. Experiment of the leucine uptake was carried out using the oocytes injected with human LAT3 gene cRNA, according to the above-described method in Example 3 (1).

When influence of sodium ion is examined, Na$^+$-free uptake solution was used in place of the standard solution for uptake. When influence of chloride ion is examined, Cl$^-$-free uptake solution (Cl$^-$ in the standard uptake solution was replaced with gluconate) was used in place of the standard uptake solution.

Figure 5:
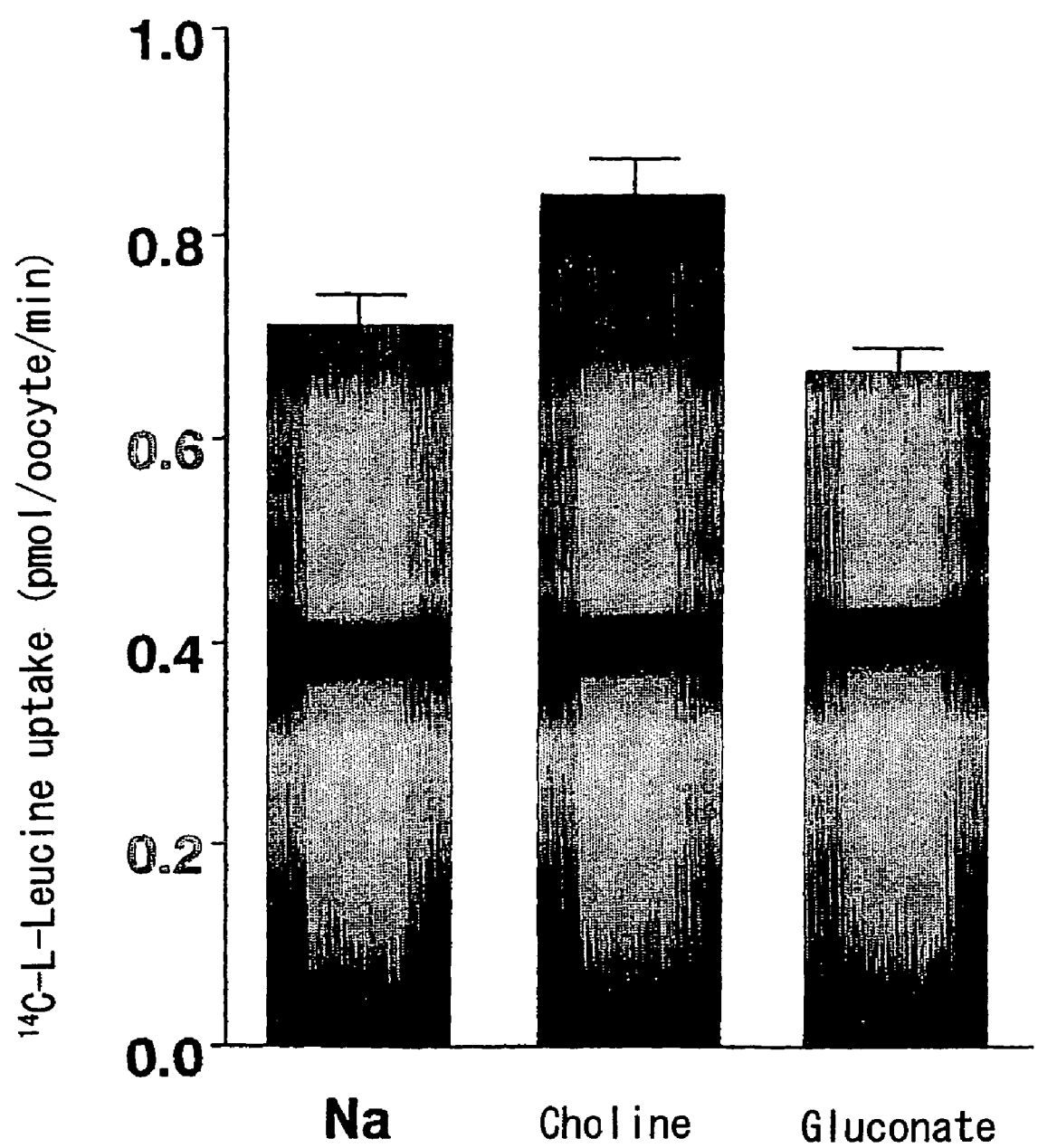
FIG. 5 shows influences of salts to be added on the leucine uptake by the oocytes injected with cRNA of human LAT3 gene.

As a result (FIG. 5), replacements of the extracellular sodium ion by choline, and the extracellular chloride ion by gluconate did not affect on the leucine uptake. As the results, LAT3 was shown to be a transporter acting independently from sodium ion and chloride ion.

(3) Dynamics Study of Human LAT3

Dynamics examination of the amino acid transporter LAT3 capable of sodium-independently and selectively transporting branched neutral amino acids was carried out. Dynamics examination of the LAT3 was performed by investigating change in leucine uptake rate by change in concentration of substrate leucine.

Figure 6:
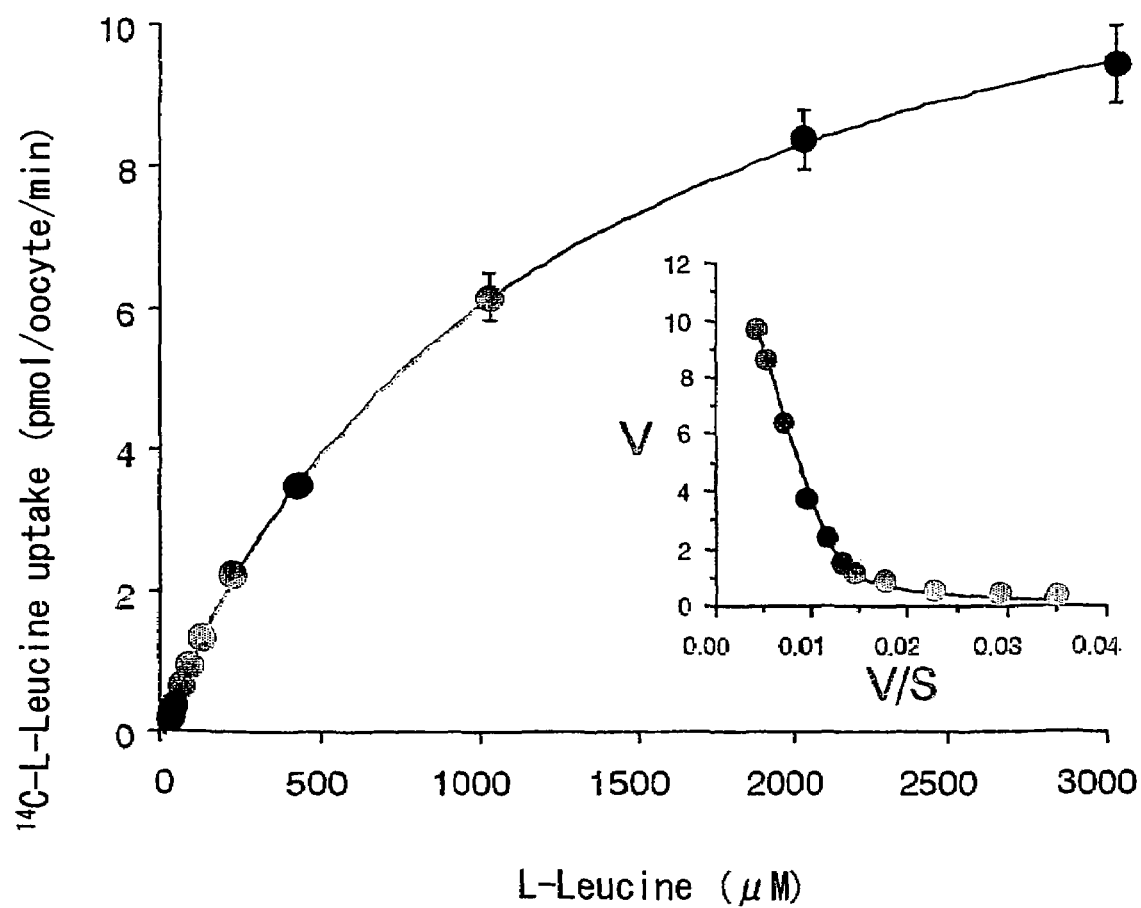
FIG. 6 shows influences of concentration of leucine as a substrate on the leucine uptake by the oocytes injected with cRNA of human LAT3 gene. Inserted figure shows Eadie-Hofstee's plot.

The leucine uptake was conducted at the leucin concentrations of 1, 3, 10, 30, 60, 100, 200, 400, 1000, 2000 and 3000 μM using the oocytes injected with cRNA of the human LAT3 gene according to the above-described method in Example 3 (1). As a result (FIG. 6), the leucine uptake by the oocyte showed the concentration-dependent and saturable substrate transport, and was confirmed to be the transporter mediated uptake. In addition, it was clarified that the leucine transport mediated by LAT3 is composed of high affinity component and low affinity component (FIG. 6, inserted figure).

(4) Substrate Selectivity of the Human LAT3 (Inhibition by Amino Acids and Analogs Thereof)

Influence of amino acids and analogs thereof on the leucine uptake into the oocytes injected with cRNA of the human LAT3 gene was investigated.

An experiment of leucine uptake was carried out using the oocytes injected with cRNA of the human LAT3, according to the above-described method in Example 3 (1), provided that the uptake of $^{14}$C-leucine (100 μM) was measured in the presence or the absence of 10 mM of various compounds (unlabeled) in the Na$^+$-free uptake solution.

Figure 7:
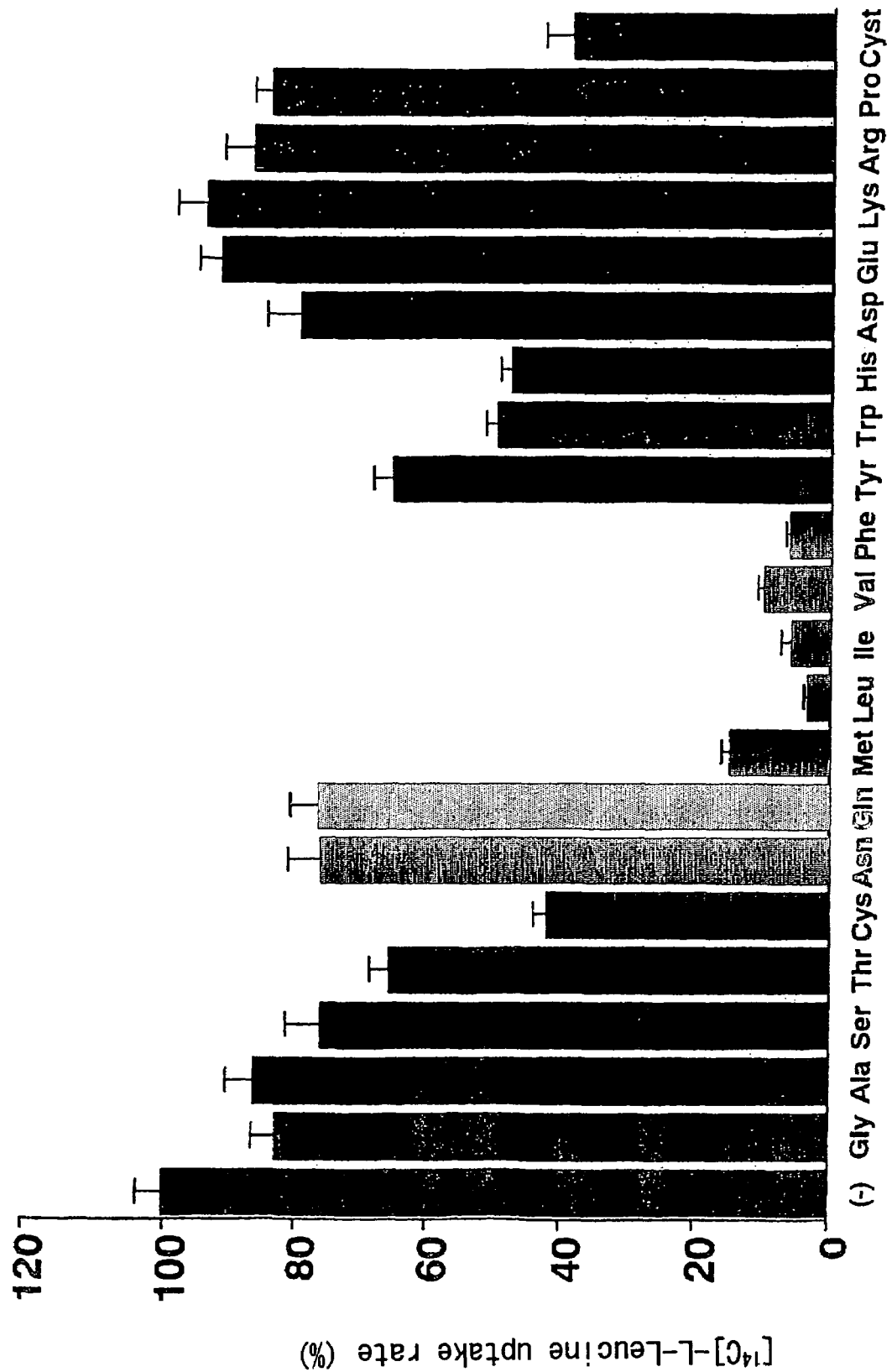
FIG. 7 shows influences of glycine and various L-amino acids added in the system on the leucine uptake by the oocytes injected with cRNA of human LAT3 gene.

As a result (FIG. 7), strong cis-inhibitory effect was observed for isoleucine, valine, phenylalanine and methionine. Acidic amino acids (aspartic acid and glutamic acid), basic amino acids (lysine and arginine), and proline did not affect on the LAT3 mediated $^{14}$C-leucine uptake.

Figure 8:
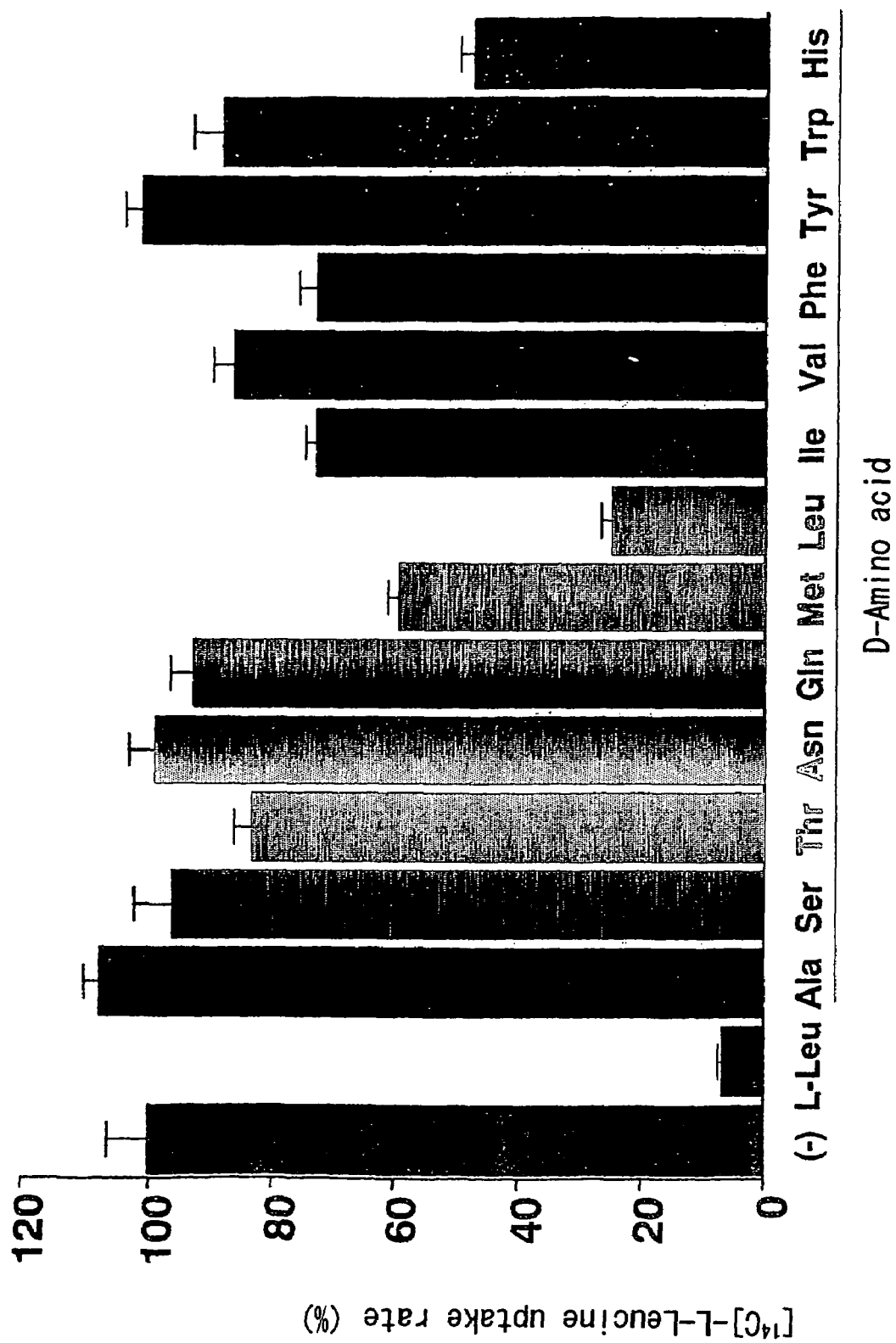
FIG. 8 shows influences of various D-amino acids added in the system on the leucine uptake by the oocytes injected with cRNA of human LAT3 gene.

Among D-amino acids, relatively strong inhibitory effect on the LAT3 mediated $^{14}$C-leucine uptake was observed in D-leucin (FIG. 8).

Figure 9:
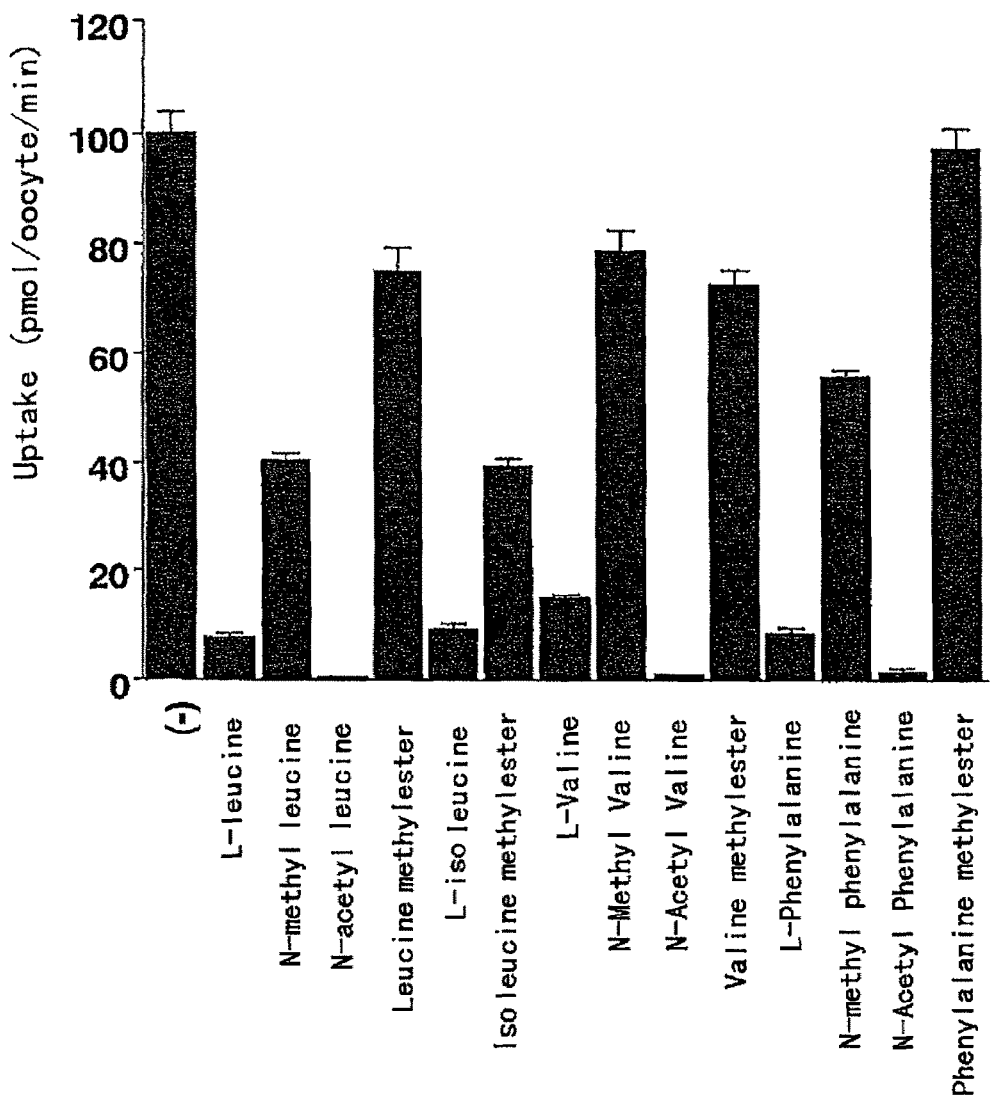
FIG. 9 shows influences of various selective inhibitors against amino acid transport system added in the system on the leucine uptake by the oocytes injected with cRNA of human LAT3 gene.

Specific inhibitors of the transport system such as BCH (2-aminobicyclo-(2,2,1)-heptane-2-carboxylic acid), AIB (α-aminoisobutyric acid), and MeAIB (α-(aminomethyl) isobutyric acid) were tested for their inhibitory effects on the LAT3 mediated $^{14}$C-leucine uptake. From the result of strong inhibition by system L specific inhibitor BCH, LAT3 was recognized as a transport system L transporter (FIG. 9).

Figure 10:
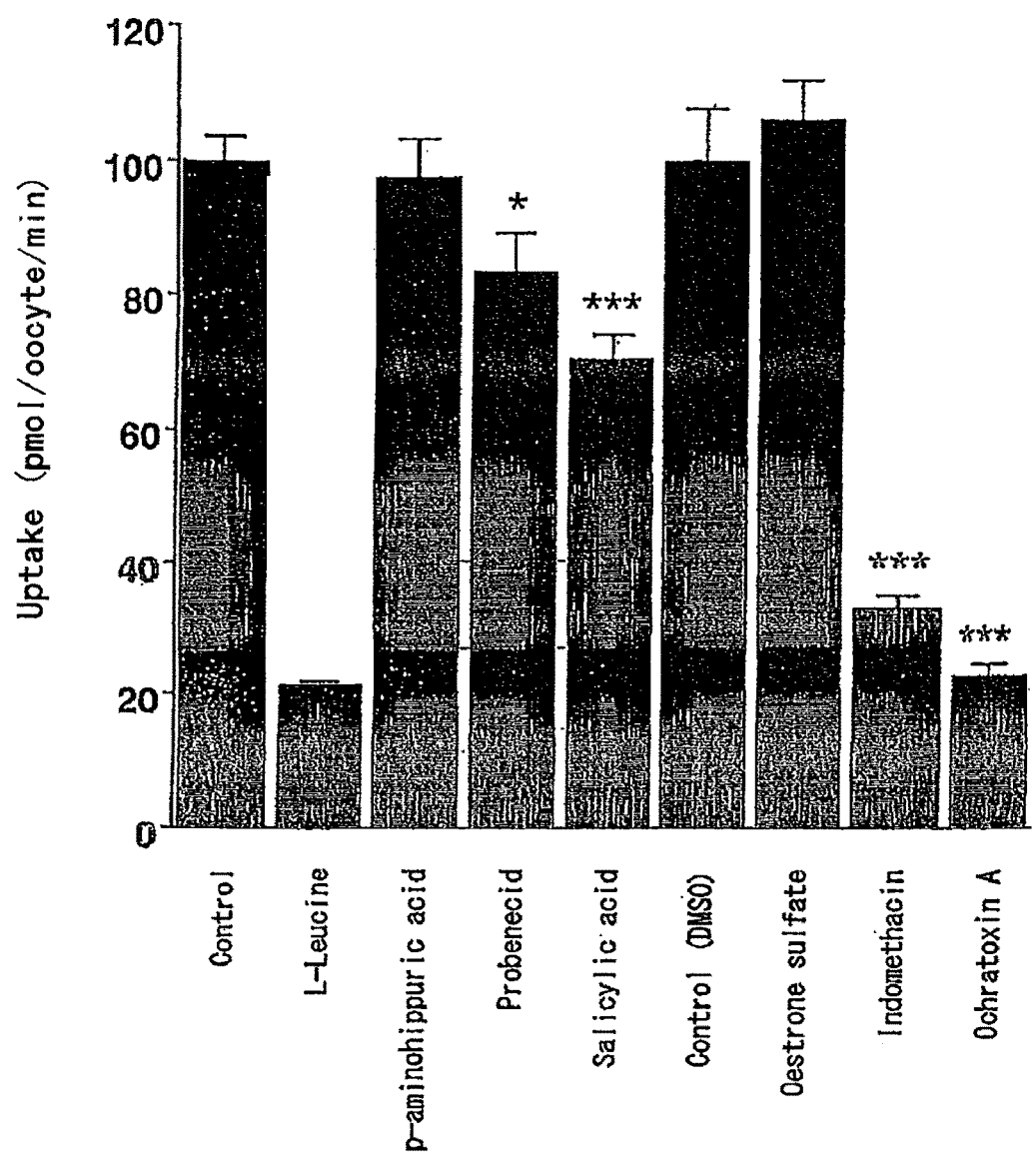
FIG. 10 shows influences of various amino acid derivatives added in the system on the leucine uptake by the oocytes injected with cRNA of human LAT3 gene.

The LAT3 mediated $^{14}$C-leucine uptake was strongly inhibited by leucinol (FIG. 10). Also, valinol and phenylaninol showed relatively strong inhibitory effects on the $^{14}$C-leucine uptake (FIG. 10). Isopentylamine, 1,3-dimethyl-n-butylamine, leucine methylester, N-acetyl-leucine, isobutylamine and phenylethylamine also showed significant inhibitory activity (FIG. 10).

Influences of various anionic compounds on the LAT3 mediated $^{14}$C-leucine uptake were investigated. As a result (FIG. 11), strong inhibitory effect was observed in ochratoxin A and indomethacin. Also, probenecid and salicylic acid showed weak but significant inhibitory effects.

(5) Substrate Selectivity of the Human LAT3 (Uptake Test using Various Amino Acids and Amino Acid Analogs as a Substrate)

Using various amino acids and amino acid analogs as substrate, the uptake mediated by the LAT3 was investigated.

An uptake experiment of various amino acids and amino acid analogs was carried out using the oocytes injected with cRNA of the human LAT3 gene according to the above-described method in Example 3 (1), provided that various radiolabeled amino acids were utilized in place of the $^{14}$C-leucine.

As a result (FIG. 12), when L-leucine ($^{14}$C-labeled), L-isoleucine ($^{14}$C-labeled), L-valine ($^{14}$C-labeled), and L-phenylalanine ($^{14}$C-labeled) were used as a substrate, a large amount of uptake into the oocytes was observed. When L-methionine ($^{14}$C-labeled), and L-proline ($^{14}$C-labeled) were used as a substrate, small but significant uptake into the oocytes was observed. When D-leucine ($^{14}$C-labeled) was used as substrate, significant uptake into the oocytes was also observed. The LAT3 mediated $^{14}$C-leucine uptake was strongly inhibited by ochratoxin A, but ochratoxin A ($^{14}$C-labeled) was not transported by LAT3.

(6) Influence of pH on the Transport Activity of LAT3

Influence of pH on the leucine uptake into the oocytes injected with cRNA of the human LAT3 gene was investigated.

An experiment of the leucine uptake was carried out using the oocytes injected with cRNA of the human LAT3 gene according to the above-described method of Example 3 (1).

As a result, the stable leucine uptake was observed at pH 7.0 to 8.5, and the physiological pH was considered the optimum pH for the LAT3.

(7) Examination of LAT3 Mediated Amino Acid Efflux

Using the oocytes injected with cRNA of the human LAT3 gene, efflux of radioactivity from the relevant oocytes preloaded with $^{14}$C-leucine was examined.

The oocytes injected with cRNA of the human LAT3 gene was injected with 100 nl of 400 μM $^{14}$C-leucine (2 nCi). After washing the oocytes with the leucine-free and Na$^+$-free uptake solution which was previously cooled with ice, the oocytes were transferred to the Na$^+$-free uptake solution with or without leucine (1 mM) at room temperature (18 to 22° C.), then efflux of $^{14}$C-leucine was measured. As a control, 100 nl of 400 μM $^{14}$C-leucine (2 nCi) was injected into the oocytes injected with water instead of cRNA of the human LAT3 gene, and the extracellular efflux of $^{14}$C-leucine was measured by the same procedures as described above.

As a result, the significant efflux of $^{14}$C-leucine from the oocytes injected with cRNA of the human LAT3 gene was observed even in the absence of extra-cellular leucine, and the efflux was increased in some degree in the presence of leucine, but the difference was not so large (FIG. 14). In contrast, only a low level of efflux of preloaded $^{14}$C-leucine was detected in the control oocytes injected with water instead of cRNA of the human LAT3 gene (FIG. 14). It was thus concluded that the LAT3 leaves a little possibility to be a substrate exchange transporter, but is mostly a transporter of the facilitated diffusion type.

(8) Influence of N-ethylmaleimide

Influence of N-ethylmaleimide on the leucine uptake into the oocytes injected with cRNA of the human LAT3 gene was investigated.

Each of the oocytes injected with cRNA of the human LAT3 gene, injected with cRNA of the human LAT3 gene and cRNA of 4F2hc gene, or injected with water as a control was cultured for 10 minutes in the Na$^+$-free uptake solution containing $^{14}$C-L-leucine (100 µM) (refer to Example 3 (2)), and uptake of radioactivity into the oocytes was measured according to the method described in Example 3 (1). In this regard, influences of pretreatment with 5 mM of N-ethylmaleimide for 15 minutes, and the presence or absence of 5 mM of N-ethylmaleimide in the uptake solution on the $^{14}$C-leucine uptake were investigated.

As a result, the pretreatment of the oocytes with N-ethylmaleimide completely abolished $^{14}$C-L-leucine uptake. (FIG. 15). This effect of N-ethylmaleimide was observed regardless of presence or absence of the N-ethylmaleimide in the uptake solution. In contrast, N-ethylmaleimide did not affect $^{14}$C-L-leucine uptake mediated by LAT1 (FIG. 15).

(9) Expression of LAT3 in Human Prostate Carcinoma and Human Renal Carcinoma.

According to the general procedures, paraffin sections of specimens removed surgically from human prostate carcinoma and human renal carcinoma were treated with affinity purified anti-LAT3 antiserum (2 µg/ml), and stained with diaminobenzidine. For the purpose of testing staining specificity, the treatment of the paraffin sections with affinity purified anti-LAT3 antiserum (2 µg/ml) in the presence of 200 µg/ml of antigen peptide was also examined.

As a result, the staining of LAT3 was observed correspondently to the tumor cells in human prostate carcinoma (FIG. 16A) and human renal carcinoma (FIG. 16C). In this staining, after treatment of the paraffin sections with anti-LAT3 antibody in the presence of antigen peptide, the color development was not observed, and thus the staining specificity was verified (FIGS. 16B and 16D).

(10) Functional Confirmation of Mouse LAT3

The cDNA of mouse LAT3 obtained by Example 2 was cleaved at NotI site, and cRNA was prepared using SP6 RNA polymerase. The cRNA of the mouse LAT3 gene was expressed in the oocytes and the $^{14}$C-L-leucine uptake was measured.

The oocytes was injected with 25 ng of cRNA of the mouse LAT3 gene to be expressed thereby, and cultured for 3 days. An experiment of the leucine uptake by the oocytes injected with cRNA of the mouse LAT3 gene was carried out according to the method in Example 3 (1).

As a result, significant augmentation of leucin uptake was detected in the oocytes expressing mouse LAT3 as well as human LAT3 compared with that injected with water. Further, the substrate selectivity of the mouse LAT3 was same as that of human LAT3.

Example 4

Identification of Human and Mouse cDNA of the Amino Acid Transporter LAT4 Capable of Sodium-Independently and Selectively Transporting Branched Neutral Amino Acids as a Single Molecule (1) Identification of LAT4 cDNA A cDNA clone (IMAGE clone I.D.: 2783525) corresponding to the base sequence derived from a human fetal brain (GenBank™/EBI/DDBJ accession No. AW162917) which is homologous with human LAT3 and a cDNA clone (IMAGE clone I.D.: 2235970) corresponding to the base sequence derived from a mouse kidney (GenBank™/EBI/DDBJ accession No. AW106550) which is homologous with human LAT3, which were obtained by searching EST (expressed sequence tag) database using a base sequence of the open reading frame of the human LAT3, and were purchased from IMAGE (Integrated and Molecular Analysis of Genomes and their Expression), and the whole base sequence of cDNAs were determined by the dye terminator cycle sequencing method (Applied Biosystems) using synthetic primers. Also, the base sequence of cDNA was analyzed by the general method, and the open reading frame and amino acid sequence of the proteins encoded thereby were determined.

This human sequence is shown as SEQ ID NO: 5, and the mouse sequence is shown as SEQ ID NO: 7 in the sequence listing described later.

The comparison of amino acid sequences between human LAT3 and human LAT4 was shown in FIG. 17. Homology of amino acid sequence between human LAT3 and human LAT4 was 58%.

The comparison of amino acid sequences between human LAT3 and mouse LAT4 was shown in FIG. 18. Homology of amino acid sequence between human LAT3 and mouse LAT4 was 90%.

(2) Expression of LAT4 Gene in Various Human and Mouse Tissues (Analyzed by Northern Blotting)

A cDNA fragment corresponding to a base sequence of the 307th to the 1012th of the human LAT4 gene was labeled with $^{32}$P-dCTP and used as a probe. Using the labeled cDNA fragment as a probe, the Northern hybridization with the Multiple Tissue Northern Blots (Human MTN Blot, Clontech) containing poly(A)$^+$RNA extracted from various human tissues was carried out as described below. The filter membrane was soaked in the hybridization solution containing $^{32}$P-dCTP labeled cDNA fragment of the LAT4 gene at 42° C. for overnight. Then the filter was washed with 0.1× SSC containing 0.1% SDS at 65° C.

As the results of Northern blotting (FIG. 24), it was demonstrated that LAT4 was expressed strongly in a placenta, a kidney and a skeletal muscle, and weakly in a leucocyte, a brain, a heart, a spleen, a small intestine, a lung and a colon, and more weakly in a thymus and a liver.

A cDNA fragment corresponding to a base sequence of the 122th to the 525th of the mouse LAT4 gene was labeled with $^{32}$P-dCTP and used as a probe. Using the labeled cDNA fragment as a probe, the Northern hybridization with RNA extracted from various hmouse tissues was carried out as described below. Three (3) µg of poly(A)$^+$RNA was electrophoresed on a 1% agarose/formaldehyde gel, and transferred to a nitrocellulose filter. The filter membrane was soaked in the hybridization solution containing $^{32}$P-dCTP labeled cDNA fragment of the mouse LAT4 at 42° C. for overnight. Then the filter was washed with 0.1×SSC containing 0.1% SDS at 65° C.

As the results of Northern blotting (FIG. 25), it was demonstrated that the LAT4 was expressed strongly in a kidney, a placenta, a brain and a small intestine of mouse.

Example 5

Characterization of the Amino Acid Transporter LAT4 Capable of Sodium-Independently and Selectively Transporting Branched Neutral Amino Acids as a Single Molecule (1) Functional Expression of the Mouse LAT4 in *Xenopus laevis* oocytes An expression plasmid vector pcDNA 3.1(+) containing cDNA of mouse LAT4 was cleaved by a restriction enzyme XbaI, and cRNA (RNA complementary to cDNA) was prepared using T7 RNA polymerase.

The oocytes was injected with 25 ng of cRNA of the mouse LAT4 gene to be expressed thereby, and cultured for 3 days.

An experiment of leucine uptake was carried out as follows according to the above-described method in Example 3 (1). That is, the oocytes injected with cRNA of the mouse LAT4 gene or water as a control were cultured for 10 minutes in the $Na^+$-free uptake solution containing $^{14}C$-leucine (100 μM) (refer to Example 3 (1)), and measured the uptake of radioactivity into the cells.

As a result, significant augmentation of the leucin uptake was detected in the oocytes expressing LAT4, compared with that injected with water. Unlike with the already known system L transporters LAT1 and LAT2, but just like LAT3, LAT4 was functional by itself without need for 4F2hc.

(2) Salt Dependency of Transporting Activity of the Mouse LAT4

Influence of salts to be added to the culture medium on the leucine uptake into oocytes injected with cRNA of the mouse LAT4 gene was investigated. An experiment of the leucine uptake was carried out using oocytes injected with cRNA of the mouse LAT4 gene, according to the above described method in Example 3 (1).

When influence of sodium ion is examined, the $Na^+$-free uptake solution was used in place of the standard solution for uptake. When influence of chloride ion is examined, $Cl^-$-free uptake solution ($Cl^-$ in the standard uptake solution was replaced with gluconate) was used in place of the standard solution for uptake.

As a result (FIG. 19), replacements of the extracellular sodium ion by choline, and the extracellular chloride ion by gluconate did not affect on the leucine uptake. As the results, LAT4 was recognized as the transporter acting independently from sodium ion and chloride ion.

(3) Dynamics Study of the Mouse LAT4

Dynamics examination of the amino acid transporter LAT4 capable of sodium-independently and selectively transporting branched neutral amino acids was carried out. Dynamics examination of LAT4 was performed by investigating change in leucine uptake rate by a change in concentration of substrate leucine.

The leucine uptake was conducted at the leucin concentrations of 0.01, 0.03, 0.1, 0.3, 1, 3 and 10 mM, using the oocytes injected with cRNA of the mouse LAT4 gene according to the above-described method in Example 3 (1). As a result, the leucine uptake by the oocyte showed concentration-dependent and saturable substrate transport, and was confirmed to be the transporter mediated uptake. In addition, it was clarified that the leucine transport mediated by LAT4 is composed of a high affinity component and a low affinity component, just like the leucin uptake mediated by LAT3.

(4) Substrate Selectivity of the Mouse LAT4 (Inhibition by Amino Acids and Analogs Thereof)

Influence of amino acids and analogs thereof on the leucine uptake into the oocytes injected with cRNA of the mouse LAT4 gene was investigated.

An experiment of leucine uptake was carried out using the oocytes injected with cRNA of the mouse LAT4 gene, according to the above-described method in Example 3 (1). In this regard, uptake of $^{14}C$-leucine (100 μM) into the oocytes was measured in the presence or the absence of 10 mM of various compounds (unlabeled) in the $Na^+$-free uptake solution.

As a result (FIG. 20), strong cis-inhibitory effect was observed for isoleucine, valine, phenylalanine and methionine. Acidic amino acids (aspartic acid and glutamic acid), basic amino acids (lysine and arginine), and proline did not affect on the LAT4 mediated $^{14}C$-leucine uptake.

Among D-amino acids, relatively strong inhibitory effect on the LAT4 mediated $^{14}C$-leucine uptake was observed for D-leucin, D-histidine and D-methionine (FIG. 21).

Specific inhibitors of the transport system such as BCH (2-aminobicyclo-(2,2,1)-heptane-2-carboxylic acid), AIB (α-aminoisobutyric acid), and MeAIB (α-(aminomethyl) isobutyric acid) were tested for their inhibitory effects on the LAT4 mediated $^{14}C$-leucine uptake. From the result of strong inhibition by the system L specific inhibitor BCH, LAT4 was recognized as a transport system L transporter (FIG. 22).

(5) Substrate Selectivity of the Mouse LAT4 (Uptake Test using Various Amino Acids and Amino Acid Analogs as Substrate)

Using various amino acids and amino acid analogs as substrate, uptake mediated by LAT4 was investigated.

An uptake experiment of various amino acids and amino acid analogs was carried out using the oocytes injected with cRNA of the mouse LAT4 gene according to the above-described method in Example 3 (1). In this regard, in place of $^{14}C$-leucine, various radiolabeled amino acids were utilized.

As a result (FIG. 23), when L-leucine ($^{14}C$-labeled), L-isoleucine ($^{14}C$-labeled), L-valine ($^{14}C$-labeled), L-phenylalanine ($^{14}C$-labeled), and L-methionine ($^{14}C$-labeled) were used as substrate, a large amount of uptake into the oocytes was observed. Also, when D-leucine ($^{14}C$-labeled) was used as substrate, significant uptake into the oocytes was observed.

(6) Functional Confirmation of Human LAT4

The cDNA of human LAT4 gene obtained by Example 4 was cleaved at XhoI site, and the cRNA was prepared using T3 RNA polymerase. The cRNA of the human LAT4 gene was expressed in the oocytes and the $^{14}C$-L-leucine uptake was measured.

The oocytes was injected with 25 ng of cRNA of the human LAT4 gene, and cultured for 3° days. Experiment of the leucine uptake by the oocytes injected with cRNA of the human LAT4 gene was carried out according to the method of Example 3 (1).

As a result, significant augmentation of leucin uptake was detected in the oocytes expressing human LAT4 as well as mouse LAT4 compared with that injected with water as a control. Further, the substrate selectivity of human LAT4 was the same as that of mouse LAT4.

INDUSTRIAL APPLICABILITY

The amino acid transporter of the present invention capable of transporting branched neutral amino acids as a single molecule provides a possibility to perform in vitro study on the transport of amino acid-related compounds including branched neutral amino acids and drugs or extraneous substances at the site where the relevant transporter is expressed, and to predict in vivo kinetics of these substances based on the above mentioned in vitro study. Further, the relevant transporter is considered useful for developing medical drugs capable of passing efficiently through the site where the relevant transporter is expressed. Further more, the amino acid transporter of the present invention capable of transporting branched neutral amino acids as a single molecule may be used for developing a method for modulating amino acid metabolism and a method for controlling growth of normal cells or tumor cells, by modulating the capability of transporting branched neutral amino acids and analogs thereof.

The invention claimed is:

1. An isolated protein which consists of the amino acid sequence set forth in SEQ ID NO: 6.

2. A method for detecting activity of a compound as a substrate or an inhibitor for transporting activity of a sodium-independent branched neutral amino acids transporter protein, which comprises the steps of a) obtaining transformed cells expressing a transporter protein consisting of the amino acid sequence of SEQ ID NO: 2 or SEQ ID NO: 6, and b) incubating the test compound with said cells and c) detecting the activity of the compound as a substrate or an inhibitor for transporting activity of the transporter protein.

* * * * *

SEQUENCE LISTING

<160> NUMBER OF SEQ ID NOS: 8

<210> SEQ ID NO 1
<211> LENGTH: 2525
<212> TYPE: DNA
<213> ORGANISM: Homo sapiens
<220> FEATURE:
<221> NAME/KEY: CDS
<222> LOCATION: (257)..(1933)

<400> SEQUENCE: 1

```
gcttcgcaga cctctggcgc cggcgggtt cccagttccc ccgcttcttc cgaggagaca      60
gcggaggcga ggccaccggg ctgtcaggct gaagctccgt ggcggccggg tcctgcacgc     120
agagaagacc ccagcgccgg cgcggctcag ggctgggccc acgggactcc ggacgcgccg     180
cgaaagcgtt gcgctcccgg aggcgtccgc agctgctggc tgctcatttg ccggtgaccg     240
gaggctcggg ccagc atg gcc ccc acg ctg caa cag gcg tac cgg agg cgc     292
                 Met Ala Pro Thr Leu Gln Gln Ala Tyr Arg Arg
                  1               5                  10 tgg tgg atg gcc tgc acg gct gtg ctg gag aac ctc ttc ttc tct gct     340
Trp Trp Met Ala Cys Thr Ala Val Leu Glu Asn Leu Phe Phe Ser Ala
         15                  20                  25 gta ctc ctg ggc tgg ggc tcc ctg ttg atc att ctg aag aac gag ggc     388
Val Leu Leu Gly Trp Gly Ser Leu Leu Ile Ile Leu Lys Asn Glu Gly
 30                  35                  40 ttc tat tcc agc acg tgc cca gct gag agc agc acc aac acc acc cag     436
Phe Tyr Ser Ser Thr Cys Pro Ala Glu Ser Ser Thr Asn Thr Thr Gln
 45                  50                  55                  60 gat gag cag cgc agg tgg cca ggc tgt gac cag cag gac gag atg ctc     484
Asp Glu Gln Arg Arg Trp Pro Gly Cys Asp Gln Gln Asp Glu Met Leu
                 65                  70                  75 aac ctg ggc ttc acc att ggt tcc ttc gtg ctc agc gcc acc acc ctg     532
Asn Leu Gly Phe Thr Ile Gly Ser Phe Val Leu Ser Ala Thr Thr Leu
         80                  85                  90 cca ctg ggg atc ctc atg gac cgc ttt ggc ccc cga ccc gtg cgg ctg     580
Pro Leu Gly Ile Leu Met Asp Arg Phe Gly Pro Arg Pro Val Arg Leu
     95                 100                 105 gtt ggc agt gcc tgc ttc act gcg tcc tgc acc ctc atg gcc ctg gcc     628
Val Gly Ser Ala Cys Phe Thr Ala Ser Cys Thr Leu Met Ala Leu Ala
110                 115                 120 tcc cgg gac gtg gaa gct ctg tct ccg ttg ata ttc ctg gcg ctg tcc     676
Ser Arg Asp Val Glu Ala Leu Ser Pro Leu Ile Phe Leu Ala Leu Ser
125                 130                 135                 140 ctg aat ggc ttt ggt ggc atc tgc cta acg ttc act tca ctc acg ctg     724
Leu Asn Gly Phe Gly Gly Ile Cys Leu Thr Phe Thr Ser Leu Thr Leu
                145                 150                 155 ccc aac atg ttt ggg aac ctg cgc tcc acg tta atg gcc ctc atg att     772
Pro Asn Met Phe Gly Asn Leu Arg Ser Thr Leu Met Ala Leu Met Ile
        160                 165                 170 ggc tct tac gcc tct tct gcc att acg ttc cca gga atc aag ctg atc     820
Gly Ser Tyr Ala Ser Ser Ala Ile Thr Phe Pro Gly Ile Lys Leu Ile
    175                 180                 185 tac gat gcc ggt gtg gcc ttc gtg gtc atc atg ttc acc tgg tct ggc     868
Tyr Asp Ala Gly Val Ala Phe Val Val Ile Met Phe Thr Trp Ser Gly
190                 195                 200 ctg gcc tgc ctt atc ttt ctg aac tgc acc ctc aac tgg ccc atc gaa     916
Leu Ala Cys Leu Ile Phe Leu Asn Cys Thr Leu Asn Trp Pro Ile Glu
205                 210                 215                 220
```

-continued

| | | |
|---|---|---|
| gcc ttt cct gcc cct gag gaa gtc aat tac acg aag aag atc aag ctg<br>Ala Phe Pro Ala Pro Glu Glu Val Asn Tyr Thr Lys Lys Ile Lys Leu<br>225 230 235 | 964 | |
| agt ggg ctg gcc ctg gac cac aag gtg aca ggt gac ctc ttc tac acc<br>Ser Gly Leu Ala Leu Asp His Lys Val Thr Gly Asp Leu Phe Tyr Thr<br>240 245 250 | 1012 | |
| cat gtg acc acc atg ggc cag agg ctc agc cag aag gcc ccc agc ctg<br>His Val Thr Thr Met Gly Gln Arg Leu Ser Gln Lys Ala Pro Ser Leu<br>255 260 265 | 1060 | |
| gag gac ggt tcg gat gcc ttc atg tca ccc cag gat gtt cgg ggc acc<br>Glu Asp Gly Ser Asp Ala Phe Met Ser Pro Gln Asp Val Arg Gly Thr<br>270 275 280 | 1108 | |
| tca gaa aac ctt cct gag agg tct gtc ccc tta cgc aag agc ctc tgc<br>Ser Glu Asn Leu Pro Glu Arg Ser Val Pro Leu Arg Lys Ser Leu Cys<br>285 290 295 300 | 1156 | |
| tcc ccc act ttc ctg tgg agc ctc ctc acc atg ggc atg acc cag ctg<br>Ser Pro Thr Phe Leu Trp Ser Leu Leu Thr Met Gly Met Thr Gln Leu<br>305 310 315 | 1204 | |
| cgg atc atc ttc tac atg gct gct gtg aac aag atg ctg gag tac ctt<br>Arg Ile Ile Phe Tyr Met Ala Ala Val Asn Lys Met Leu Glu Tyr Leu<br>320 325 330 | 1252 | |
| gtg act ggt ggc cag gag cat gag aca aat gaa cag caa caa aag gtg<br>Val Thr Gly Gly Gln Glu His Glu Thr Asn Glu Gln Gln Gln Lys Val<br>335 340 345 | 1300 | |
| gca gag aca gtt ggg ttc tac tcc tcc gtc ttc ggg gcc atg cag ctg<br>Ala Glu Thr Val Gly Phe Tyr Ser Ser Val Phe Gly Ala Met Gln Leu<br>350 355 360 | 1348 | |
| ttg tgc ctt ctc acc tgc ccc ctc att ggc tac atc atg gac tgg cgg<br>Leu Cys Leu Leu Thr Cys Pro Leu Ile Gly Tyr Ile Met Asp Trp Arg<br>365 370 375 380 | 1396 | |
| atc aag gac tgc gtg gac gcc cca act cag ggc act gtc ctc gga gat<br>Ile Lys Asp Cys Val Asp Ala Pro Thr Gln Gly Thr Val Leu Gly Asp<br>385 390 395 | 1444 | |
| gcc agg gac ggg gtt gct acc aaa tcc atc aga cca cgc tac tgc aag<br>Ala Arg Asp Gly Val Ala Thr Lys Ser Ile Arg Pro Arg Tyr Cys Lys<br>400 405 410 | 1492 | |
| atc caa aag ctc acc aat gcc atc agt gcc ttc acc ctg acc aac ctg<br>Ile Gln Lys Leu Thr Asn Ala Ile Ser Ala Phe Thr Leu Thr Asn Leu<br>415 420 425 | 1540 | |
| ctg ctt gtg ggt ttt ggc atc acc tgt ctc atc aac aac tta cac ctc<br>Leu Leu Val Gly Phe Gly Ile Thr Cys Leu Ile Asn Asn Leu His Leu<br>430 435 440 | 1588 | |
| cag ttt gtg acc ttt gtc ctg cac acc att gtt cga ggt ttc ttc cac<br>Gln Phe Val Thr Phe Val Leu His Thr Ile Val Arg Gly Phe Phe His<br>445 450 455 460 | 1636 | |
| tca gcc tgt ggg agt ctc tat gct gca gtg ttc cca tcc aac cac ttt<br>Ser Ala Cys Gly Ser Leu Tyr Ala Ala Val Phe Pro Ser Asn His Phe<br>465 470 475 | 1684 | |
| ggg acg ctg aca ggc ctg cag tcc ctc atc agt gct gtg ttc gcc ttg<br>Gly Thr Leu Thr Gly Leu Gln Ser Leu Ile Ser Ala Val Phe Ala Leu<br>480 485 490 | 1732 | |
| ctt cag cag cca ctt ttc atg gcg atg gtg gga ccc ctg aaa gga gag<br>Leu Gln Gln Pro Leu Phe Met Ala Met Val Gly Pro Leu Lys Gly Glu<br>495 500 505 | 1780 | |
| ccc ttc tgg gtg aat ctg ggc ctc ctg tta ttc tca ctc ctg gga ttc<br>Pro Phe Trp Val Asn Leu Gly Leu Leu Leu Phe Ser Leu Leu Gly Phe<br>510 515 520 | 1828 | |
| ctg ttg cct tcc tac ctc ttc tat tac cgt gcc cgg ctc cag cag gag<br>Leu Leu Pro Ser Tyr Leu Phe Tyr Tyr Arg Ala Arg Leu Gln Gln Glu<br>525 530 535 540 | 1876 | |

-continued

```
tac gcc gcc aat ggg atg ggc cca ctg aag gtg ctt agc ggc tct gag      1924
Tyr Ala Ala Asn Gly Met Gly Pro Leu Lys Val Leu Ser Gly Ser Glu
                545                 550                 555 gtg acc gca tagacttctc agaccaaggg acctggatga caggcaatca              1973
Val Thr Ala aggcctgagc aaccaaaagg agtgccccat atggcttttc tacctgtaac atgcacatag    2033
agccatggcc gtagatttat aaataccaag agaagttcta tttttgtaaa gactgcaaaa    2093
aggaggaaaa aaaaccttca aaaacgcccc ctaagtcaac gctccattga ctgaagacag    2153
tccctatcct agagggggttg agctttcttc ctccttgggt tggaggagac cagggtgcct   2213
cttatctcct tctagcggtc tgcctcctgg tacctcttgg ggggatcggc aaacaggcta    2273
cccctgaggt cccatgtgcc atgagtgtgc acacatgcat gtgtctgtgt atgtgtgaat    2333
gtgagagaga cacagccctc ctttcagaag gaaaggggcc tgaggtgcca gctgtgtcct    2393
gggttagggg ttgggggtcg gccccttcca gggccaggag ggcaggttcc ctctctggtg    2453
ctgctgcttg caagtcttag aggaaataaa aagggaagtg agagaaaaaa aaaaaaaaaa    2513
aaaaaaaaaa aa                                                        2525
```

<210> SEQ ID NO 2
<211> LENGTH: 559
<212> TYPE: PRT
<213> ORGANISM: Homo sapiens

<400> SEQUENCE: 2

```
Met Ala Pro Thr Leu Gln Gln Ala Tyr Arg Arg Trp Trp Met Ala
  1               5                  10                  15

Cys Thr Ala Val Leu Glu Asn Leu Phe Phe Ser Ala Val Leu Leu Gly
                 20                  25                  30

Trp Gly Ser Leu Leu Ile Ile Leu Lys Asn Glu Gly Phe Tyr Ser Ser
             35                  40                  45

Thr Cys Pro Ala Glu Ser Ser Thr Asn Thr Thr Gln Asp Glu Gln Arg
         50                  55                  60

Arg Trp Pro Gly Cys Asp Gln Gln Asp Glu Met Leu Asn Leu Gly Phe
     65                  70                  75                  80

Thr Ile Gly Ser Phe Val Leu Ser Ala Thr Thr Leu Pro Leu Gly Ile
                 85                  90                  95

Leu Met Asp Arg Phe Gly Pro Arg Pro Val Arg Leu Val Gly Ser Ala
                100                 105                 110

Cys Phe Thr Ala Ser Cys Thr Leu Met Ala Leu Ala Ser Arg Asp Val
             115                 120                 125

Glu Ala Leu Ser Pro Leu Ile Phe Leu Ala Leu Ser Leu Asn Gly Phe
         130                 135                 140

Gly Gly Ile Cys Leu Thr Phe Thr Ser Leu Thr Leu Pro Asn Met Phe
145                 150                 155                 160

Gly Asn Leu Arg Ser Thr Leu Met Ala Leu Met Ile Gly Ser Tyr Ala
                165                 170                 175

Ser Ser Ala Ile Thr Phe Pro Gly Ile Lys Leu Ile Tyr Asp Ala Gly
             180                 185                 190

Val Ala Phe Val Val Ile Met Phe Thr Trp Ser Gly Leu Ala Cys Leu
         195                 200                 205

Ile Phe Leu Asn Cys Thr Leu Asn Trp Pro Ile Glu Ala Phe Pro Ala
     210                 215                 220

Pro Glu Glu Val Asn Tyr Thr Lys Lys Ile Lys Leu Ser Gly Leu Ala
```

225                 230                 235                 240
Leu Asp His Lys Val Thr Gly Asp Leu Phe Tyr Thr His Val Thr Thr
                245                 250                 255

Met Gly Gln Arg Leu Ser Gln Lys Ala Pro Ser Leu Glu Asp Gly Ser
            260                 265                 270

Asp Ala Phe Met Ser Pro Gln Asp Val Arg Gly Thr Ser Glu Asn Leu
        275                 280                 285

Pro Glu Arg Ser Val Pro Leu Arg Lys Ser Leu Cys Ser Pro Thr Phe
    290                 295                 300

Leu Trp Ser Leu Leu Thr Met Gly Met Thr Gln Leu Arg Ile Ile Phe
305                 310                 315                 320

Tyr Met Ala Ala Val Asn Lys Met Leu Glu Tyr Leu Val Thr Gly Gly
                325                 330                 335

Gln Glu His Glu Thr Asn Glu Gln Gln Gln Lys Val Ala Glu Thr Val
            340                 345                 350

Gly Phe Tyr Ser Ser Val Phe Gly Ala Met Gln Leu Leu Cys Leu Leu
        355                 360                 365

Thr Cys Pro Leu Ile Gly Tyr Ile Met Asp Trp Arg Ile Lys Asp Cys
370                 375                 380

Val Asp Ala Pro Thr Gln Gly Thr Val Leu Gly Asp Ala Arg Asp Gly
385                 390                 395                 400

Val Ala Thr Lys Ser Ile Arg Pro Arg Tyr Cys Lys Ile Gln Lys Leu
                405                 410                 415

Thr Asn Ala Ile Ser Ala Phe Thr Leu Thr Asn Leu Leu Leu Val Gly
            420                 425                 430

Phe Gly Ile Thr Cys Leu Ile Asn Asn Leu His Leu Gln Phe Val Thr
        435                 440                 445

Phe Val Leu His Thr Ile Val Arg Gly Phe Phe His Ser Ala Cys Gly
    450                 455                 460

Ser Leu Tyr Ala Ala Val Phe Pro Ser Asn His Phe Gly Thr Leu Thr
465                 470                 475                 480

Gly Leu Gln Ser Leu Ile Ser Ala Val Phe Ala Leu Leu Gln Gln Pro
                485                 490                 495

Leu Phe Met Ala Met Val Gly Pro Leu Lys Gly Glu Pro Phe Trp Val
            500                 505                 510

Asn Leu Gly Leu Leu Phe Ser Leu Leu Gly Phe Leu Leu Pro Ser
        515                 520                 525

Tyr Leu Phe Tyr Tyr Arg Ala Arg Leu Gln Gln Glu Tyr Ala Ala Asn
    530                 535                 540

Gly Met Gly Pro Leu Lys Val Leu Ser Gly Ser Glu Val Thr Ala
545                 550                 555

<210> SEQ ID NO 3
<211> LENGTH: 2519
<212> TYPE: DNA
<213> ORGANISM: Mus musculus
<220> FEATURE:
<221> NAME/KEY: CDS
<222> LOCATION: (257)..(1948)

<400> SEQUENCE: 3
ggcttcacct atctgtggcg ccaggacggt tcccagatcc actgcttctt tcgagggcgc    60
agacgaggtg agaccggcgg ttccgaggcc cgctgggtct ggcacgcagg gaagacaccc   120
cgcgtggatg cgatttggaa ttgggatcct gggtctcagg agatccggag tgtggaagcg   180

```
                                                       -continued ccggggagac tctgtgttac tccgggtgtc aacagctgcg ggaggcaagt tgtcgggga         240 cagagtctcg gccacc atg gct ccc acg ctg aag cag gcg tac cgc agg cgc      292
               Met Ala Pro Thr Leu Lys Gln Ala Tyr Arg Arg Arg
                 1               5                  10 tgg tgg atg gct tgc acc gct gtg gtg gag aac ctc ttc ttc tcc gcg         340
Trp Trp Met Ala Cys Thr Ala Val Val Glu Asn Leu Phe Phe Ser Ala
         15                  20                  25 gtg ctc ctg ggc tgg gcc tcc ctg ctg atc atg ctc aag aag gaa ggc         388
Val Leu Leu Gly Trp Ala Ser Leu Leu Ile Met Leu Lys Lys Glu Gly
 30                  35                  40 ttc tat tcc agc ctg tgc cca gct gag aac agg acc aat acc acc caa         436
Phe Tyr Ser Ser Leu Cys Pro Ala Glu Asn Arg Thr Asn Thr Thr Gln
 45                  50                  55                  60 gat gaa cag cat cag tgg aca agc tgt gac cag cag gaa aag atg ctc         484
Asp Glu Gln His Gln Trp Thr Ser Cys Asp Gln Gln Glu Lys Met Leu
                 65                  70                  75 aac ctg ggt ttc acc att ggc tcc ttc ctg ctg agt gct acc aca ctg         532
Asn Leu Gly Phe Thr Ile Gly Ser Phe Leu Leu Ser Ala Thr Thr Leu
             80                  85                  90 cct ctg gga att ctc atg gac cgc ttt ggg ccc agg cct ctt cga ctg         580
Pro Leu Gly Ile Leu Met Asp Arg Phe Gly Pro Arg Pro Leu Arg Leu
         95                 100                 105 gtg ggc agt gcc tgc ttt gcc gca tcc tgc act cta atg gcc ttg gcc         628
Val Gly Ser Ala Cys Phe Ala Ala Ser Cys Thr Leu Met Ala Leu Ala
110                 115                 120 tcc agg gac act gaa gtt ttg tct cca ttg ata ttc ctg gca ctg tcc         676
Ser Arg Asp Thr Glu Val Leu Ser Pro Leu Ile Phe Leu Ala Leu Ser
125                 130                 135                 140 ttg aat gga ttt gct ggc atc tgc tta acg ttt acc tca ctc acg ctg         724
Leu Asn Gly Phe Ala Gly Ile Cys Leu Thr Phe Thr Ser Leu Thr Leu
                145                 150                 155 ccc aac atg ttt ggg aat ttg cga tcc act ttc atg gcc ctc atg att         772
Pro Asn Met Phe Gly Asn Leu Arg Ser Thr Phe Met Ala Leu Met Ile
        160                 165                 170 ggc tcc tat gcg tct tct gcc atc acg ttc cct gga atc aag ctg atc         820
Gly Ser Tyr Ala Ser Ser Ala Ile Thr Phe Pro Gly Ile Lys Leu Ile
    175                 180                 185 tac gat gcc gga gtc ccc ttc act gtc atc atg ttc aca tgg tct ggc         868
Tyr Asp Ala Gly Val Pro Phe Thr Val Ile Met Phe Thr Trp Ser Gly
190                 195                 200 ctg gcc tgt ctc atc ttt ttg aac tgt gct ctc aac tgg cct gca gaa         916
Leu Ala Cys Leu Ile Phe Leu Asn Cys Ala Leu Asn Trp Pro Ala Glu
205                 210                 215                 220 gcc ttt cct gcc cct gag gaa gtt gac tac acg aag aag atc aaa ctc         964
Ala Phe Pro Ala Pro Glu Glu Val Asp Tyr Thr Lys Lys Ile Lys Leu
                225                 230                 235 att ggg tta gcc ttg gac cac aag gtc aca ggt gac cgc ttc tac acc        1012
Ile Gly Leu Ala Leu Asp His Lys Val Thr Gly Asp Arg Phe Tyr Thr
        240                 245                 250 cat gta acc att gtg ggt cag cgg ctg agt cag aag tcc ccc agc ctg        1060
His Val Thr Ile Val Gly Gln Arg Leu Ser Gln Lys Ser Pro Ser Leu
    255                 260                 265 gag gag ggc gct gac gcc ttt att tca tcc ccg gat atc cct ggt acc        1108
Glu Glu Gly Ala Asp Ala Phe Ile Ser Ser Pro Asp Ile Pro Gly Thr
270                 275                 280 tca gag gag act cct gaa aag tct gtc cct ttt cgc aag agc ctc tgc        1156
Ser Glu Glu Thr Pro Glu Lys Ser Val Pro Phe Arg Lys Ser Leu Cys
285                 290                 295                 300 tcc ccc att ttc ctg tgg agc ctt gtc acc atg ggc atg acc cag ctt        1204
```

|  |  |
|---|---|
| Ser Pro Ile Phe Leu Trp Ser Leu Val Thr Met Gly Met Thr Gln Leu<br>305 310 315 | |
| cgg gtc atc ttc tat atg ggt gct atg aac aag atc ctg gag ttc att<br>Arg Val Ile Phe Tyr Met Gly Ala Met Asn Lys Ile Leu Glu Phe Ile<br>320 325 330 | 1252 |
| gtg act ggt ggc aag gaa cgt gag aca aat gag cag aga cag aag gtg<br>Val Thr Gly Gly Lys Glu Arg Glu Thr Asn Glu Gln Arg Gln Lys Val<br>335 340 345 | 1300 |
| gag gag aca gtt gag ttc tac tct tcc atc ttt gga gtc atg cag ctg<br>Glu Glu Thr Val Glu Phe Tyr Ser Ser Ile Phe Gly Val Met Gln Leu<br>350 355 360 | 1348 |
| ttg tgt ctt ctc acc tgc ccc ctc att ggc tac atc atg gac tgg cgc<br>Leu Cys Leu Leu Thr Cys Pro Leu Ile Gly Tyr Ile Met Asp Trp Arg<br>365 370 375 380 | 1396 |
| atc aag gac tgt gtg gat gct cca acg gag ggc acc ctg aat gag aat<br>Ile Lys Asp Cys Val Asp Ala Pro Thr Glu Gly Thr Leu Asn Glu Asn<br>385 390 395 | 1444 |
| gct tcc ttt gga gat gcc aga gat ggg gct agc acc aag ttc act aga<br>Ala Ser Phe Gly Asp Ala Arg Asp Gly Ala Ser Thr Lys Phe Thr Arg<br>400 405 410 | 1492 |
| cca cgc tac cgc aag gta caa aag ctc acc aat gcc atc aat gcc ttc<br>Pro Arg Tyr Arg Lys Val Gln Lys Leu Thr Asn Ala Ile Asn Ala Phe<br>415 420 425 | 1540 |
| acc ctg acc aac atc ctg ctt gtg ggt ttc ggc atc gcc tgc ctc atc<br>Thr Leu Thr Asn Ile Leu Leu Val Gly Phe Gly Ile Ala Cys Leu Ile<br>430 435 440 | 1588 |
| aag aac tta cac ctg cag ttg ctg gcc ttt gtc ctg cat acc ata gtt<br>Lys Asn Leu His Leu Gln Leu Leu Ala Phe Val Leu His Thr Ile Val<br>445 450 455 460 | 1636 |
| cgc ggt ttc ttc cac tca gcc tgt gga ggt ctc tac gct gct gtg ttc<br>Arg Gly Phe Phe His Ser Ala Cys Gly Gly Leu Tyr Ala Ala Val Phe<br>465 470 475 | 1684 |
| ccg tcc aat cat ttt ggg aca ctg aca ggt ctt cag tct ctc atc agt<br>Pro Ser Asn His Phe Gly Thr Leu Thr Gly Leu Gln Ser Leu Ile Ser<br>480 485 490 | 1732 |
| gcc gtg ttt gct ctg ctg caa cag cta ctc ttc atg gcc atg gtg gga<br>Ala Val Phe Ala Leu Leu Gln Gln Leu Leu Phe Met Ala Met Val Gly<br>495 500 505 | 1780 |
| ccc ctg cat gga gat ccc ttc tgg gtg aac ctg ggc ctc cta ctt ctc<br>Pro Leu His Gly Asp Pro Phe Trp Val Asn Leu Gly Leu Leu Leu Leu<br>510 515 520 | 1828 |
| tcg ttc ctg gga ttt ctc cta cct tcc tac ctc tac tac cgg tct<br>Ser Phe Leu Gly Phe Leu Leu Pro Ser Tyr Leu Tyr Tyr Arg Ser<br>525 530 535 540 | 1876 |
| cgc ctg cag aga gag tat gcc acc aat ttg gta gac cca cag aag gtg<br>Arg Leu Gln Arg Glu Tyr Ala Thr Asn Leu Val Asp Pro Gln Lys Val<br>545 550 555 | 1924 |
| ctc aat act tcg aag gtg gct aca tagactcctg aggccaagag acttggagga<br>Leu Asn Thr Ser Lys Val Ala Thr<br>560 | 1978 |
| caggcagtca aggcctgata aaccgaaggg aatggcctgt ggctttctac ctgcatcgtg | 2038 |
| ttcatagagc cggggttctgt ggatttataa atactaagag ttctattttt gtagggactt | 2098 |
| gcaaaaaagg aaacaaacag aacaaaaccc ccaaaccaaa aacagccctt aaaaaactcc | 2158 |
| ccccaaccaa gctatccatc aactgaagac agtgcccgtt ccagtggtat tgggccatcg | 2218 |
| tctttgaaaa gaaagtgtgg ggctgccctt tctccacact tggcctagga gcctctgtgg | 2278 |
| agttgccttc tgaaaactca tgggatcagt gaacagacca cactaagatt ccagccgcca | 2338 |

```
agtgtgcaca catatatgtt acgcacatgc atattgcatc ctttcctgca ggagaaggac    2398
tgaggggctg gctgtatcca ggatggggtg tggggctgg agggcgggtt ccctccctga    2458
tgctgtttct tacaggtctt agaggaaata aaagggaaa tgaaaaaaaa aaaaaaaaa    2518 a                                                                    2519
```

<210> SEQ ID NO 4
<211> LENGTH: 564
<212> TYPE: PRT
<213> ORGANISM: Mus musculus

<400> SEQUENCE: 4

```
Met Ala Pro Thr Leu Lys Gln Ala Tyr Arg Arg Arg Trp Trp Met Ala
  1               5                  10                  15

Cys Thr Ala Val Val Glu Asn Leu Phe Phe Ser Ala Val Leu Leu Gly
                 20                  25                  30

Trp Ala Ser Leu Leu Ile Met Leu Lys Lys Glu Gly Phe Tyr Ser Ser
             35                  40                  45

Leu Cys Pro Ala Glu Asn Arg Thr Asn Thr Thr Gln Asp Glu Gln His
         50                  55                  60

Gln Trp Thr Ser Cys Asp Gln Gln Glu Lys Met Leu Asn Leu Gly Phe
 65                  70                  75                  80

Thr Ile Gly Ser Phe Leu Leu Ser Ala Thr Thr Leu Pro Leu Gly Ile
                 85                  90                  95

Leu Met Asp Arg Phe Gly Pro Arg Pro Leu Arg Leu Val Gly Ser Ala
            100                 105                 110

Cys Phe Ala Ala Ser Cys Thr Leu Met Ala Leu Ala Ser Arg Asp Thr
        115                 120                 125

Glu Val Leu Ser Pro Leu Ile Phe Leu Ala Leu Ser Leu Asn Gly Phe
    130                 135                 140

Ala Gly Ile Cys Leu Thr Phe Thr Ser Leu Thr Leu Pro Asn Met Phe
145                 150                 155                 160

Gly Asn Leu Arg Ser Thr Phe Met Ala Leu Met Ile Gly Ser Tyr Ala
                165                 170                 175

Ser Ser Ala Ile Thr Phe Pro Gly Ile Lys Leu Ile Tyr Asp Ala Gly
            180                 185                 190

Val Pro Phe Thr Val Ile Met Phe Thr Trp Ser Gly Leu Ala Cys Leu
        195                 200                 205

Ile Phe Leu Asn Cys Ala Leu Asn Trp Pro Ala Glu Ala Phe Pro Ala
    210                 215                 220

Pro Glu Glu Val Asp Tyr Thr Lys Lys Ile Lys Leu Ile Gly Leu Ala
225                 230                 235                 240

Leu Asp His Lys Val Thr Gly Asp Arg Phe Tyr Thr His Val Thr Ile
                245                 250                 255

Val Gly Gln Arg Leu Ser Gln Lys Ser Pro Ser Leu Glu Glu Gly Ala
            260                 265                 270

Asp Ala Phe Ile Ser Ser Pro Asp Ile Pro Gly Thr Ser Glu Glu Thr
        275                 280                 285

Pro Glu Lys Ser Val Pro Phe Arg Lys Ser Leu Cys Ser Pro Ile Phe
    290                 295                 300

Leu Trp Ser Leu Val Thr Met Gly Met Thr Gln Leu Arg Val Ile Phe
305                 310                 315                 320

Tyr Met Gly Ala Met Asn Lys Ile Leu Glu Phe Ile Val Thr Gly Gly
                325                 330                 335
```

-continued

```
Lys Glu Arg Glu Thr Asn Glu Gln Arg Gln Lys Val Glu Glu Thr Val
            340                 345                 350
Glu Phe Tyr Ser Ser Ile Phe Gly Val Met Gln Leu Leu Cys Leu Leu
            355                 360                 365
Thr Cys Pro Leu Ile Gly Tyr Ile Met Asp Trp Arg Ile Lys Asp Cys
            370                 375                 380
Val Asp Ala Pro Thr Glu Gly Thr Leu Asn Glu Asn Ala Ser Phe Gly
385                 390                 395                 400
Asp Ala Arg Asp Gly Ala Ser Thr Lys Phe Thr Arg Pro Arg Tyr Arg
                405                 410                 415
Lys Val Gln Lys Leu Thr Asn Ala Ile Asn Ala Phe Thr Leu Thr Asn
                420                 425                 430
Ile Leu Leu Val Gly Phe Gly Ile Ala Cys Leu Ile Lys Asn Leu His
            435                 440                 445
Leu Gln Leu Leu Ala Phe Val Leu His Thr Ile Val Arg Gly Phe Phe
            450                 455                 460
His Ser Ala Cys Gly Gly Leu Tyr Ala Ala Val Phe Pro Ser Asn His
465                 470                 475                 480
Phe Gly Thr Leu Thr Gly Leu Gln Ser Leu Ile Ser Ala Val Phe Ala
                485                 490                 495
Leu Leu Gln Gln Leu Leu Phe Met Ala Met Val Gly Pro Leu His Gly
                500                 505                 510
Asp Pro Phe Trp Val Asn Leu Gly Leu Leu Leu Ser Phe Leu Gly
                515                 520                 525
Phe Leu Leu Pro Ser Tyr Leu Tyr Tyr Arg Ser Arg Leu Gln Arg
            530                 535                 540
Glu Tyr Ala Thr Asn Leu Val Asp Pro Gln Lys Val Leu Asn Thr Ser
545                 550                 555                 560
Lys Val Ala Thr
```

```
<210> SEQ ID NO 5
<211> LENGTH: 3271
<212> TYPE: DNA
<213> ORGANISM: Homo sapiens
<220> FEATURE:
<221> NAME/KEY: CDS
<222> LOCATION: (308)..(2026)

<400> SEQUENCE: 5
gtcagggtcc ctgggagagg cagccctcgg atctgcccct gcccacctca cgctgcgttc      60
catgctggcc ccaggcgatg tcagtcctgc tgcaggccag gactagttcc acggccctga     120
gcatgcgtta gccccttctt gcctccatgc ctcagtttac ctcggagtga gctgcgggag     180
acgtctccct gcctggccgg ggcggctctg tcgtagcgga gggcagcggt acgagccggc     240
cgcgggctcg gggtgtccca ggtggtgcag agcggagcc ggagccggag ccgcgccgcg      300 ccgcacc atg gcg ccc acc ctg gcc act gcc cat cgg cgc cgc tgg tgg      349
        Met Ala Pro Thr Leu Ala Thr Ala His Arg Arg Arg Trp Trp
          1               5                  10 atg gcc tgc acg gcc gtg ctg gag aac ctc ctc ttc tcg gca gtc ctc      397
Met Ala Cys Thr Ala Val Leu Glu Asn Leu Leu Phe Ser Ala Val Leu
 15                  20                  25                  30 ctg ggc tgg ggc tcg ctg ctc atc atg ctc aag tca gag ggc ttt tac      445
Leu Gly Trp Gly Ser Leu Leu Ile Met Leu Lys Ser Glu Gly Phe Tyr
                 35                  40                  45 tcc tac ctg tgt acc gag cca gag aat gtc acc aat ggc aca gtg ggc      493
Ser Tyr Leu Cys Thr Glu Pro Glu Asn Val Thr Asn Gly Thr Val Gly
```

-continued

```
                    50                      55                      60
ggc aca gca gag ccg ggg cac gag gag gtg agc tgg atg aac ggc tgg      541
Gly Thr Ala Glu Pro Gly His Glu Glu Val Ser Trp Met Asn Gly Trp
            65                      70                      75 ctc agc tgc cag gcc cag gac gag atg cta aat ttg gcc ttc act gtg      589
Leu Ser Cys Gln Ala Gln Asp Glu Met Leu Asn Leu Ala Phe Thr Val
        80                      85                      90 ggc tcc ttt ctg ctc agt gcc atc acc ctg ccc ctg ggt atc gtc atg      637
Gly Ser Phe Leu Leu Ser Ala Ile Thr Leu Pro Leu Gly Ile Val Met
    95                     100                     105             110 gac aag tat ggc ccg agg aag ctc agg ctg ctg ggc agc gcc tgc ttc      685
Asp Lys Tyr Gly Pro Arg Lys Leu Arg Leu Leu Gly Ser Ala Cys Phe
                       115                     120                     125 gcg gtt tcc tgc ttg ctg att gcg tac gga gca agt aaa cca aac gct      733
Ala Val Ser Cys Leu Leu Ile Ala Tyr Gly Ala Ser Lys Pro Asn Ala
                130                     135                     140 ctc tcc gtg ctc atc ttc atc gcc ctg gct ctg aat ggc ttt ggt ggg      781
Leu Ser Val Leu Ile Phe Ile Ala Leu Ala Leu Asn Gly Phe Gly Gly
            145                     150                     155 atg tgt atg acc ttc acc tca tta aca ctg ccc aac atg ttc ggc gac      829
Met Cys Met Thr Phe Thr Ser Leu Thr Leu Pro Asn Met Phe Gly Asp
        160                     165                     170 ctt cgg tcc acg ttt att gcc ttg atg att ggg tcc tac gcc tcc tcg      877
Leu Arg Ser Thr Phe Ile Ala Leu Met Ile Gly Ser Tyr Ala Ser Ser
175                     180                     185                     190 gca gtc acc ttt cca gga atc aag ctc atc tat gat gct ggt gtc tcc      925
Ala Val Thr Phe Pro Gly Ile Lys Leu Ile Tyr Asp Ala Gly Val Ser
                       195                     200                     205 ttc atc gtc gtc ctc gtg gtc tgg gcc ggc tgc tcc ggg ctg gtt ttc      973
Phe Ile Val Val Leu Val Val Trp Ala Gly Cys Ser Gly Leu Val Phe
                210                     215                     220 ctc aac tgc ttc ttt aac tgg ccc ctt gag ccc ttc ccg ggg ccg gag     1021
Leu Asn Cys Phe Phe Asn Trp Pro Leu Glu Pro Phe Pro Gly Pro Glu
            225                     230                     235 gac atg gac tac tcg gtg aag atc aag ttc agc tgg ctg ggc ttt gac     1069
Asp Met Asp Tyr Ser Val Lys Ile Lys Phe Ser Trp Leu Gly Phe Asp
        240                     245                     250 cac aag atc aca ggg aag cag ttc tac aag cag gtg acc acg gtg ggc     1117
His Lys Ile Thr Gly Lys Gln Phe Tyr Lys Gln Val Thr Thr Val Gly
255                     260                     265                     270 cgg cgc ctg agt gtg ggc agc tcc atg agg agt gcc aag gag cag gtg     1165
Arg Arg Leu Ser Val Gly Ser Ser Met Arg Ser Ala Lys Glu Gln Val
                       275                     280                     285 gcg ctg cag gag ggc cac aag ctg tgc ctg tcc acc gtc gac ctg gag     1213
Ala Leu Gln Glu Gly His Lys Leu Cys Leu Ser Thr Val Asp Leu Glu
                290                     295                     300 gtg aag tgc cag ccg gat gcc gca gtg gcc ccc tcc ttc atg cac agc     1261
Val Lys Cys Gln Pro Asp Ala Ala Val Ala Pro Ser Phe Met His Ser
            305                     310                     315 gtg ttc agc ccc atc ctg ctc ctc agc ctg gtc acc atg tgc gtc acg     1309
Val Phe Ser Pro Ile Leu Leu Leu Ser Leu Val Thr Met Cys Val Thr
        320                     325                     330 cag ctg cgg ctc atc ttc tac atg ggg gct atg aac aac atc ctc aag     1357
Gln Leu Arg Leu Ile Phe Tyr Met Gly Ala Met Asn Asn Ile Leu Lys
335                     340                     345                     350 ttc ctg gtc agc ggc gac cag aag aca gtg atg gcc acg gtt ggc ctc     1405
Phe Leu Val Ser Gly Asp Gln Lys Thr Val Met Ala Thr Val Gly Leu
                       355                     360                     365 tac acc tcc atc ttc ggc gtg ctc cag ctg ctg tgc ctg ctg acg gcc     1453
```

```
                Tyr Thr Ser Ile Phe Gly Val Leu Gln Leu Leu Cys Leu Leu Thr Ala
                                370                 375                 380 ccc gtc att ggc tac atc atg gac tgg agg ctg aag gag tgt gaa gac              1501
Pro Val Ile Gly Tyr Ile Met Asp Trp Arg Leu Lys Glu Cys Glu Asp
        385                 390                 395 gcc tcc gag gag ccc gag gag aaa gac gcc aac caa ggc gag aag aaa              1549
Ala Ser Glu Glu Pro Glu Glu Lys Asp Ala Asn Gln Gly Glu Lys Lys
    400                 405                 410 aag aag aag cgg gac cgg cag atc cag aag atc act aat gcc atg cgg              1597
Lys Lys Lys Arg Asp Arg Gln Ile Gln Lys Ile Thr Asn Ala Met Arg
415                 420                 425                 430 gcc ttc gcc ttc acc aac ctg ctc ctc gtg ggc ttt ggg gtg acc tgc              1645
Ala Phe Ala Phe Thr Asn Leu Leu Leu Val Gly Phe Gly Val Thr Cys
                435                 440                 445 ctc att ccc aac ctg cct ctc cag atc ctc tcc ttc atc ctg cac aca              1693
Leu Ile Pro Asn Leu Pro Leu Gln Ile Leu Ser Phe Ile Leu His Thr
                450                 455                 460 atc gtg cga gga ttc atc cac tcc gct gtc ggg ggc ctg tac gct gcc              1741
Ile Val Arg Gly Phe Ile His Ser Ala Val Gly Gly Leu Tyr Ala Ala
            465                 470                 475 gtg tac ccc tcc acc cag ttc ggc agc ctc acg gga ctg cag tct ctg              1789
Val Tyr Pro Ser Thr Gln Phe Gly Ser Leu Thr Gly Leu Gln Ser Leu
        480                 485                 490 atc agc gcg ctc ttc gcc ctt ctg cag cag ccg ctg ttt ctg gcc atg              1837
Ile Ser Ala Leu Phe Ala Leu Leu Gln Gln Pro Leu Phe Leu Ala Met
495                 500                 505                 510 atg ggt cct ctc cag gga gac cct ctg tgg gtg aac gtg ggg ctg ctc              1885
Met Gly Pro Leu Gln Gly Asp Pro Leu Trp Val Asn Val Gly Leu Leu
                515                 520                 525 ctt ctc agc ctg ctg ggc ttc tgc ctc ccg ctc tac ctg atc tgc tac              1933
Leu Leu Ser Leu Leu Gly Phe Cys Leu Pro Leu Tyr Leu Ile Cys Tyr
                530                 535                 540 cgg cgc cag ctg gag cgg cag ctg cag cag agg cag gag gat gac aaa              1981
Arg Arg Gln Leu Glu Arg Gln Leu Gln Gln Arg Gln Glu Asp Asp Lys
            545                 550                 555 ctc ttc ctc aaa atc aac ggc tcg tcc aac cag gag gcc ttc gtg                  2026
Leu Phe Leu Lys Ile Asn Gly Ser Ser Asn Gln Glu Ala Phe Val
        560                 565                 570 tagtggctgc cgcctcggaa ctgcggtctc ctgcctgtgc ttcagtgact gacccctgtc            2086
ctgcccctcc agagtacccc acgcacccccc aggaccttcg ccgtctccgt gccagcgttc           2146
acgctccctc ccggggcccct gcctcggagc tctgtggtgg aaggacggga gagggccccg           2206
gacacgcgag ttttctcctg ccgaacgcag gggctgccct gactttgctc tgccgccccc            2266
cggggacccg gggcctgggg tctctgtggt gcctgcagca ggagccagga acgcccggca            2326
ggcaggcgct ctcccgccag tgtctggatt ctgcctcttg ccaaagcaga ggggctgcc             2386 atcccctgcc tgccacctgc cctcggctg catgcccaca gccatacctg cctgaggaca            2446
aaggcttgca ctgtctcgcc tgcgcctggc ccccacccccc tccccggcca gcctgaggct          2506
gcctgaggaa ggaaggaccc gcttcctgtt gtcggtgcta attcctttgt aattccagcc            2566
ccctgtcgcc tgtccagggc ctgcccaccc gttggaggcc ggtggagaag ccccacctgg            2626
cttatgccct ggagagggtt tagcgggctg ggtggacccc tcgcctcctc ccgagggcc             2686 aatgccgcgg acacgttttc actgtcaccc tcgttctgtc tgccacctga agggaatttg            2746
aggaccgccg ccagggcacc ccgtacatac acacagctgc ttttgtggag gtggacgaaa            2806
ggctgtggcc ggcagacgtg gaggtccagg ccggggtggg gacgtggtg ggtccgaggg             2866
```

```
gtgtgtgggg tcggggtggg ctctaggagt tagcccttat ccccactgac caggcgggag    2926
ccgccaggcc tgcagctggg ccagtgccca ggagccatcc tggcgtgggg ccaggagctt    2986
gtccaaggcc acaggcccac agcacccct gccggcgggc tccgtggggc cctggagctg    3046
atgacggggg aggcccgtcc gcctggccca ccaacccgcc caccttgact gccccagaa    3106 gtgtgtcttg agacctcctg ggcgtgctta gaggggtgag ttgtgtttgg attttagtt    3166 attttctctt cagttttatt agacttcttt tttataaagc aataaatcca ttttcctccg    3226
ggtaagggat gccccttctg gcatatcaaa aaaaaaaaa aaaaa                    3271
```

<210> SEQ ID NO 6
<211> LENGTH: 573
<212> TYPE: PRT
<213> ORGANISM: Homo sapiens

<400> SEQUENCE: 6

```
Met Ala Pro Thr Leu Ala Thr Ala His Arg Arg Trp Trp Met Ala
  1               5                  10                  15

Cys Thr Ala Val Leu Glu Asn Leu Leu Phe Ser Ala Val Leu Leu Gly
                 20                  25                  30

Trp Gly Ser Leu Leu Ile Met Leu Lys Ser Glu Gly Phe Tyr Ser Tyr
             35                  40                  45

Leu Cys Thr Glu Pro Glu Asn Val Thr Asn Gly Thr Val Gly Gly Thr
         50                  55                  60

Ala Glu Pro Gly His Glu Glu Val Ser Trp Met Asn Gly Trp Leu Ser
 65                  70                  75                  80

Cys Gln Ala Gln Asp Glu Met Leu Asn Leu Ala Phe Thr Val Gly Ser
                 85                  90                  95

Phe Leu Leu Ser Ala Ile Thr Leu Pro Leu Gly Ile Val Met Asp Lys
                100                 105                 110

Tyr Gly Pro Arg Lys Leu Arg Leu Leu Gly Ser Ala Cys Phe Ala Val
            115                 120                 125

Ser Cys Leu Leu Ile Ala Tyr Gly Ala Ser Lys Pro Asn Ala Leu Ser
        130                 135                 140

Val Leu Ile Phe Ile Ala Leu Ala Leu Asn Gly Phe Gly Gly Met Cys
145                 150                 155                 160

Met Thr Phe Thr Ser Leu Thr Leu Pro Asn Met Phe Gly Asp Leu Arg
                165                 170                 175

Ser Thr Phe Ile Ala Leu Met Ile Gly Ser Tyr Ala Ser Ser Ala Val
            180                 185                 190

Thr Phe Pro Gly Ile Lys Leu Ile Tyr Asp Ala Gly Val Ser Phe Ile
        195                 200                 205

Val Val Leu Val Val Trp Ala Gly Cys Ser Gly Leu Val Phe Leu Asn
    210                 215                 220

Cys Phe Asn Trp Pro Leu Glu Pro Phe Pro Gly Pro Glu Asp Met
225                 230                 235                 240

Asp Tyr Ser Val Lys Ile Lys Phe Ser Trp Leu Gly Phe Asp His Lys
                245                 250                 255

Ile Thr Gly Lys Gln Phe Tyr Lys Gln Val Thr Thr Val Gly Arg Arg
            260                 265                 270

Leu Ser Val Gly Ser Ser Met Arg Ser Ala Lys Glu Gln Val Ala Leu
        275                 280                 285

Gln Glu Gly His Lys Leu Cys Leu Ser Thr Val Asp Leu Glu Val Lys
    290                 295                 300
```

```
Cys Gln Pro Asp Ala Ala Val Ala Pro Ser Phe Met His Ser Val Phe
305                 310                 315                 320

Ser Pro Ile Leu Leu Leu Ser Leu Val Thr Met Cys Val Thr Gln Leu
            325                 330                 335

Arg Leu Ile Phe Tyr Met Gly Ala Met Asn Asn Ile Leu Lys Phe Leu
        340                 345                 350

Val Ser Gly Asp Gln Lys Thr Val Met Ala Thr Val Gly Leu Tyr Thr
    355                 360                 365

Ser Ile Phe Gly Val Leu Gln Leu Leu Cys Leu Leu Thr Ala Pro Val
    370                 375                 380

Ile Gly Tyr Ile Met Asp Trp Arg Leu Lys Glu Cys Glu Asp Ala Ser
385                 390                 395                 400

Glu Glu Pro Glu Glu Lys Asp Ala Asn Gln Gly Glu Lys Lys Lys Lys
                405                 410                 415

Lys Arg Asp Arg Gln Ile Gln Lys Ile Thr Asn Ala Met Arg Ala Phe
            420                 425                 430

Ala Phe Thr Asn Leu Leu Leu Val Gly Phe Gly Val Thr Cys Leu Ile
        435                 440                 445

Pro Asn Leu Pro Leu Gln Ile Leu Ser Phe Ile Leu His Thr Ile Val
    450                 455                 460

Arg Gly Phe Ile His Ser Ala Val Gly Leu Tyr Ala Ala Val Tyr
465                 470                 475                 480

Pro Ser Thr Gln Phe Gly Ser Leu Thr Gly Leu Gln Ser Leu Ile Ser
                485                 490                 495

Ala Leu Phe Ala Leu Leu Gln Gln Pro Leu Phe Leu Ala Met Met Gly
            500                 505                 510

Pro Leu Gln Gly Asp Pro Leu Trp Val Asn Val Gly Leu Leu Leu Leu
        515                 520                 525

Ser Leu Leu Gly Phe Cys Leu Pro Leu Tyr Leu Ile Cys Tyr Arg Arg
    530                 535                 540

Gln Leu Glu Arg Gln Leu Gln Arg Gln Glu Asp Asp Lys Leu Phe
545                 550                 555                 560

Leu Lys Ile Asn Gly Ser Ser Asn Gln Glu Ala Phe Val
            565                 570
```

```
<210> SEQ ID NO 7
<211> LENGTH: 3236
<212> TYPE: DNA
<213> ORGANISM: Mus musculus
<220> FEATURE:
<221> NAME/KEY: CDS
<222> LOCATION: (123)..(1826)

<400> SEQUENCE: 7
agaaaaggcg ccgggcgggc ccgatacaca ctggtaggag ccgggtgagc tggactccca      60
ggatccgggt ctcagacgag ggtgtctgca gaaccggagc ccgaccaccg ccacaccgca     120 cc atg gcg ccc acc ctg gcc act gcc cat cgg cgc cgc tgg tgg atg       167
   Met Ala Pro Thr Leu Ala Thr Ala His Arg Arg Arg Trp Trp Met
   1               5                   10                  15 gcc tgc acc gct gtg ttg gaa aac ctc ctt ttc tcc gca gtc ctc ctg       215
Ala Cys Thr Ala Val Leu Glu Asn Leu Leu Phe Ser Ala Val Leu Leu
                20                  25                  30 ggc tgg ggt tcg ctg ctc atc atg ctc aag tcc gag ggc ttt tac tcc       263
Gly Trp Gly Ser Leu Leu Ile Met Leu Lys Ser Glu Gly Phe Tyr Ser
            35                  40                  45 tac ctg tgt acg aag cca gag aat gtc act aac agc acg gtc ggg ggc       311
```

```
                Tyr Leu Cys Thr Lys Pro Glu Asn Val Thr Asn Ser Thr Val Gly Gly
                            50                  55                  60 agc gca gag ccg gaa ccc gag gag ttg agc ctg gtg aat ggc tgg ctc                      359
Ser Ala Glu Pro Glu Pro Glu Glu Leu Ser Leu Val Asn Gly Trp Leu
         65                  70                  75 agc tgt aag gcc cag gat gag att ctg aat ttg gcc ttc acc gtg ggc                      407
Ser Cys Lys Ala Gln Asp Glu Ile Leu Asn Leu Ala Phe Thr Val Gly
 80              85                  90                  95 tcc ttc ctg ctc agt gcc atc acc ctg cct ctg ggc atc atc atg gac                      455
Ser Phe Leu Leu Ser Ala Ile Thr Leu Pro Leu Gly Ile Ile Met Asp
                100                 105                 110 aag tat ggt cca agg aag ctc agg ctg ctg ggc agt gct tgc ttt gct                      503
Lys Tyr Gly Pro Arg Lys Leu Arg Leu Leu Gly Ser Ala Cys Phe Ala
            115                 120                 125 gtc tcc tgc ttg ctg att gca tat gga gca agt aac cca gac tcg ctc                      551
Val Ser Cys Leu Leu Ile Ala Tyr Gly Ala Ser Asn Pro Asp Ser Leu
        130                 135                 140 tct gtg ctc atc ttt atc gcc ttg gct ctg aac ggc ttt ggg ggg atg                      599
Ser Val Leu Ile Phe Ile Ala Leu Ala Leu Asn Gly Phe Gly Gly Met
    145                 150                 155 tgc atg acg ttc act tcg tta aca ctg ccc aat atg ttc ggc gac ctt                      647
Cys Met Thr Phe Thr Ser Leu Thr Leu Pro Asn Met Phe Gly Asp Leu
160                 165                 170                 175 cgg tcc aca ttt att gcc ttg atg att gga tcc tac gct tcc tca gca                      695
Arg Ser Thr Phe Ile Ala Leu Met Ile Gly Ser Tyr Ala Ser Ser Ala
                180                 185                 190 gtt acc ttc cca gga ata aag ctc atc tac gac gct ggc gcc tcc ttc                      743
Val Thr Phe Pro Gly Ile Lys Leu Ile Tyr Asp Ala Gly Ala Ser Phe
            195                 200                 205 att ggc atc cta gtg gtc tgg gct ggc tgc tct ggc ctg gtt ttt ttc                      791
Ile Gly Ile Leu Val Val Trp Ala Gly Cys Ser Gly Leu Val Phe Phe
        210                 215                 220 aac tgt ttc ttc aac tgg cca ctc gag ccc ttc cca ggc tca gag gac                      839
Asn Cys Phe Phe Asn Trp Pro Leu Glu Pro Phe Pro Gly Ser Glu Asp
    225                 230                 235 atg gac tac tcg gtg aag atc aag ttc agc tgg cta ggc ttt gac cac                      887
Met Asp Tyr Ser Val Lys Ile Lys Phe Ser Trp Leu Gly Phe Asp His
240                 245                 250                 255 aag atc aca ggg aag cag ttc tac aag cag gtg acc aca gtg ggg cgc                      935
Lys Ile Thr Gly Lys Gln Phe Tyr Lys Gln Val Thr Thr Val Gly Arg
                260                 265                 270 cgt ctg agc gtg ggc agc tct atg cgg act gcc aag gag caa gcc gcc                      983
Arg Leu Ser Val Gly Ser Ser Met Arg Thr Ala Lys Glu Gln Ala Ala
            275                 280                 285 ctg cag gag ggc cac aag ctg tgt ctg tcc act gtg gac ctg gag gtg                     1031
Leu Gln Glu Gly His Lys Leu Cys Leu Ser Thr Val Asp Leu Glu Val
        290                 295                 300 aag tgc cag cct gat gct gca gcg gcc cca tcg ttt atg cac agt gtg                     1079
Lys Cys Gln Pro Asp Ala Ala Ala Ala Pro Ser Phe Met His Ser Val
    305                 310                 315 ttc agc ccc ctc ctg gtg ctc agc ctg gtc acc atg tgt gtc aca cag                     1127
Phe Ser Pro Leu Leu Val Leu Ser Leu Val Thr Met Cys Val Thr Gln
320                 325                 330                 335 ctg cga ctt atc ttc tac atg ggg gct atg aac agc atc ctt gag ttc                     1175
Leu Arg Leu Ile Phe Tyr Met Gly Ala Met Asn Ser Ile Leu Glu Phe
                340                 345                 350 ctg gtc agg ggg gac cag aag aca gtt gcc ctc tat acc tcc atc ttt                     1223
Leu Val Arg Gly Asp Gln Lys Thr Val Ala Leu Tyr Thr Ser Ile Phe
            355                 360                 365
```

```
ggc gca ctc cag ctg ctc tgc ctg ctg aca gct cct gtc atc ggc tac    1271
Gly Ala Leu Gln Leu Leu Cys Leu Leu Thr Ala Pro Val Ile Gly Tyr
            370                 375                 380 atc atg gac tgg aag ctg aaa gag tgt gaa gat act tca gag gag cct    1319
Ile Met Asp Trp Lys Leu Lys Glu Cys Glu Asp Thr Ser Glu Glu Pro
        385                 390                 395 gag gag gaa gaa ggc act caa ggt gaa aag aag cag aaa cga gac agg    1367
Glu Glu Glu Glu Gly Thr Gln Gly Glu Lys Lys Gln Lys Arg Asp Arg
400                 405                 410                 415 cag att cag aaa gtc acg aat gcc atg cgg gcc ttc gcc ttt aca aac    1415
Gln Ile Gln Lys Val Thr Asn Ala Met Arg Ala Phe Ala Phe Thr Asn
                420                 425                 430 gtg ctg ctt gtg ggt ttt ggg gtg acc tgc ctc att ccc aac ctg cct    1463
Val Leu Leu Val Gly Phe Gly Val Thr Cys Leu Ile Pro Asn Leu Pro
            435                 440                 445 cta cag atc ttc tcc ttc gtc ctg cac aca att gtg cga gga ttc atc    1511
Leu Gln Ile Phe Ser Phe Val Leu His Thr Ile Val Arg Gly Phe Ile
        450                 455                 460 cac tct gcc gta ggg ggc cta tac gct gcc gtg tac ccc tcc aca cag    1559
His Ser Ala Val Gly Gly Leu Tyr Ala Ala Val Tyr Pro Ser Thr Gln
465                 470                 475 ttt ggt agc ctc act gga ctg cag tcc ctg gtc agt gcg ctc ttt gct    1607
Phe Gly Ser Leu Thr Gly Leu Gln Ser Leu Val Ser Ala Leu Phe Ala
480                 485                 490                 495 ctc ctg cag cag ccg ctg tat ctg gcc atg atg ggt cct ctg gga gga    1655
Leu Leu Gln Gln Pro Leu Tyr Leu Ala Met Met Gly Pro Leu Gly Gly
                500                 505                 510 gac cct ctg tgg gtg aac gtg ggt ctg ctc gcc atg agc atg ctg ggc    1703
Asp Pro Leu Trp Val Asn Val Gly Leu Leu Ala Met Ser Met Leu Gly
            515                 520                 525 ttc tgc ctg ccc ctt tac ctc atc tgc tac cgg cgc cag ctg gag agg    1751
Phe Cys Leu Pro Leu Tyr Leu Ile Cys Tyr Arg Arg Gln Leu Glu Arg
        530                 535                 540 cag ctg cag cag aag agg gaa gac agc aag ctg ttc ctt aag atc aat    1799
Gln Leu Gln Gln Lys Arg Glu Asp Ser Lys Leu Phe Leu Lys Ile Asn
545                 550                 555 ggc tca tcc aac cgg gag gct ttc gtg tagtgcccac ccaccgcctc          1846
Gly Ser Ser Asn Arg Glu Ala Phe Val
560                 565 agttgtggcc tcctgcctgt gcttcagtga ctgactgcag tcatctcccc acccagagg   1906 acctcatgct ctccctggat cctgcccttc accacactgg agcccatact tcctcagaac   1966
cacctggccc tgccgtggag tgctggtgtg gagggacagg agagggcctg ggacaagtga   2026 acctccact gccagaagct gggctgccct ggcctagctg tcaccccagg ggctctgaag    2086
tctcccgatc tccatggggc ttgtacctgg agccaagggg accttttcag cgagcatttc   2146
tttcttttta ttttttcttt ctctttctca ctgatcggat tctgcctctt gccaaagcag   2206
aggggcctgc catcctccag cacactacct gtccctgagc tgcacgccca ccaaccacgc   2266
ccacctgagg acaaaggctt gcgctgtctg cactcccctt gcttggcccc ttacctcccc   2326
tggccagtct ggctgcctga ggaaggaagg accgcttcc tgttgttggt gctaaccct    2386 ttgtcatccc aacacccccc tgccgtggc tagtctctgg cccctcttt ccttgaaagc    2446 ctgagaagaa gccccctg tctcaggctg ggaaggagt ggaggcaga ctatttacac      2506 aaagcctcaa gagccctggg ccaggcttct tcctccggag ccagagcagt gtctctctgc   2566
tggcacgctt tgttccagtc tgcaacctga agggaactaa gggacacca caagggcacc   2626 ctcccatcca cccacagctg tttttctggg gtggaaataa ggctgtgact agacatgagg   2686
```

-continued

```
agccaagcct aaatagggaa gaggattagt gagtaacccg aggggtgtgt gtttatgtgg    2746
tacgtgtgtg tgcatgtgtg tatatggtag gaggctagcc ccaggggctg cttttatcag    2806
agtggaccag accagaagcc agccagccct acagcaggct caaaatagga gtcagccttg    2866
ctttatgatg gggacctgtg tgtatcggtg tgatcacagt gcccctgct ggcagactca     2926 catcaggggga ctggaacggt tcatgtagta aagcctagc cggcctgcct ggctcactaa    2986
cccaccttgc cttgacaacc cctagaaacc ctgcctgaga cctcttgggg tgccaagagg    3046
ggtacattgg ttttttaagtt tatggttttc tcttgtttta tcatgattct ttttatgaag   3106
caataaatcc atttccctgt tggtaatgga tgccctcct cacgtatcag ctaattactg     3166
tatgtgccta ttttatattt gagaggagag acagggcaaa agggtctgcc aggaaaaaaa    3226
aaaaaaaaaa                                                           3236
```

<210> SEQ ID NO 8
<211> LENGTH: 568
<212> TYPE: PRT
<213> ORGANISM: Mus musculus

<400> SEQUENCE: 8

```
Met Ala Pro Thr Leu Ala Thr Ala His Arg Arg Trp Trp Met Ala
 1               5                  10                  15

Cys Thr Ala Val Leu Glu Asn Leu Leu Phe Ser Ala Val Leu Leu Gly
                20                  25                  30

Trp Gly Ser Leu Leu Ile Met Leu Lys Ser Glu Gly Phe Tyr Ser Tyr
            35                  40                  45

Leu Cys Thr Lys Pro Glu Asn Val Thr Asn Ser Thr Val Gly Gly Ser
        50                  55                  60

Ala Glu Pro Glu Pro Glu Glu Leu Ser Leu Val Asn Gly Trp Leu Ser
65                  70                  75                  80

Cys Lys Ala Gln Asp Glu Ile Leu Asn Leu Ala Phe Thr Val Gly Ser
                85                  90                  95

Phe Leu Leu Ser Ala Ile Thr Leu Pro Leu Gly Ile Ile Met Asp Lys
            100                 105                 110

Tyr Gly Pro Arg Lys Leu Arg Leu Leu Gly Ser Ala Cys Phe Ala Val
        115                 120                 125

Ser Cys Leu Leu Ile Ala Tyr Gly Ala Ser Asn Pro Asp Ser Leu Ser
    130                 135                 140

Val Leu Ile Phe Ile Ala Leu Ala Leu Asn Gly Phe Gly Gly Met Cys
145                 150                 155                 160

Met Thr Phe Thr Ser Leu Thr Leu Pro Asn Met Phe Gly Asp Leu Arg
                165                 170                 175

Ser Thr Phe Ile Ala Leu Met Ile Gly Ser Tyr Ala Ser Ser Ala Val
            180                 185                 190

Thr Phe Pro Gly Ile Lys Leu Ile Tyr Asp Ala Gly Ala Ser Phe Ile
        195                 200                 205

Gly Ile Leu Val Val Trp Ala Gly Cys Ser Gly Leu Val Phe Phe Asn
    210                 215                 220

Cys Phe Phe Asn Trp Pro Leu Glu Pro Phe Pro Gly Ser Glu Asp Met
225                 230                 235                 240

Asp Tyr Ser Val Lys Ile Lys Phe Ser Trp Leu Gly Phe Asp His Lys
                245                 250                 255

Ile Thr Gly Lys Gln Phe Tyr Lys Gln Val Thr Thr Val Gly Arg Arg
            260                 265                 270
```

-continued

```
Leu Ser Val Gly Ser Ser Met Arg Thr Ala Lys Glu Gln Ala Ala Leu
        275                 280                 285

Gln Glu Gly His Lys Leu Cys Leu Ser Thr Val Asp Leu Glu Val Lys
        290                 295                 300

Cys Gln Pro Asp Ala Ala Ala Pro Ser Phe Met His Ser Val Phe
305                 310                 315                 320

Ser Pro Leu Leu Val Leu Ser Leu Val Thr Met Cys Val Thr Gln Leu
                325                 330                 335

Arg Leu Ile Phe Tyr Met Gly Ala Met Asn Ser Ile Leu Glu Phe Leu
                340                 345                 350

Val Arg Gly Asp Gln Lys Thr Val Ala Leu Tyr Thr Ser Ile Phe Gly
        355                 360                 365

Ala Leu Gln Leu Leu Cys Leu Leu Thr Ala Pro Val Ile Gly Tyr Ile
        370                 375                 380

Met Asp Trp Lys Leu Lys Glu Cys Glu Asp Thr Ser Glu Glu Pro Glu
385                 390                 395                 400

Glu Glu Glu Gly Thr Gln Gly Glu Lys Lys Gln Lys Arg Asp Arg Gln
                405                 410                 415

Ile Gln Lys Val Thr Asn Ala Met Arg Ala Phe Ala Phe Thr Asn Val
                420                 425                 430

Leu Leu Val Gly Phe Gly Val Thr Cys Leu Ile Pro Asn Leu Pro Leu
        435                 440                 445

Gln Ile Phe Ser Phe Val Leu His Thr Ile Val Arg Gly Phe Ile His
        450                 455                 460

Ser Ala Val Gly Gly Leu Tyr Ala Ala Val Tyr Pro Ser Thr Gln Phe
465                 470                 475                 480

Gly Ser Leu Thr Gly Leu Gln Ser Leu Val Ser Ala Leu Phe Ala Leu
                485                 490                 495

Leu Gln Gln Pro Leu Tyr Leu Ala Met Met Gly Pro Leu Gly Gly Asp
                500                 505                 510

Pro Leu Trp Val Asn Val Gly Leu Leu Ala Met Ser Met Leu Gly Phe
        515                 520                 525

Cys Leu Pro Leu Tyr Leu Ile Cys Tyr Arg Arg Gln Leu Glu Arg Gln
        530                 535                 540

Leu Gln Gln Lys Arg Glu Asp Ser Lys Leu Phe Leu Lys Ile Asn Gly
545                 550                 555                 560

Ser Ser Asn Arg Glu Ala Phe Val
                565
```